US008894998B2

(12) United States Patent
Rinkenberger et al.

(10) Patent No.: US 8,894,998 B2
(45) Date of Patent: Nov. 25, 2014

(54) ANTIBODIES DIRECTED TO αVβ6 AND USES THEREOF

(71) Applicant: MedImmune Limited, Cambridge (GB)

(72) Inventors: Julie Rinkenberger, Moraga, CA (US); Ian Foltz, British Columbia (CA); Avril Alfred, British Columbia (CA); Simon Thomas Barry, Macclesfield (GB); Vahe Bedian, Waltham, MA (US)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 13/760,426

(22) Filed: Feb. 6, 2013

(65) Prior Publication Data

US 2013/0202621 A1 Aug. 8, 2013

Related U.S. Application Data

(60) Division of application No. 12/782,335, filed on May 18, 2010, now Pat. No. 8,398,975, which is a continuation of application No. 11/833,486, filed on Aug. 3, 2007, now abandoned.

(60) Provisional application No. 60/835,559, filed on Aug. 3, 2006.

(51) Int. Cl.
*A61K 39/395* (2006.01)
*C07K 16/28* (2006.01)

(52) U.S. Cl.
CPC ....... *C07K 16/2839* (2013.01); *C07K 2317/565* (2013.01); *C07K 2317/56* (2013.01); *C07K 2316/96* (2013.01); *C07K 2317/567* (2013.01); *C07K 2317/92* (2013.01); *C07K 2317/21* (2013.01)
USPC ................... 424/130.1; 424/133.1; 424/143.1

(58) Field of Classification Search
None
See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,569,825 | A | 10/1996 | Lonberg et al. |
| 5,591,669 | A | 1/1997 | Krimpenfort et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,633,425 | A | 5/1997 | Lonberg et al. |
| 5,643,763 | A | 7/1997 | Dunn et al. |
| 5,661,016 | A | 8/1997 | Lonberg |
| 5,721,367 | A | 2/1998 | Kay et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 5,939,598 | A | 8/1999 | Kucherlapati et al. |
| 5,981,175 | A | 11/1999 | Loring et al. |
| 6,023,010 | A | 2/2000 | Krimpenfort et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,255,458 | B1 | 7/2001 | Lonberg et al. |
| 6,316,601 | B1 | 11/2001 | Huang et al. |
| 6,521,593 | B1 | 2/2003 | Laug |
| 6,673,986 | B1 | 1/2004 | Kucherlapati et al. |
| 6,692,741 | B2 | 2/2004 | Huang et al. |
| 7,150,871 | B2 * | 12/2006 | Huang et al. ............... 424/155.1 |
| 7,465,449 | B2 | 12/2008 | Violette et al. |
| 7,544,358 | B2 | 6/2009 | Huang et al. |
| 2001/0056076 | A1 | 12/2001 | Huang et al. |
| 2004/0048312 | A1 | 3/2004 | Li et al. |
| 2004/0093622 | A1 | 5/2004 | Kucherlapati et al. |
| 2004/0185507 | A1 | 9/2004 | Giles-Komar et al. |
| 2005/0076395 | A1 | 4/2005 | Kucherlapati et al. |
| 2005/0255102 | A1 | 11/2005 | Violette et al. |
| 2006/0127407 | A1 | 6/2006 | Chen et al. |
| 2008/0057063 | A1 | 3/2008 | Rinkenberger et al. |
| 2008/0286269 | A1 | 11/2008 | Violette et al. |
| 2009/0028853 | A1 | 1/2009 | Sheppard et al. |
| 2009/0123370 | A1 | 5/2009 | Howard et al. |
| 2009/0163698 | A1 | 6/2009 | Grigsby |
| 2009/0175784 | A1 | 7/2009 | Goldstein et al. |
| 2009/0196913 | A1 | 8/2009 | Huang et al. |

FOREIGN PATENT DOCUMENTS

| | | | |
|---|---|---|---|
| EP | 0463151 | B1 | 6/1996 |
| EP | 0773288 | A2 | 5/1997 |
| EP | 0546073 | B1 | 9/1997 |
| EP | 1049718 | B1 | 4/2006 |

(Continued)

OTHER PUBLICATIONS

Bandyopadhyay et al. Defining the Role of Integrin αvβ in Cancer. Curr Drug Targets. Jul. 2009; 10(7): 645-652.*
Eberlein et al "A human monoclonal antibody 264RAD targeting αvβ6 integrin reduces tumor growth and metastasis, and modulates key biomarkers in vivo" (Oncogene (2013), 32(37):4406-4416.*
Ghannad et al. Absence of αvβ6 Integrin Is Linked to Initiation and Progression of Periodontal Disease. The American Journal of Pathology, vol. 172, No. 5, May 2008.*
X Toma's Blanco-Mezquit et al. αVβ6 Integrin Promotes Corneal Wound Healing Investigative Ophthalmology & Visual Science, 2011, 52(11): 8505-8513.*

(Continued)

*Primary Examiner* — Maher Haddad

(57) ABSTRACT

Targeted binding agents, such antibodies directed to the antigen αVβ6 and uses of such agents are described. In particular, fully human monoclonal antibodies directed to the antigen αVβ6 are disclosed. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3 are disclosed. Hybridomas or other cell lines expressing such immunoglobulin molecules and monoclonal antibodies are also disclosed.

8 Claims, 6 Drawing Sheets

(56) References Cited

FOREIGN PATENT DOCUMENTS

| | | | |
|---|---|---|---|
| EP | 1196433 | B1 | 9/2006 |
| EP | 0843961 | B1 | 1/2007 |
| WO | 91/10741 | A1 | 7/1991 |
| WO | 92/03918 | A1 | 3/1992 |
| WO | 92/22645 | A1 | 12/1992 |
| WO | 92/22647 | A1 | 12/1992 |
| WO | 92/22670 | A1 | 12/1992 |
| WO | 93/11161 | A1 | 6/1993 |
| WO | 93/12227 | A1 | 6/1993 |
| WO | 94/00569 | A1 | 1/1994 |
| WO | 94/02602 | A1 | 2/1994 |
| WO | 94/13804 | A1 | 6/1994 |
| WO | 94/25585 | A1 | 11/1994 |
| WO | 96/14436 | A1 | 5/1996 |
| WO | 96/34096 | A1 | 10/1996 |
| WO | 97/13852 | A1 | 4/1997 |
| WO | 97/34631 | A1 | 9/1997 |
| WO | 98/24884 | A1 | 6/1998 |
| WO | 98/24893 | A2 | 6/1998 |
| WO | 99/07405 | A1 | 2/1999 |
| WO | 00/37487 | A1 | 6/2000 |
| WO | 00/76310 | A1 | 12/2000 |
| WO | 01/00660 | A1 | 1/2001 |
| WO | 02/060919 | A2 | 8/2002 |
| WO | 03/087340 | A2 | 10/2003 |
| WO | 03/100033 | A2 | 12/2003 |
| WO | 2008/112004 | A2 | 9/2008 |
| WO | 2009/040550 | A1 | 4/2009 |

OTHER PUBLICATIONS

Segal, David M. et al., 1974, "The Three-Dimensional Structure of a Phosphorylcholine-Binding Mouse Immunoglobulin Fab and the Nature of the Antigen Binding Site", Proc. Natl. Sci. USA, 71(11):4298-4302.

Sharon, Jacqueline, 1990, "Stuctural Characterization OfIdiotopes by Using Antibody Variants Generated by Site-Directed Mutagenesis", The Journal ofImmunology, 144:4863-4869.

Sharon, Jacqueline, 1990, "Structural correlates ofhigh antibody affinity: Three engineered amino acid substitutions can increase the affinity of an anti-p-azophenylarsonate antibody 200-fold", Proc. Natl. Acad. Sci, 87:4814-4817.

Sheppard, Dean, 2003, "Functions of Pulmonary Epithelial Integrins: From Development to Disease", Physiol Rev. 83:673-686.

Shull, Marcia M. et al., 1992, "Targeted disruption of the mouse transforming growth factor-1 gene results in multifocal inflammatory disease", Nature, 359:693-699.

Sipos, B. et al., 2004, "Immunohistochemical screening for 6-integrin subunit expression in adenocarcinomas using a novel monoclonal antibody reveals strong up-regulation in pancreatic ductal adenocarcinomas in vivo and in vitro", Histopathology, 45:226-236.

Smythe, W. Roy et al., 1995, "Integrin expression in non-small cell carcinoma of the lung", Cancer and Metastasis Reviews, 14:229-239.

Thomas, G.J., et al., 2006, "av 6 integrin in wound healing and cancer of the oral cavity", J. Oral Pathol. Med. 35:1-10.

Ward, E. Sally et al., 1989, "Binding activities of a repertoire of single immunoglobulin variable domains secreted from *Escherichia coli*", Nature, 341:544-546.

Weinreb, Paul H. et al., 2004, "Function-blocking Integrin av6 Monoclonal Antibodies", The Journal of Biological Chemistry, 279(17): 17875-17887.

Westernoff, Trent H. et al., 2005, "-6 Integrin, tenascin-C, and MMP-1 expression in salivary gland neoplasms", Oral Oncology, 41:170-174.

Wu, XH, et al., 2004, [Alphavbeta 6 integrin inhibits cisplatin-induced apoptosis in ovarian cancer cell lines], Zhonghua Fu Chan Ke Za Zhi, 39(2): 112-115. (English Abstract Only).

Xue, Hui et al., 2001, "Role of the av 6 Integrin in Human Oral Squamous Cell Carcinoma Growth in Vivo and in Vitro", Biochemical and Biophysical Research Communications, 288:610-618.

Zavadil, Jiri, 2005, "TGF- and epithelial-to-mesenchymal transitions", Oncogene, 24:5764-5774.

Agrez, Michael et al., 1994, "The av 6 Integrin Promotes Proliferation of Colon Carcinoma Cells through a Unique Region ofthe 6 Cytoplasmic Domain", The Journal of Cell Biology, 127(2):547-556.

Ahmed, Nuzhat et al., 2002, "av6 Integrin-A-Marker for the Malignant Potential of Epithelial Ovarian Cancer", The Journal of Histochemistry & Cytochemistry, 50(10):1371-1379.

Ahmed, N. et al., 2002, "Overexpression of av 6 integrin in serous epithelial ovarian cancer regulates extracellular matrix degradation via the plasminogen activation cascade", Carcinogenesis, 23(2):237-244.

Amit, A.G. et al., 1986, "Three-Dimensional Strncture of an Antigen-Antibody Complex at 2.8 A Resolution", Science, 233:747-753.

Annes, Justin P. et al., 2002, "The integrin av6 binds and activates latent TGF", FEBS Letters, 511:65-68.

Annes, Justin P. et al., 2004, "Integrin av6-mediated activation oflatent TGF- requires the latent TGF-binding protein-1", The Journal of Cell Biology, 165(5):723-734.

Babcook, JohnS. et al., 1996, "A novel strategy for generating monoclonal antibodies from single isolated lymphocytes producing antibodies of defined specificities", Proc. Natl. Acad. Sci. USA, 93:7843-7848.

Bates, Richard C. et al., 2005, "The Epithelial-Mesenchymal Transition (EMT) and Colorectal Cancer Progression", Cancer Biology & Therapy,4(4):365-370.

Bates, Richard C. et al., 2005, "Transcriptional activation ofintegrin 6 during the epithelial-mesenchymal transition defines a novel prognostic indicator of aggressive colon carcinoma", The Journal of Clinical Investigation, 115:339-347.

Bird, Robert E. et al., 1988, "Single-Chain Antigen-Binding Proteins", Science, 242:423-426.

Bowie, James U. et al., 1991, "A Method to Identify Protein Sequences That Fold into a Known Three-Dimensional Structure", Science, 253:164-170.

Breuss, J.M. et al., 1995, "Expression of the 6 integrin subunit in development, neoplasia and tissue repair suggests a role in epithelial remodeling", Journal of Cell Science, 108:2241-2251.

Busk, Michael et al., 1992, "Characterization ofthe Integrin av 6 as a Fibronectin-binding Protein", 267:5790-5796.

Casset, Florence et al., 2003, "A peptide mimetic of an anti-CD4 monoclonal antibody by rational design", Biochemical and Biophysical Research Communications, 307:198-205.

Caton, Andrew J. et al., 1990, "Identical D Region Sequences Expressed by Murine Monoclonal Antibodies Specific for a Human Tumor-Associated Antigen", The Journal ofImmunology, 144:1965-1968.

Chen, Yvonne et al., 1999, "Selection and Analysis of an Optimized Anti-VEGF Antibody: Crystal Structure of an Affinity-matured Fab in Complex with Antigen", Journal of Molecular Biology, 293:865-881.

Chothia, Cyrus et al., 1987, "Canonical Structures for the Hypervariable Regions of Immunoglobulins", J. Mol. Biol., 196:901-917.

Chothia, Cyrus et al., 1989, "Conformations of immunoglobulin hypervariable regions", 342:877-883.

De Pascalis, Roberto et al., 2002, "Grafting of"Abbreviated" Complementarity-Determining Regions Containing Specificity-Determining Residues Essential for Ligand Contact to Engineer a Less Immunogenic Humanized Monoclonal Antibody", The Journal of Immunology, 169:3076-3084.

Green, Larry L. et al., 1998, "Regulation ofB Cell Development by Variable Gene Complexity in Mice Reconstituted with Human Immunoglobulin Yeast Artificial Chromosomes", J. Exp. Med., 188:483-495.

Haapasalmi, Kirsi et al., 1996, "Keratinocytes in Human Wounds Express av 6 Integrin", J. Investigative Dermatology, 106:42-48.

Hakkinen, Lari et al., 2000, "Immunolocalization ofTenascin-C, a9 Integrin Subunit, and av 6 Integrin During Wound Healing in Human Oral Mucosa", The Journal of Histochemistry & Cytochemistry, 48(6):985-998.

Hamidi, S. et al., 2000, "Expression ofav6 integrin in oral leukoplakia", British Journal of Cancer, 82(8):1433-1440.

(56) References Cited

OTHER PUBLICATIONS

Holliger, Philipp et al., 1993, "Diabodies: Small bivalent and bispecific antibody fragments", Proc. Natl. Acad. Sci. USA, 90:6444-6448.
Holt, Lucy J. et al., 2003, "Domain antibodies: proteins for therapy", Trends in Biotechnology, 21(11):484-490.
Hu, Shi-zhen, et al., 1996, "Minibody: A Novel Engineered Anti-Carcinoembryonic Antigen Antibody Fragment (Single-Chain Fv-CH3) Which Exhibits Rapid, High-Level Targeting ofXenografts", Cancer Research, 56:3055-3061.
Huston, James S. et al., 1988, "Protein engineering of antibody binding sites: Recovery of specific activity in an anti-digoxin single-chain Fv analogue produced in *Escherichia coli*", Proc. Natl. Acad. Sci. USA, 85:5879-5883.
Internationl Search Report for PCT/US2007/075120 mailed Feb. 16, 2009.
Ishida, Isao et al., 2002, "Production of Human Monoclonal and Polyclonal Antibodies in TransChromo Animals", Cloning and Stem Cells, 4:91-102.
Janes, Sam M. et al., 2004, "Switch from av 5 to av 6 integrin expression protects squamous cell carcinomas from anoikis", The Journal of Cell Biology, 166:419-431.
Jones, Judith et al., 1997, "Changes in the expression of av integrins in oral squamous cell carcinomas", J. Oral Pathology, 26: 63-68.
Kabat, Elvin A. et al., 1991, "Identical V Region Aminco Acid Sequences and Segments of Sequences in Antibodies of Different Specificities", The Journal ofImmunology, 147:1709-1719.
Kawashima, Atsuhiro et al., 2003, "Expression of av Integrin Family in Gastric Carcinomas: Increased av 6 is Associated with Lymph Node Metastasis" Pathology Research and Practice, 199:57-64.
Keski-Oja, Jorma et al., 2004, "TGF-activation by traction?" Trends in Cell Biology, 14(12):657-659.
Koivisto, Leeni et al., 1999, "Different Integrins Mediate Cell Spreading, Haptotaxis and Lateral Migration ofHaCaT Keratinocytes on Fibronectin", Cell Adhesion and Communication, 7(3):245-257.
Lehmann, Maxime et al., 1994, "A Monoclonral Antibody Inhibits Adhesion to Fibronectin and Vitronectin of a Colon Carcinoma Cell Line and Recognizes the Integrins av3, av5, and av 61", Cancer Research, 54:2102-2107.
Leone, Brian, 2003, "Cellular, Molecular, and Tumor Biology 1: Cell Adhesion and Integrins", Proceedings ofthe American Association of Cancer Research, 44: p. 612, Abstract 4069.
Li, Xiaowu, et al, 2003, "av6-Fyn Signaling Promotes Oral Cancer Progression", The Journal of Biological Chemistry, 278(43):41646-41653.
Ludbrook, Steven B., et al., 2003, "The integrin av3 is a receptor for the latency-associated peptides oftransforming growth factors 1 and 3", Biochem. J., 369:311-318.
Ma, Li-Jun, et al. 2003, "Transforming Growth Factor-Dependent and -Independent Pathways of Induction ofTubulointerstitial Fibrosis in 6-/- Mice", American Journal ofPathology, 163(4):1261-1273.
MacCallum, Robert M. et al., 1996, "Antibody-antigen Interactions: Contact Analysis and Binding Site Topography", Journal of Molecular Biology, 262:732-745.
McCafferty, John et al., 1990, "Phage antibodies: filamentous phage displaying antibody variable domains", Nature, 348:552-554.
Mendez, Michael J. et al., 1997, "Functional transplant ofmegabase human immunoglobulin loci recapitulates human antibody response in mice", Nature Genetics, 15:146-156.
Morris, David G. et al., 2003, "Loss ofintegrin av 6-mediated TGF-activation causes Mmp12-dependent emphysema", Nature,422:169-173.
Munger, JohnS. et al., 1999, "The Integrin av 6 Binds and Activates Latent TGVBI: A Mechanism for Regulating Pulomnary Inflammation and Fibrosis", Cell, 96:319-328.
Pittet, Jean-Francois et al., 2001, "TGF—is a critical mediator of acute lung injury", J. Clin. Invest. 107:1537-1544.
Regezi, Joseph A. et al., 2002, "Tenascin and 6 integrin are overexpressed in floor of mouth in situ carcinomas and invasive squamous cell carcinomas", Oral Oncology, 38:332-336.
Reiter, Yoram, et al., 1996, "Engineering antibody Fv fragments for cancer detection and therapy: Disulfide-stablized Fv fragments", Nature Biotechnology, 14:1239-1245.
Rizo, Josep et al., 1992, "Constrained Peptides:Models of Bioactive Peptides and Protein Substructures", Annu. Rev. Biochem., 61:387-418.
Rudikoff, Stuart et al., 1982, "Single amino acid substitution altering antigen-binding specificity", Proc. Natl. Acad. Sci. USA, 79:1979-1983.

* cited by examiner

SEQUENCE LISTING

<160> NUMBER OF SEQ ID NOS: 97

<210> SEQ ID NO 1
<211> LENGTH: 366
<212> TYPE: DNA
<213> ORGANISM: Homo sapiens

<400> SEQUENCE: 1
caggtgcagc tgcaggagtc gggcccagga ctggtgaagc cttcacagac cctgtccctc 60
acctgcactg tcgctggtgg ctccatcaga agtggtgatt actactggag ctggatccgc 120
cagcacccag ggaagggcct ggagtggatt gggaacatct attacagtgg gagcacctac 180
tacaacccgt ccctcaagag tcgaattacc atttcagtag ccacgtctag gaaccagttc 240
tccctgaagc tgacctctgt gactgccgcg gacacggccg tgtattactg tgcgagaggg 300
ggagctatta cgatttttgg agtgtttgac tactggggcc agggaaccct ggtcaccgtc 360
tcctca 366

<210> SEQ ID NO 2
<211> LENGTH: 122
<212> TYPE: PRT
<213> ORGANISM: Homo sapiens

<400> SEQUENCE: 2

Gln Val Gln Leu Gln Glu Ser Gly Pro Gly Leu Val Lys Pro Ser Gln
1 5 10 15

Thr Leu Ser Leu Thr Cys Thr Val Ala Gly Gly Ser Ile Arg Ser Gly
20 25 30

Asp Tyr Tyr Trp Ser Trp Ile Arg Gln His Pro Gly Lys Gly Leu Glu
35 40 45

Trp Ile Gly Asn Ile Tyr Tyr Ser Gly Ser Thr Tyr Tyr Asn Pro Ser
50 55 60

Leu Lys Ser Arg Ile Thr Ile Ser Val Ala Thr Ser Arg Asn Gln Phe
65 70 75 80

Ser Leu Lys Leu Thr Ser Val Thr Ala Ala Asp Thr Ala Val Tyr Tyr
85 90 95

Cys Ala Arg Gly Gly Ala Ile Thr Ile Phe Gly Val Phe Asp Tyr Trp
100 105 110

Gly Gln Gly Thr Leu Val Thr Val Ser Ser
115 120

<210> SEQ ID NO 3
<211> LENGTH: 324
<212> TYPE: DNA
<213> ORGANISM: Homo sapiens

<400> SEQUENCE: 3
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccgtg cagttttggc 300
caggggacca agctggagat caaa 324

<210> SEQ ID NO 4
<211> LENGTH: 108

<212> TYPE: PRT
<213> ORGANISM: Homo sapiens

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Ser Phe Gly Gln Gly Thr Lys Leu Glu Ile Lys
            100                 105
```

<210> SEQ ID NO 5
<211> LENGTH: 366
<212> TYPE: DNA
<213> ORGANISM: Homo sapiens

<400> SEQUENCE: 5

```
gaggtgcagc tgttggagtc tgggggaggc ttggtacagc ctggggggtc cctgagactc     60

tcctgtgcag cctctggatt cacctttagc agctatgtca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaggtgtg    300

gatacagcta tggttaccta cggtatggac gtctggggcc aagggaccac ggtcaccgtc    360

tcctca                                                               366
```

<210> SEQ ID NO 6
<211> LENGTH: 122
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Asp Thr Ala Met Val Thr Tyr Gly Met Asp Val Trp
            100                 105                 110

Gly Gln Gly Thr Thr Val Thr Val Ser Ser
        115                 120
```

<210> SEQ ID NO 7
<211> LENGTH: 324
<212> TYPE: DNA
<213> ORGANISM: Homo sapiens

<400> SEQUENCE: 7
tcctatgagc tgacacagcc accctcggtg tcagtgtccc caggacaaac ggccaggatc 60
acctgctctg gagatgcatt gccaaaaaaa tatgcttatt ggtaccagca gaagtcaggc 120
caggcccctg tgctggtcat ctatgacgac agcaaacgac cctccgggat ccctgagaga 180
ttctctggct ccagctcagg gacaatggcc accttgacta tcagtggggc ccaggtggag 240
gatgaagctg actactactg ttactcaaca gacagcagtg gtaatcatag ggtgttcggc 300
ggagggacca agctgaccgt ccta 324

<210> SEQ ID NO 8
<211> LENGTH: 108
<212> TYPE: PRT
<213> ORGANISM: Homo sapiens

<400> SEQUENCE: 8

Ser Tyr Glu Leu Thr Gln Pro Pro Ser Val Ser Val Ser Pro Gly Gln
1 5 10 15

Thr Ala Arg Ile Thr Cys Ser Gly Asp Ala Leu Pro Lys Lys Tyr Ala
20 25 30

Tyr Trp Tyr Gln Gln Lys Ser Gly Gln Ala Pro Val Leu Val Ile Tyr
35 40 45

Asp Asp Ser Lys Arg Pro Ser Gly Ile Pro Glu Arg Phe Ser Gly Ser
50 55 60

Ser Ser Gly Thr Met Ala Thr Leu Thr Ile Ser Gly Ala Gln Val Glu
65 70 75 80

Asp Glu Ala Asp Tyr Tyr Cys Tyr Ser Thr Asp Ser Ser Gly Asn His
85 90 95

Arg Val Phe Gly Gly Gly Thr Lys Leu Thr Val Leu
100 105

<210> SEQ ID NO 9
<211> LENGTH: 369
<212> TYPE: DNA
<213> ORGANISM: Homo sapiens
<220> FEATURE:
<221> NAME/KEY: misc_feature
<222> LOCATION: (369)..(369)
<223> OTHER INFORMATION: n is a, c, g, or t

<400> SEQUENCE: 9
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcatcctc tcagccgaca agtccatcag caccgcctac 240
ctgcagtgga gcagcctgaa ggcctcggac accgccatgt attactgtgc gagacatgat 300
gaaagtagtg gttattacta tgtttttgat atctggggcc aagggacaat ggtcaccgtc 360 tcttcagcn 369

<210> SEQ ID NO 10
<211> LENGTH: 123

<212> TYPE: PRT
<213> ORGANISM: Homo sapiens

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Ile Leu Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Glu Ser Ser Gly Tyr Tyr Tyr Val Phe Asp Ile Trp
            100                 105                 110

Gly Gln Gly Thr Met Val Thr Val Ser Ser Ala
        115                 120

<210> SEQ ID NO 11
<211> LENGTH: 327
<212> TYPE: DNA
<213> ORGANISM: Homo sapiens
<220> FEATURE:
<221> NAME/KEY: misc_feature
<222> LOCATION: (300)..(300)
<223> OTHER INFORMATION: n is c or t

<400> SEQUENCE: 11
tcctatgagc tgacacaacc accctcggtg tcagtgtccc caggacaaac ggccaggatc     60
acctgctctg gagatgcatt gccaaaaaaa tatgcttatt ggtaccagca gaagtcaggc    120
caggcccctg ttctggtcat ctatgatgac atcaaacgac cctccgggat ccctgagaga    180
ttctctggct ccagctcagg gacaatggcc accttgacta tcagtggggc ccaggtggag    240
gatgaagctg actactactg ttactcaaca gacagcagtg gtaatcattg ggttttcttn    300
ggcggaggga ccaagctgac cgtccta                                        327

<210> SEQ ID NO 12
<211> LENGTH: 109
<212> TYPE: PRT
<213> ORGANISM: Homo sapiens

<400> SEQUENCE: 12

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ile Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

-continued

```
Trp Val Phe Phe Gly Gly Gly Thr Lys Leu Thr Val Leu
            100                 105


<210> SEQ ID NO 13
<211> LENGTH: 339
<212> TYPE: DNA
<213> ORGANISM: Homo sapiens

<400> SEQUENCE: 13

caggtgcagc tggtgcagtc tggggctgag gtgaagaagc ctggggcctc agtgaaggtc      60

tcctgcaagg cttctggata caccttcacc ggctactata tgcactgggt gcgacaggcc     120

cctggacaag ggcttgagtg gatgggatgg atcaacccta aaagtggtga cacaaactat     180

gcacagaagt ttcagggcag ggtcaccctg accagggaca cgtccaccag cacagcctac     240

atggagctga gcaggctgag atctgacgac acggccgtgt attactgtgc gagaaggttg     300

gacgtctggg gccaagggac cacggtcacc gtctcctca                             339


<210> SEQ ID NO 14
<211> LENGTH: 113
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Leu Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Leu Asp Val Trp Gly Gln Gly Thr Thr Val Thr Val Ser
            100                 105                 110

Ser


<210> SEQ ID NO 15
<211> LENGTH: 330
<212> TYPE: DNA
<213> ORGANISM: Homo sapiens

<400> SEQUENCE: 15

cagtctgtgt tgacgcagcc gccctcagtg tctgcggccc caggacagaa ggtcaccatc      60

tcctgctctg gaagcagctc caacattggg aataattatg tatcctggta ccagcagctc     120

ccaggaacag cccccaaact cctcatttat gacaataata agcgaccctc aggaattcct     180

gaccgattct ctggctccaa gtctggcacg tcagccaccc tgggcatcac cggactccag     240

actggggacg aggccgatta ttactgcgga acatggaata gcagcctgag tgctggttat     300

gtcttcggaa ctgggaccaa ggtcaccgtc                                       330


<210> SEQ ID NO 16
<211> LENGTH: 110
<212> TYPE: PRT
<213> ORGANISM: Homo sapiens
```

<400> SEQUENCE: 16

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asn
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asn Ser Ser Leu
85 90 95

Ser Ala Gly Tyr Val Phe Gly Thr Gly Thr Lys Val Thr Val
100 105 110

<210> SEQ ID NO 17
<211> LENGTH: 375
<212> TYPE: DNA
<213> ORGANISM: Homo sapiens
<220> FEATURE:
<221> NAME/KEY: misc_feature
<222> LOCATION: (375)..(375)
<223> OTHER INFORMATION: n is a, c, g, or t

<400> SEQUENCE: 17
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatat 180
agtccgtcct tccaaggcca ggtcaccatc tcagccgaca agtccatcag caccgcctac 240
ctgcagtgga gcagcctgaa ggcctcggac accgccatgt attactgtgc gagacatggt 300
atagcagcag ctggtttcta ctactactat atggacgtct ggggccaagg gaccacggtc 360
accgtctcct cagcn 375

<210> SEQ ID NO 18
<211> LENGTH: 125
<212> TYPE: PRT
<213> ORGANISM: Homo sapiens

<400> SEQUENCE: 18

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile Tyr Pro Gly Asp Ser Asp Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg His Gly Ile Ala Ala Ala Gly Phe Tyr Tyr Tyr Tyr Met Asp
100 105 110

```
Val Trp Gly Gln Gly Thr Thr Val Thr Val Ser Ser Ala
        115                 120                 125


<210> SEQ ID NO 19
<211> LENGTH: 327
<212> TYPE: DNA
<213> ORGANISM: Homo sapiens
<220> FEATURE:
<221> NAME/KEY: misc_feature
<222> LOCATION: (325)..(325)
<223> OTHER INFORMATION: n is a or c
<220> FEATURE:
<221> NAME/KEY: misc_feature
<222> LOCATION: (327)..(327)
<223> OTHER INFORMATION: n is a, c, g, or t

<400> SEQUENCE: 19

gaaattgtgt tgacgcagtc cccagacacc ctgtctttgt ctccagggga aagagcctcc      60

ctctcctgca gggccagtca gaatgttaac aggaactact tagtctggta ccagcagaaa     120

cctggccagg ctcccaggct cctcatctat ggtacatcca acagggccac tggcatccca     180

gacaggttca gtggcagtgg gtctgggaca gacttcactc tcaccatcag cagactggag     240

cctgaagatt ttgcagttta ttactgtcag cagtgtggta gtttaccatt cactttcggc     300

cctgggacca aagtggatat caaangn                                         327


<210> SEQ ID NO 20
<211> LENGTH: 109
<212> TYPE: PRT
<213> ORGANISM: Homo sapiens

<400> SEQUENCE: 20

Glu Ile Val Leu Thr Gln Ser Pro Asp Thr Leu Ser Leu Ser Pro Gly
1               5                   10                  15

Glu Arg Ala Ser Leu Ser Cys Arg Ala Ser Gln Asn Val Asn Arg Asn
            20                  25                  30

Tyr Leu Val Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Cys Gly Ser Leu Pro
                85                  90                  95

Phe Thr Phe Gly Pro Gly Thr Lys Val Asp Ile Lys Arg
            100                 105


<210> SEQ ID NO 21
<211> LENGTH: 372
<212> TYPE: DNA
<213> ORGANISM: Homo sapiens

<400> SEQUENCE: 21

caggtgcagc tgcaggagtc gggcccagga ctggtgaagc cttcacagac cctgtccctc      60

acctgcactg tctctggtgg ctccatcagc agtggtgttt actactggac ctggatccgc     120

cagcacccag ggaacggcct ggagtggatt ggctacatct attacagtgg gagcacctcc     180

tacaacccgt ccctcaagag tcgagttacc atatcagtag acacgtctaa gaaacagttc     240

tccctgaacc tgacctctgt gactgccgcg gacacggccg tgtattactg tgcgagagaa     300

ggaccactac ggggggacta ctactacggt ctggacgtct ggggccaagg gaccacggtc     360
```

accgtctcct ca 372

<210> SEQ ID NO 22
<211> LENGTH: 124
<212> TYPE: PRT
<213> ORGANISM: Homo sapiens

<400> SEQUENCE: 22

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Val Tyr Tyr Trp Thr Trp Ile Arg Gln His Pro Gly Asn Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Val Thr Ile Ser Val Asp Thr Ser Lys Lys Gln Phe
65                  70                  75                  80

Ser Leu Asn Leu Thr Ser Val Thr Ala Ala Asp Thr Ala Val Tyr Tyr
                85                  90                  95

Cys Ala Arg Glu Gly Pro Leu Arg Gly Asp Tyr Tyr Tyr Gly Leu Asp
            100                 105                 110

Val Trp Gly Gln Gly Thr Thr Val Thr Val Ser Ser
        115                 120
```

<210> SEQ ID NO 23
<211> LENGTH: 324
<212> TYPE: DNA
<213> ORGANISM: Homo sapiens

<400> SEQUENCE: 23

```
gaaattgtgt tgacgcagtc tccaggcacc ctgtctttgt ctccagggga aagagccacc     60

ctctcctgca gggccggtca gactattagc agtcgctact tagcctggta ccagcagaaa    120

cctggccagg ctcccaggcc cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gctcacctcg gacgttcggc    300

caagggacca aggtggaaat caaa                                           324
```

<210> SEQ ID NO 24
<211> LENGTH: 108
<212> TYPE: PRT
<213> ORGANISM: Homo sapiens

<400> SEQUENCE: 24

```
Glu Ile Val Leu Thr Gln Ser Pro Gly Thr Leu Ser Leu Ser Pro Gly
1               5                   10                  15

Glu Arg Ala Thr Leu Ser Cys Arg Ala Gly Gln Thr Ile Ser Ser Arg
            20                  25                  30

Tyr Leu Ala Trp Tyr Gln Gln Lys Pro Gly Gln Ala Pro Arg Pro Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

```
                85                  90                  95

Arg Thr Phe Gly Gln Gly Thr Lys Val Glu Ile Lys
            100                 105


<210> SEQ ID NO 25
<211> LENGTH: 384
<212> TYPE: DNA
<213> ORGANISM: Homo sapiens

<400> SEQUENCE: 25

caggtgcagc tgcaggagtc gggcccagga ctggtgaagc cttcacagac cctgtccctc     60

acctgcactg tctctggtgg ctccatcagc agtggtggtt actactggag ctggatccgc    120

cagcacccag ggaagggcct ggagtggatt gggtacatct attacagtgg gagcacctac    180

tacaacccgt ccctcaagag tcgagttacc atatcagtag acacgtctaa gaaccagttc    240

tccctgaagc tgagctctgt gactgccgcg gacacggcca tgtattactg tgcgagatat    300

cgaggaccag cggctgggcg gggagacttc tactacttcg gtatggacgt ctggggccaa    360

gggaccacgg tcaccgtctc ctca                                           384


<210> SEQ ID NO 26
<211> LENGTH: 128
<212> TYPE: PRT
<213> ORGANISM: Homo sapiens

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Met Tyr Tyr
                85                  90                  95

Cys Ala Arg Tyr Arg Gly Pro Ala Ala Gly Arg Gly Asp Phe Tyr Tyr
            100                 105                 110

Phe Gly Met Asp Val Trp Gly Gln Gly Thr Thr Val Thr Val Ser Ser
        115                 120                 125


<210> SEQ ID NO 27
<211> LENGTH: 339
<212> TYPE: DNA
<213> ORGANISM: Homo sapiens
<220> FEATURE:
<221> NAME/KEY: misc_feature
<222> LOCATION: (312)..(312)
<223> OTHER INFORMATION: n is c or t

<400> SEQUENCE: 27

gatattgtga tgacccagac tccactctct ctgtccgtca cccctggaca gccggcctcc     60

atcttctgca agtctagtca gagcctcctg aacagtgatg gaaagaccta tttgtgttgg    120

tacctgcaga agccaggcca gcctccacag ctcctgatct atgaagtttc caaccggttc    180

tctggagtgc cagataggtt cagtggcagc gggtcaggga cagatttcac actgaaaatc    240
```

-continued agccgggtgg aggctgagga tgttggggtt tattactgca tgcaaggtat acagcttccg 300
tgggcgttct tnggccaagg gaccaaggtg gaaatcaaa 339

<210> SEQ ID NO 28
<211> LENGTH: 113
<212> TYPE: PRT
<213> ORGANISM: Homo sapiens

<400> SEQUENCE: 28

Asp Ile Val Met Thr Gln Thr Pro Leu Ser Leu Ser Val Thr Pro Gly
1 5 10 15

Gln Pro Ala Ser Ile Phe Cys Lys Ser Ser Gln Ser Leu Leu Asn Ser
20 25 30

Asp Gly Lys Thr Tyr Leu Cys Trp Tyr Leu Gln Lys Pro Gly Gln Pro
35 40 45

Pro Gln Leu Leu Ile Tyr Glu Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Ile Gln Leu Pro Trp Ala Phe Phe Gly Gln Gly Thr Lys Val Glu Ile
100 105 110

Lys

<210> SEQ ID NO 29
<211> LENGTH: 383
<212> TYPE: DNA
<213> ORGANISM: Homo sapiens

<400> SEQUENCE: 29
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagaacctac 180
aacaacccgt ccctcaagag tcgagttacc atatcagtag acacgtctaa gaaccagttc 240
tccctgaagt tgagttctgt gactgccgcg gacacggccg tgtattactg tgcgagagtg 300
gctacgggga gaggggacta ccacttctac gctatggacg tctggggcca agggaccacg 360
gtcaccgtct cctcagcctc cac 383

<210> SEQ ID NO 30
<211> LENGTH: 125
<212> TYPE: PRT
<213> ORGANISM: Homo sapiens

<400> SEQUENCE: 30

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Arg Thr Tyr Asn Asn Pro Ser
50 55 60

Leu Lys Ser Arg Val Thr Ile Ser Val Asp Thr Ser Lys Asn Gln Phe
65 70 75 80

```
Ser Leu Lys Leu Ser Ser Val Thr Ala Ala Asp Thr Ala Val Tyr Tyr
                85                  90                  95

Cys Ala Arg Val Ala Thr Gly Arg Gly Asp Tyr His Phe Tyr Ala Met
            100                 105                 110

Asp Val Trp Gly Gln Gly Thr Thr Val Thr Val Ser Ser
        115                 120                 125


<210> SEQ ID NO 31
<211> LENGTH: 318
<212> TYPE: DNA
<213> ORGANISM: Homo sapiens

<400> SEQUENCE: 31

tcctatgagc tgacacagcc atcctcagtg tcagtgtctc cgggacagac agccaggatc      60

acctgctcag gagatgtact ggcaaaaaag tctgctcggt ggttccacca gaagccaggc     120

caggcccctg tactggtgat ttataaagac agtgagcggc cctcagggat ccctgagcgc     180

ttctccggct ccagctcagg gaccacagtc accttgacca tcagcggggc ccaggttgag     240

gatgaggctg cctattactg ttactctgcg gctgacaaca atctggtatt cggcggaggg     300

accaagctga ccgtccta                                                  318


<210> SEQ ID NO 32
<211> LENGTH: 106
<212> TYPE: PRT
<213> ORGANISM: Homo sapiens

<400> SEQUENCE: 32

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Ser Ala
            20                  25                  30

Arg Trp Phe His Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Ala Tyr Tyr Cys Tyr Ser Ala Ala Asp Asn Asn Leu Val
                85                  90                  95

Phe Gly Gly Gly Thr Lys Leu Thr Val Leu
            100                 105


<210> SEQ ID NO 33
<211> LENGTH: 354
<212> TYPE: DNA
<213> ORGANISM: Homo sapiens

<400> SEQUENCE: 33

gaggtgcagc tggtgcagtc tggagcagag gtgaaaaagc ccggggagtc tctgaagatc      60

tcctgtaagg gttctggata cagctttccc agctactgga tcggctgggt gcgccagatg     120

cccgggaagg gcctggagtg gatggggatc atctatcctg gtgactctga taccagatac     180

agcccgtcct tccaaggcca ggtcaccatc tcagctgaca agtccatcag caccgcctac     240

ctgcagtgga gcagcctgaa ggcctcggac accgccatgt attactgtgc gagacaccct     300

atggaggacg gtatggacgt ctggggccaa gggaccacgg tcaccgtctc ctca          354
```

<210> SEQ ID NO 34
<211> LENGTH: 118
<212> TYPE: PRT
<213> ORGANISM: Homo sapiens

<400> SEQUENCE: 34

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Pro Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Pro Met Glu Asp Gly Met Asp Val Trp Gly Gln Gly Thr
            100                 105                 110

Thr Val Thr Val Ser Ser
        115
```

<210> SEQ ID NO 35
<211> LENGTH: 321
<212> TYPE: DNA
<213> ORGANISM: Homo sapiens

<400> SEQUENCE: 35

```
tcctatgagc tgacacagcc accctcggtg tcagtgtccc caggacaaac ggccaggatc     60

acctgctctg gagatgcttt gccaaaaaaa tatgcttttt ggtaccagca gaagtcaggc    120

caggcccctg tgctggtcat ctatgacgac aacaaacgac cctccgggat ccctgagaga    180

ttctctggct ccagctcagg gacaatggcc accttgacta tcactggggc ccaggtggag    240

gatgaagctg actactactg ttactcaaca gacagcagtg gtcatcatgt attcggcgga    300

gggaccaagc tgaccgtcct a                                               321
```

<210> SEQ ID NO 36
<211> LENGTH: 107
<212> TYPE: PRT
<213> ORGANISM: Homo sapiens

<400> SEQUENCE: 36

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Phe Trp Tyr Gln Gln Lys Ser Gly Gln Ala Pro Val Leu Val Ile Tyr
        35                  40                  45

Asp Asp Asn Lys Arg Pro Ser Gly Ile Pro Glu Arg Phe Ser Gly Ser
    50                  55                  60

Ser Ser Gly Thr Met Ala Thr Leu Thr Ile Thr Gly Ala Gln Val Glu
65                  70                  75                  80

Asp Glu Ala Asp Tyr Tyr Cys Tyr Ser Thr Asp Ser Ser Gly His His
                85                  90                  95

Val Phe Gly Gly Gly Thr Lys Leu Thr Val Leu
```

100 105

<210> SEQ ID NO 37
<211> LENGTH: 375
<212> TYPE: DNA
<213> ORGANISM: Homo sapiens

<400> SEQUENCE: 37
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg gtggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagagatctg 300
gcagctcgtc gggggggacta ctactactac ggtatggacg tctggggcca agggaccacg 360
gtcaccgtct cctca 375

<210> SEQ ID NO 38
<211> LENGTH: 125
<212> TYPE: PRT
<213> ORGANISM: Homo sapiens

<400> SEQUENCE: 38

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Gly Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Leu Ala Ala Arg Arg Gly Asp Tyr Tyr Tyr Tyr Gly Met
100 105 110

Asp Val Trp Gly Gln Gly Thr Thr Val Thr Val Ser Ser
115 120 125

<210> SEQ ID NO 39
<211> LENGTH: 321
<212> TYPE: DNA
<213> ORGANISM: Homo sapiens

<400> SEQUENCE: 39
tcttctgagc tgactcagga ccctgttgtg tctgtggcct tgggacagac agtcaggatc 60
acttgccaag gcgacagcct cagaagctat tatttaagct ggtaccagca gaagccagga 120
caggcccctg tacttgtcat ctatggtaaa aacaaccggc cctcagggat cccagaccga 180
ttctctggct ccaactcagg aaacacagct tccttgacca tcactggggc tcaggcggaa 240
gatgaggctg actattactg taattcccgg gacagcagtg gtaaccatct gttcggcgga 300
gggaccaagc tgaccgtcct a 321

<210> SEQ ID NO 40
<211> LENGTH: 107

<212> TYPE: PRT
<213> ORGANISM: Homo sapiens

<400> SEQUENCE: 40

```
Ser Ser Glu Leu Thr Gln Asp Pro Val Val Ser Val Ala Leu Gly Gln
1               5                   10                  15

Thr Val Arg Ile Thr Cys Gln Gly Asp Ser Leu Arg Ser Tyr Tyr Leu
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Asn Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Phe Gly Gly Gly Thr Lys Leu Thr Val Leu
            100                 105
```

<210> SEQ ID NO 41
<211> LENGTH: 375
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is c or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (105)..(105)
<223> OTHER INFORMATION: n is c or t
<220> FEATURE:
<221> NAME/KEY: misc_feature
<222> LOCATION: (300)..(300)
<223> OTHER INFORMATION: n is a, c, g, or t

<400> SEQUENCE: 41

```
gaggtgcagc tggtggagtc tgggggaggc ctggtcaagc ctgggggtc cctgagactc     60

tcctgtgcag cctctggata naccttcacn aactatatca tgcantgggt ccgccaggct    120

ccagggaagg ggctggagtg ggtctcatcc attagtatta gtagtagtta catatactac    180

gcagactcag tgaagggccg attcaccatc tccagagaca acgccaagaa ctcactgtat    240

ctgcaaatga acagcctgag agccgaggac acggctgtgt attactgtgc gagagatccn    300

gtaccactgg aacgacgcga ctactactac ggtatggacg tctggggcca agggaccacg    360

gtcaccgtct cctca                                                     375
```

<210> SEQ ID NO 42
<211> LENGTH: 125
<212> TYPE: PRT
<213> ORGANISM: Homo sapiens

<400> SEQUENCE: 42

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asn Tyr
            20                  25                  30

Ile Met His Trp Val Arg Gln Ala Pro Gly Lys Gly Leu Glu Trp Val
```

-continued

```
        35                  40                  45

Ser Ser Ile Ser Ile Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Val Pro Leu Glu Arg Arg Asp Tyr Tyr Tyr Gly Met
            100                 105                 110

Asp Val Trp Gly Gln Gly Thr Thr Val Thr Val Ser Ser
        115                 120                 125


<210> SEQ ID NO 43
<211> LENGTH: 330
<212> TYPE: DNA
<213> ORGANISM: Homo sapiens

<400> SEQUENCE: 43

cagtctgtgt tgacgcagcc gccctcaatg tctgcggccc caggacagaa ggtcaccatc      60

tcctgctctg gaagcagctc caacattggg aataattatg tatcctggta ccagcagctc     120

ccaggaacag cccccaaact cctcatttat gacaataata agcgaccctc agggattcct     180

gaccgattct ctggctccaa gtctggcacg tcagccaccc tgggcatcac cggactccag     240

actggggacg aggccgatta ttactgcgga acatgggata gcagcctgag cgctggggta     300

ttcggcggag ggaccaagct gaccgtccta                                      330


<210> SEQ ID NO 44
<211> LENGTH: 110
<212> TYPE: PRT
<213> ORGANISM: Homo sapiens

<400> SEQUENCE: 44

Gln Ser Val Leu Thr Gln Pro Pro Ser Met Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110


<210> SEQ ID NO 45
<211> LENGTH: 375
<212> TYPE: DNA
<213> ORGANISM: Homo sapiens

<400> SEQUENCE: 45

caggtgcagc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcagtt atatggtatg atggaagtaa taaatactac     180
```

```
gcagactccg tgaagggccg attcaccatc tccagagaca attccaagaa cacgctgtat    240

ctgcaaatga acagcctgag agccgaggac acggctgtgt attactgtgc gagaacggag    300

ggtatagcag ctcgtctcta ctactactac ggtatggacg tctggggcca agggaccacg    360

gtcaccgtct cctca                                                     375


<210> SEQ ID NO 46
<211> LENGTH: 125
<212> TYPE: PRT
<213> ORGANISM: Homo sapiens

<400> SEQUENCE: 46

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Glu Gly Ile Ala Ala Arg Leu Tyr Tyr Tyr Tyr Gly Met
            100                 105                 110

Asp Val Trp Gly Gln Gly Thr Thr Val Thr Val Ser Ser
        115                 120                 125


<210> SEQ ID NO 47
<211> LENGTH: 324
<212> TYPE: DNA
<213> ORGANISM: Homo sapiens

<400> SEQUENCE: 47

gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat ggtgcatcca gcagggccac tgacatccca    180

gacaggttca gtggcagtgg gtctgggaca gacttcactc tcaccatcag cagactggag    240

cctgaagatt ttgcagtgta ttactgtcag cagtatggta gctcaccgtg gacgttcggc    300

caagggacca aggtggaaat caaa                                           324


<210> SEQ ID NO 48
<211> LENGTH: 108
<212> TYPE: PRT
<213> ORGANISM: Homo sapiens

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Asp Ile Pro Asp Arg Phe Ser
```

```
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 49
<211> LENGTH: 111
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Leu Trp Gly Gln Gly Thr Thr Val Thr Val Ser Ser
            100                 105                 110


<210> SEQ ID NO 50
<211> LENGTH: 123
<212> TYPE: PRT
<213> ORGANISM: Homo sapiens

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gln Leu Glu Arg Tyr Tyr Tyr Tyr Tyr Gly Met Asp Val
            100                 105                 110

Trp Gly Gln Gly Thr Thr Val Thr Val Ser Ser
        115                 120


<210> SEQ ID NO 51
<211> LENGTH: 121
<212> TYPE: PRT
<213> ORGANISM: Homo sapiens

<400> SEQUENCE: 51
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Asp Thr Ala Met Val Tyr Tyr Gly Met Asp Val Trp Gly
            100                 105                 110

Gln Gly Thr Thr Val Thr Val Ser Ser
        115                 120


<210> SEQ ID NO 52
<211> LENGTH: 122
<212> TYPE: PRT
<213> ORGANISM: Homo sapiens

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Ala Ala Arg Tyr Tyr Tyr Tyr Tyr Gly Met Asp Val Trp
            100                 105                 110

Gly Gln Gly Thr Thr Val Thr Val Ser Ser
        115                 120


<210> SEQ ID NO 53
<211> LENGTH: 125
<212> TYPE: PRT
<213> ORGANISM: Homo sapiens

<400> SEQUENCE: 53

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
                85                  90                  95

Cys Ala Arg Gly Ile Ala Ala Ala Gly Tyr Tyr Tyr Tyr Tyr Gly Met
            100                 105                 110

Asp Val Trp Gly Gln Gly Thr Thr Val Thr Val Ser Ser
        115                 120                 125
```

```
<210> SEQ ID NO 54
<211> LENGTH: 119
<212> TYPE: PRT
<213> ORGANISM: Homo sapiens

<400> SEQUENCE: 54

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ile Thr Ile Phe Gly Val Phe Asp Tyr Trp Gly Gln Gly
            100                 105                 110

Thr Leu Val Thr Val Ser Ser
        115
```

```
<210> SEQ ID NO 55
<211> LENGTH: 122
<212> TYPE: PRT
<213> ORGANISM: Homo sapiens

<400> SEQUENCE: 55

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Ala Thr Tyr Tyr Tyr Tyr Tyr Gly Met Asp Val Trp
            100                 105                 110

Gly Gln Gly Thr Thr Val Thr Val Ser Ser
        115                 120
```

```
<210> SEQ ID NO 56
<211> LENGTH: 121
<212> TYPE: PRT
<213> ORGANISM: Homo sapiens
```

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Tyr Tyr Tyr Tyr Tyr Gly Met Asp Val Trp Gly
            100                 105                 110

Gln Gly Thr Thr Val Thr Val Ser Ser
        115                 120

<210> SEQ ID NO 57
<211> LENGTH: 120
<212> TYPE: PRT
<213> ORGANISM: Homo sapiens

<400> SEQUENCE: 57

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Ser Gly Tyr Tyr Tyr Ala Phe Asp Ile Trp Gly Gln Gly
            100                 105                 110

Thr Met Val Thr Val Ser Ser Ala
        115                 120

<210> SEQ ID NO 58
<211> LENGTH: 113
<212> TYPE: PRT
<213> ORGANISM: Homo sapiens

<400> SEQUENCE: 58

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Met Asp Val Trp Gly Gln Gly Thr Thr Val Thr Val Ser
            100                 105                 110

Ser


<210> SEQ ID NO 59
<211> LENGTH: 123
<212> TYPE: PRT
<213> ORGANISM: Homo sapiens

<400> SEQUENCE: 59

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ile Ala Ala Ala Gly Tyr Tyr Tyr Gly Met Asp Val Trp
            100                 105                 110

Gly Lys Gly Thr Thr Val Thr Val Ser Ser Ala
        115                 120


<210> SEQ ID NO 60
<211> LENGTH: 112
<212> TYPE: PRT
<213> ORGANISM: Homo sapiens

<400> SEQUENCE: 60

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Trp Thr Phe Gly Gln Gly Thr Lys Val Glu Ile Lys
            100                 105                 110


<210> SEQ ID NO 61
<211> LENGTH: 108
<212> TYPE: PRT
<213> ORGANISM: Homo sapiens

<400> SEQUENCE: 61
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 62
<211> LENGTH: 108
<212> TYPE: PRT
<213> ORGANISM: Homo sapiens

<400> SEQUENCE: 62

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105


<210> SEQ ID NO 63
<211> LENGTH: 109
<212> TYPE: PRT
<213> ORGANISM: Homo sapiens

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg
            100                 105
```

<210> SEQ ID NO 64
<211> LENGTH: 109
<212> TYPE: PRT
<213> ORGANISM: Homo sapiens

<400> SEQUENCE: 64

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Tyr Val Phe Gly Thr Gly Thr Lys Val Thr Val
            100                 105
```

<210> SEQ ID NO 65
<211> LENGTH: 110
<212> TYPE: PRT
<213> ORGANISM: Homo sapiens

<400> SEQUENCE: 65

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110
```

<210> SEQ ID NO 66
<211> LENGTH: 108
<212> TYPE: PRT
<213> ORGANISM: Homo sapiens

<400> SEQUENCE: 66

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60
```

```
Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Val Val Phe Gly Gly Gly Thr Lys Leu Thr Val Leu
            100                 105


<210> SEQ ID NO 67
<211> LENGTH: 108
<212> TYPE: PRT
<213> ORGANISM: Homo sapiens

<400> SEQUENCE: 67

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Val Val Phe Gly Gly Gly Thr Lys Leu Thr Val Leu
            100                 105


<210> SEQ ID NO 68
<211> LENGTH: 108
<212> TYPE: PRT
<213> ORGANISM: Homo sapiens

<400> SEQUENCE: 68

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105


<210> SEQ ID NO 69
<211> LENGTH: 106
<212> TYPE: PRT
<213> ORGANISM: Homo sapiens

<400> SEQUENCE: 69

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
```

```
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Val Val
                85                  90                  95

Phe Gly Gly Gly Thr Lys Leu Thr Val Leu
            100                 105
```

<210> SEQ ID NO 70
<211> LENGTH: 372
<212> TYPE: DNA
<213> ORGANISM: Homo sapiens

<400> SEQUENCE: 70

```
caggtgcagc tgcaggagtc gggcccagga ctggtgaagc cttcacagac cctgtccctc     60

acctgcactg tctctggtgg ctccatcagc agtggtgttt actactggac ctggatccgc    120

cagcacccag ggaacggcct ggagtggatt ggctacatct attacagtgg gagcacctcc    180

tacaacccgt ccctcaagag tcgagttacc atatcagtag acacgtctaa gaaacagttc    240

tccctgaagc tgacctctgt gactgccgcg gacacggccg tgtattactg tgcgagagaa    300

ggaccactac gggggacta ctactacggt ctggacgtct ggggccaagg gaccacggtc    360

accgtctcct ca                                                        372
```

<210> SEQ ID NO 71
<211> LENGTH: 124
<212> TYPE: PRT
<213> ORGANISM: Homo sapiens

<400> SEQUENCE: 71

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Val Tyr Tyr Trp Thr Trp Ile Arg Gln His Pro Gly Asn Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Val Thr Ile Ser Val Asp Thr Ser Lys Lys Gln Phe
65                  70                  75                  80

Ser Leu Lys Leu Thr Ser Val Thr Ala Ala Asp Thr Ala Val Tyr Tyr
                85                  90                  95

Cys Ala Arg Glu Gly Pro Leu Arg Gly Asp Tyr Tyr Tyr Gly Leu Asp
            100                 105                 110

Val Trp Gly Gln Gly Thr Thr Val Thr Val Ser Ser
        115                 120
```

<210> SEQ ID NO 72
<211> LENGTH: 324
<212> TYPE: DNA
<213> ORGANISM: Homo sapiens

<400> SEQUENCE: 72
gaaattgtgt tgacgcagtc tccaggcacc ctgtctttgt ctccagggga aagagccacc 60
ctctcctgca gggccggtca gactattagc agtcgctact tagcctggta ccagcagaaa 120
cctggccagg ctcccaggcc cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacctcg gacgttcggc 300
caagggacca aggtggaaat caaa 324

<210> SEQ ID NO 73
<211> LENGTH: 108
<212> TYPE: PRT
<213> ORGANISM: Homo sapiens

<400> SEQUENCE: 73

Glu Ile Val Leu Thr Gln Ser Pro Gly Thr Leu Ser Leu Ser Pro Gly
1 5 10 15

Glu Arg Ala Thr Leu Ser Cys Arg Ala Gly Gln Thr Ile Ser Ser Arg
20 25 30

Tyr Leu Ala Trp Tyr Gln Gln Lys Pro Gly Gln Ala Pro Arg Pro Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Arg Thr Phe Gly Gln Gly Thr Lys Val Glu Ile Lys
100 105

<210> SEQ ID NO 74
<211> LENGTH: 375
<212> TYPE: DNA
<213> ORGANISM: Homo sapiens

<400> SEQUENCE: 74
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagaacctac 180
aacaacccgt ccctcaagag tcgagttacc atatcagtag acacgtctaa gaaccagttc 240
tccctgaagt tgagttctgt gactgccgcg gacacggccg tgtattactg tgcgagagtg 300
gctacgggga gagcggacta ccacttctac gctatggacg tctggggcca agggaccacg 360
gtcaccgtct cctca 375

<210> SEQ ID NO 75
<211> LENGTH: 125
<212> TYPE: PRT
<213> ORGANISM: Homo sapiens

<400> SEQUENCE: 75

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

```
Trp Ile Gly Tyr Ile Tyr Tyr Ser Gly Arg Thr Tyr Asn Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Ala Thr Gly Arg Ala Asp Tyr His Phe Tyr Ala Met
            100                 105                 110

Asp Val Trp Gly Gln Gly Thr Thr Val Thr Val Ser Ser
        115                 120                 125
```

<210> SEQ ID NO 76
<211> LENGTH: 318
<212> TYPE: DNA
<213> ORGANISM: Homo sapiens

<400> SEQUENCE: 76

```
tcctatgagc tgacacagcc atcctcagtg tcagtgtctc cgggacagac agccaggatc     60

acctgctcag gagatgtact ggcaaaaaag tctgctcggt ggttccacca gaagccaggc    120

caggcccctg tactggtgat ttataaagac agtgagcggc cctcagggat ccctgagcgc    180

ttctccggct ccagctcagg gaccacagtc accttgacca tcagcggggc ccaggttgag    240

gatgaggctg cctattactg ttactctgcg gctgacaaca atctggtatt cggcggaggg    300

accaagctga ccgtccta                                                  318
```

<210> SEQ ID NO 77
<211> LENGTH: 106
<212> TYPE: PRT
<213> ORGANISM: Homo sapiens

<400> SEQUENCE: 77

```
Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Ser Ala
            20                  25                  30

Arg Trp Phe His Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Ala Tyr Tyr Cys Tyr Ser Ala Ala Asp Asn Asn Leu Val
                85                  90                  95

Phe Gly Gly Gly Thr Lys Leu Thr Val Leu
            100                 105
```

<210> SEQ ID NO 78
<211> LENGTH: 339
<212> TYPE: DNA
<213> ORGANISM: Homo sapiens

<400> SEQUENCE: 78

```
caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatgggatgg atcaacccta aaagtggtga cacaaactat    180
```

```
gcacagaagt ttcagggcag ggtcaccatg accagggaca cgtccaccag cacagcctac    240

atggagctga gcaggctgag atctgacgac acggccgtgt attactgtgc gagaaggttg    300

gacgtctggg gccaagggac cacggtcacc gtctcctca                           339


<210> SEQ ID NO 79
<211> LENGTH: 113
<212> TYPE: PRT
<213> ORGANISM: Homo sapiens

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Leu Asp Val Trp Gly Gln Gly Thr Thr Val Thr Val Ser
            100                 105                 110

Ser


<210> SEQ ID NO 80
<211> LENGTH: 333
<212> TYPE: DNA
<213> ORGANISM: Homo sapiens

<400> SEQUENCE: 80

cagtctgtgt tgacgcagcc gccctcagtg tctgcggccc caggacagaa ggtcaccatc     60

tcctgctctg gaagcagctc caacattggg aataattatg tatcctggta ccagcagctc    120

ccaggaacag cccccaaact cctcatttat gacaataata agcgaccctc aggaattcct    180

gaccgattct ctggctccaa gtctggcacg tcagccaccc tgggcatcac cggactccag    240

actggggacg aggccgatta ttactgcgga acatggaata gcagcctgag tgctggttat    300

gtcttcggaa ctgggaccaa ggtcaccgtc cta                                 333


<210> SEQ ID NO 81
<211> LENGTH: 111
<212> TYPE: PRT
<213> ORGANISM: Homo sapiens

<400> SEQUENCE: 81

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80
```

```
Thr Gly Asp Glu Ala Asp Tyr Tyr Cys Gly Thr Trp Asn Ser Ser Leu
                85                  90                  95

Ser Ala Gly Tyr Val Phe Gly Thr Gly Thr Lys Val Thr Val Leu
            100                 105                 110


<210> SEQ ID NO 82
<211> LENGTH: 339
<212> TYPE: DNA
<213> ORGANISM: Homo sapiens

<400> SEQUENCE: 82

caggtgcagc tggtgcagtc tggggctgag gtgaagaagc ctggggcctc agtgaaggtc      60

tcctgcaagg cttctggata caccttcacc ggctactata tgcactgggt gcgacaggcc     120

cctggacaag ggcttgagtg gatgggatgg atcaacccta aaagtggtga cacaaactat     180

gcacagaagt ttcagggcag ggtcaccctg accagggaca cgtccaccag cacagcctac     240

atggagctga gcaggctgag atctgacgac acggccgtgt attactgtgc gagaaggttg     300

gacgtctggg gccaagggac cacggtcacc gtctcctca                            339


<210> SEQ ID NO 83
<211> LENGTH: 113
<212> TYPE: PRT
<213> ORGANISM: Homo sapiens

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Leu Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Leu Asp Val Trp Gly Gln Gly Thr Thr Val Thr Val Ser
            100                 105                 110

Ser


<210> SEQ ID NO 84
<211> LENGTH: 333
<212> TYPE: DNA
<213> ORGANISM: Homo sapiens

<400> SEQUENCE: 84

cagtctgtgt tgacgcagcc gccctcagtg tctgcggccc caggacagaa ggtcaccatc      60

tcctgctctg gaagcagctc caacattggg aataattatg tatcctggta ccagcagctc     120

ccaggaacag cccccaaact cctcatttat gacaataata agcgaccctc aggaattcct     180

gaccgattct ctggctccaa gtctggcacg tcagccaccc tgggcatcac cggactccag     240

actggggacg aggccgatta ttactgcgga acatgggata gcagcctgag tgctggttat     300

gtcttcggaa ctgggaccaa ggtcaccgtc cta                                  333
```

<210> SEQ ID NO 85
<211> LENGTH: 111
<212> TYPE: PRT
<213> ORGANISM: Homo sapiens

<400> SEQUENCE: 85

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Tyr Val Phe Gly Thr Gly Thr Lys Val Thr Val Leu
            100                 105                 110
```

<210> SEQ ID NO 86
<211> LENGTH: 339
<212> TYPE: DNA
<213> ORGANISM: Homo sapiens

<400> SEQUENCE: 86

```
caggtgcagc tggtgcagtc tggggctgag gtgaagaagc ctggggcctc agtgaaggtc     60

tcctgcaagg cttctggata caccttcacc ggctactata tgcactgggt gcgacaggcc    120

cctggacaag ggcttgagtg gatgggatgg atcaacccta aaagtggtga cacaaactat    180

gcacagaagt ttcagggcag ggtcaccatg accagggaca cgtccaccag cacagcctac    240

atggagctga gcaggctgag atctgacgac acggccgtgt attactgtgc gagaaggttg    300

gacgtctggg gccaagggac cacggtcacc gtctcctca                           339
```

<210> SEQ ID NO 87
<211> LENGTH: 113
<212> TYPE: PRT
<213> ORGANISM: Homo sapiens

<400> SEQUENCE: 87

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Asp Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Leu Asp Val Trp Gly Gln Gly Thr Thr Val Thr Val Ser
            100                 105                 110

Ser
```

-continued

<210> SEQ ID NO 88
<211> LENGTH: 333
<212> TYPE: DNA
<213> ORGANISM: Homo sapiens

<400> SEQUENCE: 88

```
cagtctgtgt tgacgcagcc gccctcagtg tctgcggccc caggacagaa ggtcaccatc     60

tcctgctctg gaagcagctc caacattggg aataattatg tatcctggta ccagcagctc    120

ccaggaacag cccccaaact cctcatttat gacaataata agcgaccctc aggaattcct    180

gaccgattct ctggctccaa gtctggcacg tcagccaccc tgggcatcac cggactccag    240

actggggacg aggccgatta ttactgcgga acatgggata gcagcctgag tgctggttat    300

gtcttcggaa ctgggaccaa ggtcaccgtc cta                                 333
```

<210> SEQ ID NO 89
<211> LENGTH: 111
<212> TYPE: PRT
<213> ORGANISM: Homo sapiens

<400> SEQUENCE: 89

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Tyr Val Phe Gly Thr Gly Thr Lys Val Thr Val Leu
            100                 105                 110
```

<210> SEQ ID NO 90
<211> LENGTH: 383
<212> TYPE: DNA
<213> ORGANISM: Homo sapiens

<400> SEQUENCE: 90

```
caggtgcagc tgcaggagtc gggcccagga ctggtgaagc cttcacagac cctgtccctc     60

acctgcactg tctctggtgg ctccatcagc agtggtggtt actactggag ctggatccgc    120

cagcacccag ggaagggcct ggagtggatt gggtacatct attacagtgg gagaacctac    180

aacaacccgt ccctcaagag tcgagttacc atatcagtag acacgtctaa gaaccagttc    240

tccctgaagt tgagttctgt gactgccgcg gacacggccg tgtattactg tgcgagagtg    300

gctacgggga gaggggacta ccacttctac gctatggacg tctggggcca agggaccacg    360

gtcaccgtct cctcagcctc cac                                            383
```

<210> SEQ ID NO 91
<211> LENGTH: 125
<212> TYPE: PRT
<213> ORGANISM: Homo sapiens

<400> SEQUENCE: 91

-continued

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Ser Trp Ile Arg Gln His Pro Gly Lys Gly Leu Glu
35 40 45

Trp Ile Gly Tyr Ile Tyr Tyr Ser Gly Arg Thr Tyr Asn Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Val Ala Thr Gly Arg Gly Asp Tyr His Phe Tyr Ala Met
100 105 110

Asp Val Trp Gly Gln Gly Thr Thr Val Thr Val Ser Ser
115 120 125

<210> SEQ ID NO 92
<211> LENGTH: 318
<212> TYPE: DNA
<213> ORGANISM: Homo sapiens

<400> SEQUENCE: 92
tcctatgagc tgacacagcc atcctcagtg tcagtgtctc cgggacagac agccaggatc 60
acctgctcag gagatgtact ggcaaaaaag tctgctcggt ggttccacca gaagccaggc 120
caggcccctg tactggtgat ttataaagac agtgagcggc cctcagggat ccctgagcgc 180
ttctccggct ccagctcagg gaccacagtc accttgacca tcagcggggc ccaggttgag 240
gatgaggctg actattactg ttactctgcg gctgacaaca atctggtatt cggcggaggg 300
accaagctga ccgtccta 318

<210> SEQ ID NO 93
<211> LENGTH: 106
<212> TYPE: PRT
<213> ORGANISM: Homo sapiens

<400> SEQUENCE: 93

Ser Tyr Glu Leu Thr Gln Pro Ser Ser Val Ser Val Ser Pro Gly Gln
1 5 10 15

Thr Ala Arg Ile Thr Cys Ser Gly Asp Val Leu Ala Lys Lys Ser Ala
20 25 30

Arg Trp Phe His Gln Lys Pro Gly Gln Ala Pro Val Leu Val Ile Tyr
35 40 45

Lys Asp Ser Glu Arg Pro Ser Gly Ile Pro Glu Arg Phe Ser Gly Ser
50 55 60

Ser Ser Gly Thr Thr Val Thr Leu Thr Ile Ser Gly Ala Gln Val Glu
65 70 75 80

Asp Glu Ala Asp Tyr Tyr Cys Tyr Ser Ala Ala Asp Asn Asn Leu Val
85 90 95

Phe Gly Gly Gly Thr Lys Leu Thr Val Leu
100 105

<210> SEQ ID NO 94
<211> LENGTH: 375
<212> TYPE: DNA
<213> ORGANISM: Homo sapiens

<400> SEQUENCE: 94
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagaacctac 180
aacaacccgt ccctcaagag tcgagttacc atatcagtag acacgtctaa gaaccagttc 240
tccctgaagt tgagttctgt gactgccgcg gacacggccg tgtattactg tgcgagagtg 300
gctacgggga gagcggacta ccacttctac gctatggacg tctggggcca agggaccacg 360
gtcaccgtct cctca 375

<210> SEQ ID NO 95
<211> LENGTH: 125
<212> TYPE: PRT
<213> ORGANISM: Homo sapiens

<400> SEQUENCE: 95

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Arg Thr Tyr Asn Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Ala Thr Gly Arg Ala Asp Tyr His Phe Tyr Ala Met
            100                 105                 110

Asp Val Trp Gly Gln Gly Thr Thr Val Thr Val Ser Ser
        115                 120                 125

<210> SEQ ID NO 96
<211> LENGTH: 318
<212> TYPE: DNA
<213> ORGANISM: Homo sapiens

<400> SEQUENCE: 96
tcctatgagc tgacacagcc atcctcagtg tcagtgtctc cgggacagac agccaggatc 60
acctgctcag gagatgtact ggcaaaaaag tctgctcggt ggttccacca gaagccaggc 120
caggcccctg tactggtgat ttataaagac agtgagcggc cctcagggat ccctgagcgc 180
ttctccggct ccagctcagg gaccacagtc accttgacca tcagcggggc ccaggttgag 240
gatgaggctg actattactg ttactctgcg gctgacaaca atctggtatt cggcggaggg 300
accaagctga ccgtccta 318

<210> SEQ ID NO 97
<211> LENGTH: 106
<212> TYPE: PRT
<213> ORGANISM: Homo sapiens

<400> SEQUENCE: 97

Ser Tyr Glu Leu Thr Gln Pro Ser Ser Val Ser Val Ser Pro Gly Gln
1               5                   10                  15

-continued

```
Thr Ala Arg Ile Thr Cys Ser Gly Asp Val Leu Ala Lys Lys Ser Ala
            20                  25                  30

Arg Trp Phe His Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Leu Val
                85                  90                  95

Phe Gly Gly Gly Thr Lys Leu Thr Val Leu
            100                 105
```

ANTIBODIES DIRECTED TO αVβ6 AND USES THEREOF

CROSS-REFERENCE TO RELATED APPLICATIONS

This application is a divisional of U.S. application Ser. No. 12/782,335 filed on May 18, 2010, (now U.S. Pat. No. 8,398, 975 issued on Mar. 19, 2013), U.S. application Ser. No. 12/782,335 is a continuation of U.S. application Ser. No. 11/833,486 filed on Aug. 3, 2007. U.S. application Ser. No. 11/833,486 claims benefit under 35 U.S.C. §119(e) of the following U.S. Provisional Application No. 60/835,559 filed Aug. 3, 2006. Each of the above listed applications is incorporated by reference herein in its entirety for all purposes.

REFERENCE TO THE SEQUENCE LISTING

This application incorporates by reference a Sequence Listing submitted with this application as text file entitled A5B6100US3_seq_listing created on Jan. 15, 2013 and having a size of 83 kilobytes.

FIELD

The invention relates to monoclonal antibodies against alphaVbeta6 integrin (αVβ6) and uses of such antibodies. In some embodiments, the invention relates to fully human monoclonal antibodies directed to αVβ6. The described antibodies are useful as diagnostics and for the treatment of diseases associated with the activity and/or overproduction of αVβ6.

BACKGROUND

The integrin superfamily includes at least 24 family members consisting of heterodimers that utilize 18 alpha and 8 beta chains (Hynes, (2002) Cell 110: 673-87). This family of receptors is expressed on the cell surface and mediates cell-cell and cell-extracellular matrix interactions that regulate cell survival, proliferation, migration, and differentiation as well as tumor invasion and metastasis (ffrench-Constant and Colognato, (2004) Trends Cell Biol. 14: 678-86). Integrins bind to other cellular receptors, growth factors and extracellular matrix proteins, with many family members having overlapping binding specificity for particular proteins. This redundancy may ensure that important functions continue in the absence of a particular integrin (Koivisto et al., (2000) Exp. Cell Res. 255: 10-17). However, temporal and spacial restriction of expression of individual integrins with similar specificity has also been reported and may alter the cellular response to ligand binding (Yokosaki et al., (1996) J. Biol. Chem. 271: 24144-50; Kemperman et al., (1997) Exp. Cell Res. 234: 156-64; Thomas et al., (2006) J. Oral Pathol. Med. 35: 1-10).

The integrin family can be divided into several sub-families based on ligand specificity of the heterodimers. One subfamily consists of all of the integrins that recognize and bind the RGD tripeptide. These receptors include the αIIb/β3 and all of the αV heterodimers (Thomas et al., (2006) J. Oral Pathol. Med. 35: 1-10). While the αV chain can pair with 5 known beta chains, several of these beta chains can only pair with αV. The β6 chain is selective for heterodimerization to αV and this pair binds extracellular matrix and cytokine proteins with either high or low affinity. αVβ6 binds to the RGD motifs on both TGFβ1LAP and TGFβ3LAP latent complexes and activates them (Munger et al., (1999) Cell 96: 319-328; Annes et al., (2002) FEBS Letters 511: 65-68). However, it does not bind to or activate TGFβ2LAP, which does not have the tri-peptide (Ludbrook et al., (2003) Biochem. J. 369: 311-18). αVβ6-mediated activation of TGFβ requires the latent TGFβ binding protein 1 (LTBP1), which tethers the latent TGFβ complex to the extracellular matrix. Activation is proposed to result from a conformation change induced as the TGFβLAP is held between the cell and the matrix by αVβ6 and LTBP1, respectively (Keski-Oja et al., (2004) Trends Cell Biol. 14: 657-659; Annes et al., (2004) J. Cell Biol. 165: 723-34). The picoMolar binding affinity of αVβ6 for the TGFβLAP complexes is the highest for any of its known ligands. Other ligands for αVβ6 include fibronectin, tenascin, vitronectin and osteopontin (Busk et al., (1992) J. Biol. Chem. 267: 5790-6; Prieto et al., (1993) PNAS 90: 10154-8; Huang et al., (1998) J. Cell. Sci. 111(Pt 15): 2189-95; Yokosaki et al., (2005) Matrix Biol. 24: 418-27). The binding affinity of αVβ6 for these extracellular matrix proteins is low affinity and in the nanoMolar range.

Expression of αVβ6 integrin is restricted to areas of active tissue remodeling in the adult, specifically on the epithelia of healing wounds and at the edge of invading tumors (Breuss et al., (1995) J. Cell Sci. 108: 2241-51). Keratinocytes at the wound edge upregulate the expression of αVβ6 during their migration into the wound, but expression remains high after the edges of the wound epithelium have joined (Breuss et al., (1995) J. Cell Sci. 108: 2241-51; Haapasalmi et al., (1996) J. Invest. Dermatol. 106: 42-48). The wound extracellular matrix contains fibronectin, tenascin and vitronectin, all of which are ligands for αVβ6 (Busk et al., (1992) J. Biol. Chem. 267: 5790-6; Koivisto et al., (1999) Cell Adhes. Commun. 7: 245-57; Hakkinen et al., (2000) J. Histochem. Cytochem. 48: 985-98). In addition, αVβ6 upregulates the expression of the matrix metalloproteinase, MMP-9, that can degrade Type IV collagen and promote cell movement (Niu et al., (1998) Biochem. Biophys. Res. Com. 249: 287-91; Agrez et al., (1999) Int. J. Can. 81: 90-97; Thomas et al., (2001) Int. J. Cancer 92: 641-50; Gu et al., (2002) Br. J. Can. 87: 348-51). Based on its expression pattern in wounds and in vitro studies, αVβ6 may have dual roles to promote keratinocyte migration during wound closure and later to resolve the wound through the activation of TGFβ. The activation of TGFβ by αVβ6 would contribute to wound resolution through the regulation of re-epithelialization, suppression of inflammation and promotion of connective tissue regeneration and scar formation (Thomas et al., (2006) J. Oral Pathol. Med. 35: 1-10). In vivo wound studies using beta 6 null mice indicated that wounds healed but there was a markedly increased inflammatory response in the skin. Wound closure and keratinocyte activity was likely unaffected by the loss of αVβ6 because of the expression of other integrin family members (Huang et al., (1996) J. Cell Biol. 133: 921-8). The inflammatory infiltrate in the beta 6 null mouse wounds resembled those from TGFβ1 null mice, suggesting that there was insufficient activity of this cytokine to suppress the immune response in the absence of αVβ6 (Shull et al., (1992) Nature 359: 693-9; Thomas et al., (2006) J. Oral Pathol. Med. 35: 1-10).

Analysis of the beta 6 null mice in lung injury and kidney disease models has also identified a role for αVβ6 in fibrosis. Lung fibrosis in the beta 6 null mice was inhibited in a bleomycin injury model (Munger et al., (1999) Cell 96: 319-328). These animals also were protected from an MMP12 dependent emphasema-like phenotype (Morris et al., (2003) Nature 422: 169-73). Both disease phenotypes are dependent on the activation of TGFβ (Munger et al., (1999) Cell 96: 319-328). Inhibition of αVβ6 integrin-mediated TGFβ activation was also hypothesized to promote pulmonary edema in the early phase response to acute lung injury (Pittet et al., (2001) J. Clin. Invest. 107: 1537-44). Beta 6 null mice were also protected from fibrosis in a kidney disease model, where TGFβ activation is essential for the development of tubulointerstitial fibrotic lesions (Ma et al., (2003) Am. J. Pathol. 63: 1261-73).

In addition to its expression in wound healing, the αVβ6 integrin is upregulated at the periphery of many human tumors. αVβ6 expression has been reported in oral (Breuss et al., (1995) J. Cell Sci. 108: 2241-51; Jones et al., (1997) J. Oral Pathol. Med. 26: 63-8; Hamidi et al., (2000) Br. J Cancer 82: 1433-40; Regezi et al., (2002) Oral Oncology 38: 332-6; Impola et al., (2004) J. Pathol. 202: 14-22) and skin squamous cell carcinomas, as well as carcinomas of the lung (Smythe et al., (1995) Can. Met. Rev. 14: 229-39), breast (Arhiro et al., (2000) Breast Can. 7: 19-26), pancreas (Sipos, et al., (2004) Histopathology 45: 226-36), stomach (Kawashima et al., (2003) Pathol. Res. Pract. 199: 57-64), colon (Bates et al., (2005) J. Clin. Invest. 115: 339-47), ovary (Ahmed et al., (2002) Carcinogenesis 23: 237-44; Ahmed et al., (2002) J. Histochem. Cytochem. 50: 1371-79), and salivary gland (Westernoff et al., (2005) Oral Oncology 41: 170-74). In many of these reports the expression of αVβ6 correlated with increasing tumor grade (Ahmed et al., (2002) J. Histochem. Cytochem. 50: 1371-79; Arihiro et al., (2000) Breast Can. 7: 19-26), eventual metastases to lymph nodes (Kawashima et al., (2003) Pathol. Res. Pract. 199: 57-64; Bates et al., (2005) J. Clin. Invest. 115: 339-47), or poor prognosis (Bates et al., (2005) J. Clin. Invest. 115: 339-47). The most well studied tumor type is oral squamous cell carcinoma, where investigators have also examined αVβ6 in pre-cancerous lesions and correlated its expression with progression to malignancy (Hamidi et al., (2000) Br. J Cancer 82: 1433-40). The link between αVβ6 expression and tumor progression has also been investigated in colon carcinoma where the presence of integrin correlated with the epithelial-to-mesenchymal transition (EMT) of colon cells in an in vitro model (Brunton et al., (2001) Neoplasia 3: 215-26; Bates et al., (2005) J. Clin. Invest. 115: 339-47). The EMT is a normal developmental process that enables epithelial cells to leave their home tissue and migrate out to new areas (Thiery and Sleeman, (2006) Nat. Rev. Mol. Cell Biol. 7: 131-42). It is marked by an increase in the expression of proteins that promote the migration and invasion of cells, such as matrix proteases, cytokines like TGFβ and a variety of cellular adhesion molecules, including integrins (Zavadil and Bottinger, (2005) Oncogene 24: 5764-5774). The expression of EMT markers has also been identified in tumors, particularly in aggressively invasive and metastatic carcinomas. The ability of αVβ6 to promote adhesion to interstitial fibronectin, upregulate the expression of MMP-9 and other matrix proteases and to activate TGFβ indicates it may facilitate the EMT of malignant cells and tumor progression (Bates and Mercurio, (2005) Cancer Bio. & Ther. 4: 365-70).

Animal and in vitro models of human cancer have implicated αVβ6 mediated signal transduction in the promotion of cell proliferation and inhibition of apoptosis. The residues within the C-terminus of the beta 6 chain that promote proliferation of αVβ6-transfected SW480 colon tumor cells in a collagen gel matrix in vitro were identified. Compared to the full-length β6 transfected SW480 cells, the β6 deletion mutant had markedly reduced ability to grow sub-cutaneously in Nude mice (Agrez et al., (1994) J. Cell. Biol. 127: 547-56). In an oral cancer cell line that stably expressed αVβ6, binding to fibronectin resulted in the recruitment and activation of the Fyn kinase by the beta 6 subunit. Downstream signal transduction resulted in the production of MMP-3, promoted cell proliferation in vitro, tumor invasion in an orthotopic model, and metastasis in a tail vein injection model (Li et al., (2003) J. Biol. Chem. 278: 41646-53).

Suppression of apoptosis, like cell proliferation, is another way that αVβ6 may promote tumor growth. Normal stratified squamous epithelia express the αVβ5 integrin but down-regulate it and upregulate αVβ6 expression upon transformation to carcinomas. Using carcinoma cell lines that over-expressed αVβ5, αVβ6 expression was shown to prevent suspension-induced cell death (anoikis) in vitro (Janes and Watt, (2004) J. Cell Biol. 166: 419-31). Apoptosis inhibition has also been observed in vitro in ovarian cancer cell lines treated with cisplatin, which may represent a mechanism for drug resistance of these tumors in vivo (Wu et al., (2004) Zhonghua Fu Chan Ke Za Zhi 39: 112-14).

A number of investigators have developed therapeutics to target αVβ6 activity in fibrosis and cancer. A murine antibody with specificity for the αVβ6, αVβ3 and αVβ5 integrins was shown to prevent adhesion of HT29 colon carcinoma cells to vitronectin and fibronectin in vitro (Lehmann et al., (1994) Can. Res. 54: 2102-07). Another murine antibody therapeutic specific for the human αVβ6 protein was demonstrated to inhibit the invasive growth of HSC-3 oral carcinoma cells in a transoral xenograft tumor model in mice (Xue et al., (2001) Biochem. Biophys. Res. Com. 288: 610-18). A series of human αVβ6 specific antibodies were raised using the beta 6 null mouse model as the host. These antibodies were able to block both TGFβLAP and fibronectin binding to integrin in vitro (Weinreb et al., (2004) J. Biol. Chem. 279: 17875-87). They also demonstrated significant tumor growth inhibition in a human pharyngeal cancer xenograft model (Leone et al., (2003) Proc. of the Am. Assoc. Can. Res. 44, Abstract #4069).

In addition to function blocking antibodies the creation of a peptidomimetic inhibitor of the human αVβ6 integrin has been reported. This compound was shown to inhibit UCLAP-3 cell binding to fibronectin with an IC50 in the 200 nM range with additional activity to block αVβ5 and αVβ3 integrin-mediated cell binding to vitronectin in the 3-20 uM range, respectively (Goodman et al., (2002) J. Med. Chem. 45: 1045-51).

Another recently described role for αVβ6 is as a cellular receptor for viral pathogens. It mediates the binding of the viral capsid for foot-and-mouth disease virus and the Coxsackievirus 9 to enable viral entry in vitro (Miller et al., (2001) J. Virol. 75: 4158-64; Williams et al., (2004) J. Virol. 78: 6967-73). Both foot-and-mouth disease virus and Coxsackievirus 9 capsid proteins contain an RGD sequence that is recognized by multiple integrin family members. Viral entry of both pathogens is blocked by antibody to αVβ6 integrin (Williams et al., (2004) J. Virol. 78: 6967-73).

SUMMARY

The invention is generally directed to targeted binding agents that bind to αVβ6. Embodiments of the invention relate to fully human targeted binding agents that specifically bind to αVβ6 and thereby inhibit binding of ligands to αVβ6. The targeted binding agents also inhibit tumor cell adhesion. In addition, the targeted binding agents are useful for reducing tumor growth. Mechanisms by which this can be achieved can include and are not limited to either inhibiting binding of a ligand to its receptor αVβ6, abrogation of intereactions with ligands such as TGFβLAP, thereby reducing the effective concentration of αVβ6.

In one embodiment of the invention, the targeted binding agent is a fully human antibody that binds to αVβ6 and prevents αVβ6 binding to ligands of αVβ6. Examples of ligands of αVβ6 include TGFβLAP, fibronectin, tenascin, vitronectin and osteopontin. The antibody may bind αVβ6 with a $K_d$ of less than 35 nM, 25 nM, 10 nM, or 60 pM.

Yet another embodiment is a fully human antibody that binds to αVβ6 and inhibits greater than 80%, 85%, 90% or 99% of TGFβ-LAP mediated adhesion of HT29 cells at antibody concentrations as low as 1 μg/ml or less.

Yet another embodiment is a fully human antibody that binds to αVβ6 and inhibits TGFβ3-LAP mediated adhesion of HT29 cells with an $IC_{50}$ of less than 0.070 μg/ml.

The targeted binding agent (i.e. an antibody) may comprise a heavy chain amino acid sequence having a complementarity determining region (CDR) with one of the sequences shown in Table 8 or Table 29. In one embodiment the targeted binding agent may comprise a sequence comprising any one of a CDR1, CDR2 or CDR3 sequence as shown in Table 8 or Table 29. In another embodiment the targeted binding agent may comprise a sequence comprising any two of a CDR1, CDR2 or CDR3 sequence as shown in Table 8 or Table 29 (that is either a CDR1 and CDR2, a CDR1 and CDR3 or a CDR2 and CDR3). In another embodiment the targeted binding agent may comprise a sequence comprising a CDR1, CDR2 and CDR3 sequence as shown in Table 8 or Table 29. It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3.

In another embodiment the targeted binding agent (i.e. an antibody) may comprise a light chain amino acid sequence having a complementarity determining region (CDR), CDR1, CDR2 or CDR3 sequences as shown in Table 9 or Table 30. In another embodiment the targeted binding agent may comprise a sequence comprising any two of a CDR1, CDR2 or CDR3 sequence as shown in Table 9 or Table 30 (that is either a CDR1 and CDR2, a CDR1 and CDR3, or a CDR2 and CDR3). In another embodiment the targeted binding agent may comprise a sequence comprising a CDR1, CDR2 and CDR3 sequence as shown in Table 9 or Table 30.

The targeted binding agent of the invention may comprise an antigen-binding site within a non-antibody molecule, normally provided by one or more CDRs e.g. a set of CDRs in a non-antibody protein scaffold, as discussed further below.

In another embodiment the targeted binding agent comprises a sequence comprising any one of a CDR1, CDR2 or CDR3 sequence of fully human monoclonal antibodies sc 264 RAD, sc 264 RAD/ADY, sc 188 SDM, sc 133, sc 133 TMT, sc 133 WDS, sc 133 TMT/WDS, sc 188, sc 254, sc 264 or sc 298.

In another embodiment the targeted binding agent comprises any two of a CDR1, CDR2 or CDR3 sequence of fully human monoclonal antibodies sc 264 RAD, sc 264 RAD/ADY, sc 188 SDM, sc 133, sc 133 TMT, sc 133 WDS, sc 133 TMT/WDS, sc 188, sc 254, sc 264 or sc 298 (that is either a CDR1 and CDR2, a CDR1 and CDR3 or a CDR2 and CDR3).

In another embodiment the targeted binding agent comprises a CDR1, CDR2 and CDR3 sequence of fully human monoclonal antibodies sc 264 RAD, sc 264 RAD/ADY, sc 188 SDM, sc 133, sc 133 TMT, sc 133 WDS, sc 133 TMT/WDS, sc 188, sc 254, sc 264 or sc 298.

In one embodiment of the invention, the targeted binding agent is an antibody. In one embodiment of the invention, the targeted binding agent is a monoclonal antibody. In one embodiment of the invention, the targeted binding agent is a fully human monoclonal antibody.

Another embodiment of the invention comprises an antibody that binds to αVβ6 and comprises a light chain amino acid sequence comprising any one of a CDR1, CDR2 or CDR3 sequence as shown in Table 9 or Table 30. Another embodiment of the invention comprises an antibody that binds to αVβ6 and comprises a light chain amino acid sequence comprising any two of a CDR1, CDR2 or CDR3 sequence as shown in Table 9 or Table 30 (that is either a CDR1 and CDR2, a CDR1 and CDR3 or a CDR2 and CDR3). Another embodiment of the invention comprises an antibody that binds to αVβ6 and comprises a light chain amino acid sequence comprising a CDR1, a CDR2 and a CDR3 sequence as shown in Table 9 or Table 30. In certain embodiments the antibody is a fully human monoclonal antibody.

Yet another embodiment of the invention comprises an antibody that binds to αVβ6 and comprises a heavy chain amino acid sequence comprising any one of a CDR1, CDR2 or CDR3 sequence as shown in Table 8 or Table 29. Another embodiment of the invention comprises an antibody that binds to αVβ6 and comprises a heavy chain amino acid sequence comprising any two of a CDR1, CDR2 or CDR3 sequence as shown in Table 8 or Table 29 (that is either a CDR1 and CDR2, a CDR1 and CDR3 or a CDR2 and CDR3). Another embodiment of the invention comprises an antibody that binds to αVβ6 and comprises a heavy chain amino acid sequence comprising a CDR1, a CDR2 and a CDR3 sequence as shown in Table 8 or Table 29. In certain embodiments the antibody is a fully human monoclonal antibody.

One embodiment of the invention comprises one or more of fully human monoclonal antibodies sc 264 RAD, sc 264 RAD/ADY, sc 188 SDM, sc 133, sc 133 TMT, sc 133 WDS, sc 133 TMT/WDS, sc 188, sc 254, sc 264 or sc 298 which specifically bind to αVβ6, as discussed in more detail below.

Yet another embodiment is an antibody that binds to αVβ6 and comprises a light chain amino acid sequence having a CDR comprising one of the sequences shown in Table 9 or Table 30. Another embodiment is an antibody that binds to αVβ6 and comprises a heavy chain amino acid sequence having a CDR comprising one of the sequences shown in Table 8 or Table 29. In certain embodiments the antibody is a fully human monoclonal antibody.

A further embodiment is an antibody that binds to αVβ6 and comprises a heavy chain amino acid sequence having one of the CDR sequences shown in Table 8 or Table 29 and a light chain amino acid sequence having one of the CDR sequences shown in Table 9 or Table 30. In certain embodiments the antibody is a fully human monoclonal antibody.

A further embodiment of the invention is a targeted binding agent (i.e. an antibody) that competes for binding to αVβ6 with the antibodies of the invention. In one embodiment, said targeted binding agent comprises a heavy chain amino acid sequence having at least one of the CDR sequences shown in Table 8 or Table 29 and a light chain amino acid sequence having at least one of the CDR sequences shown in Table 9 or Table 30.

A further embodiment of the invention is a targeted binding agent that binds to the same epitope on αVβ6 as the antibodies of the invention. In one embodiment, said targeted binding agent comprised a heavy chain amino acid sequence having at least one of the CDR sequences shown in Table 8 or Table 29 and a light chain amino acid sequence having at least one of the CDR sequences shown in Table 9 or Table 30.

In another embodiment the targeted binding agent comprises a sequence comprising any one of a CDR1, CDR2 or CDR3 sequence as shown in Table 8 or Table 29 and any one of a CDR1, CDR2 or CDR3 sequence as shown in Table 9 or Table 30. In another embodiment the targeted binding agent comprises any two of a CDR1, CDR2 or CDR3 sequence shown in Table 8 or Table 29 and any two of a CDR1, CDR2 or CDR3 sequence as shown in Table 9 or Table 30 (that is either a CDR1 and CDR2, a CDR1 and CDR3 or a CDR2 and CDR3). In another embodiment the targeted binding agent comprises a CDR1, CDR2 and CDR3 sequence as shown in Table 8 or Table 29 and a CDR1, CDR2 and CDR3 sequence as shown in Table 9 or Table 30.

In some embodiments, a binding agent of the invention may comprise an antigen-binding site within a non-antibody molecule, normally provided by one or more CDRs e.g. a set of CDRs in a non-antibody protein scaffold, as discussed further below.

A still further embodiment is an antibody that binds to αVβ6 and comprises an amino acid sequence having one or more corrective mutations where the antibody sequence is mutated back to its respective germline sequence. For example, the antibody can have a sequence as shown in any of Tables 10-13.

The invention further provides methods for assaying the level of αVβ6 in a patient or patient sample, comprising contacting an anti-αVβ6 antibody with a biological sample from a patient, and detecting the level of binding between said antibody and αVβ6 in said sample. In more specific embodiments, the biological sample is blood, or plasma.

In other embodiments the invention provides compositions comprising targeted binding agent, including an antibody or functional fragment thereof, and a pharmaceutically acceptable carrier.

Still further embodiments of the invention include methods of effectively treating an animal suffering from an αVβ6-related disease or disorder, including selecting an animal in need of treatment for a neoplastic or non-neoplastic disease, and administering to the animal a therapeutically effective dose of a fully human monoclonal antibody that specifically binds to αVβ6.

The antibodies of the invention can be used to treat an αVβ6-related disease or disorder. An αVβ6-related disease or disorder can be any condition arising due to the aberrant activation or expression of αVβ6. Examples of such diseases include where αVβ6 aberrantly interacts with its ligands thereby altering cell-adhesion or cell signaling properties. This alteration in cell adhesion or cell signaling properties can result in neoplastic diseases. Other αVβ6-related diseases or disorders include inflammatory disorders, lung disease, diseases associated with fibrosis and any disease associated with dysregulated TGF-β.

In one example, the αVβ6-related disease is a neoplastic disease such as melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

In another example, the αVβ6-related disease is an inflammatory disorder such as inflammatory bowel disease; systemic lupus erythematosus; rheumatoid arthritis; juvenile chronic arthritis; spondyloarthropathies; systemic sclerosis, for example, scleroderma; idiopathic inflammatory myopathies for example, dermatomyositis, polymyositis; Sjogren's syndrome; systemic vaculitis; sarcoidosis; thyroiditis, for example, Grave's disease, Hashimoto's thyroiditis, juvenile lymphocytic thyroiditis, atrophic thyroiditis; immune-mediated renal disease, for example, glomerulonephritis, tubulointerstitial nephritis; demyelinating diseases of the central and peripheral nervous systems such as multiple sclerosis, idiopathic polyneuropathy; hepatobiliary diseases such as infectious hepatitis such as hepatitis A, B, C, D, E and other nonhepatotropic viruses; autoimmune chronic active hepatitis; primary biliary cirrhosis; granulomatous hepatitis; and sclerosing cholangitis; inflammatory and fibrotic lung diseases (e.g., cystic fibrosis); gluten-sensitive enteropathy; autoimmune or immune-mediated skin diseases including bullous skin diseases, erythema multiforme and contact dermatitis, psoriasis; allergic diseases of the lung such as eosinophilic pneumonia, idiopathic pulmonary fibrosis, allergic conjunctivitis and hypersensitivity pneumonitis, transplantation associated diseases including graft rejection and graft-versus host disease.

In yet another example, the αVβ6-related disease is fibrosis such as kidney or lung fibrosis.

In yet another example, the αVβ6-related disease is associated with dysregulated TGF-β include cancer and connective tissue (fibrotic) disorders.

Additional embodiments of the invention include methods of inhibiting αVβ6 induced cell adhesion in an animal. These methods include selecting an animal in need of treatment for αVβ6 induced cell adhesion, and administering to said animal a therapeutically effective dose of a fully human monoclonal antibody wherein said antibody specifically binds to αVβ6.

Further embodiments of the invention include the use of an antibody in the preparation of medicament for the treatment of an αVβ6 related disease or disorder in an animal, wherein said monoclonal antibody specifically binds to αVβ6.

In still further embodiments, the targeted binding agents described herein can be used for the preparation of a medicament for the effective treatment of αVβ6 induced cell adhesion in an animal, wherein said monoclonal antibody specifically binds to αVβ6.

Embodiments of the invention described herein relate to monoclonal antibodies that bind αVβ6 and affect αVβ6 function. Other embodiments relate to fully human anti-αVβ6 antibodies and anti-αVβ6 antibody preparations with desirable properties from a therapeutic perspective, including high binding affinity for αVβ6, the ability to neutralize αVβ6 in vitro and in vivo, and the ability to inhibit αVβ6 induced cell adhesion and tumor growth.

In one embodiment, the invention includes antibodies that bind to αVβ6 with very high affinities (KD). For example a human, rabbit, mouse, chimeric or humanized antibody that is capable of binding αVβ6 with a Kd less than, but not limited to, about $10^{-5}$, $10^{-6}$, $10^{-7}$, $10^{-8}$, $10^{-9}$, $10^{-10}$ or about $10^{-11}$M, or any range or value therein. Affinity and/or avidity measurements can be measured by KinExA® and/or BIACORE®, as described herein.

One embodiment of the invention includes isolated antibodies, or fragments of those antibodies, that bind to αVβ6. As known in the art, the antibodies can be, for example, polyclonal, oligoclonal, monoclonal, chimeric, humanized, and/or fully human antibodies. Embodiments of the invention described herein also provide cells for producing these antibodies.

It will be appreciated that embodiments of the invention are not limited to any particular form of an antibody or method of generation or production. For example, the anti-αVβ6 antibody may be a full-length antibody (e.g., having an intact human Fc region) or an antibody fragment (e.g., a Fab, Fab' or $F(ab')_2$, FV or Dab (Dabs are the smallest functional binding units of human antibodies). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having isolated nucleic acid molecules encoding anti-αVβ6 antibodies or a host cell transformed with any of such nucleic acid molecules. In addition, one embodiment of the invention is a method of producing an anti-αVβ6 antibody by culturing host cells under conditions wherein a nucleic acid molecule is expressed to produce the antibody followed by recovering the antibody. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

A further embodiment includes a method of producing high affinity antibodies to αVβ6 by immunizing a mammal with human αVβ6, or a fragment thereof, and one or more orthologous sequences or fragments thereof.

Other embodiments are based upon the generation and identification of isolated antibodies that bind specifically to αVβ6. Inhibition of the biological activity of αVβ6 can prevent αVβ6 induced cell adhesion and other desired effects.

Another embodiment of the invention includes a method of diagnosing diseases or conditions in which an antibody prepared as described herein is utilized to detect the level of αVβ6 in a patient sample. In one embodiment, the patient sample is blood or blood serum. In further embodiments, methods for the identification of risk factors, diagnosis of disease, and staging of disease is presented which involves the identification of the overexpression of αVβ6 using anti-αVβ6 antibodies.

Another embodiment of the invention includes a method for diagnosing a condition associated with the expression of αVβ6 in a cell by contacting the serum or a cell with an anti-αVβ6 antibody, and thereafter detecting the presence of αVβ6. Preferred conditions include an αVβ6 related disease or disorder including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention includes an assay kit for detecting αVβ6 in mammalian tissues, cells, or body fluids to screen for αVβ6-related diseases. The kit includes an antibody that binds to αVβ6 and a means for indicating the reaction of the antibody with αVβ6, if present. In one embodiment, the antibody is a monoclonal antibody. In another embodiment, the antibody that binds αVβ6 is labeled. In still another embodiment the antibody is an unlabeled primary antibody and the kit further includes a means for detecting the primary antibody. In one embodiment, the means for detecting includes a labeled second antibody that is an anti-immunoglobulin. The antibody may be labeled with a marker selected from the group consisting of a fluorochrome, an enzyme, a radionuclide and a radiopaque material.

Other embodiments of the invention include pharmaceutical compositions having an effective amount of an anti-αVβ6 antibody in admixture with a pharmaceutically acceptable carrier or diluent. In yet other embodiments, the anti-αVβ6 antibody, or a fragment thereof, is conjugated to a therapeutic agent. The therapeutic agent can be, for example, a toxin or a radioisotope.

Yet another embodiment includes methods for treating diseases or conditions associated with the expression of αVβ6 in a patient, by administering to the patient an effective amount of an anti-αVβ6 antibody. The anti-αVβ6 antibody can be administered alone, or can be administered in combination with additional antibodies or chemotherapeutic drug or radiation therapy. For example, a monoclonal, oligoclonal or polyclonal mixture of αVβ6 antibodies that block cell adhesion can be administered in combination with a drug shown to inhibit tumor cell proliferation directly. The method can be performed in vivo and the patient is preferably a human patient. In a preferred embodiment, the method concerns the treatment of an αVβ6 related disease or disorder including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention provides an article of manufacture including a container. The container includes a composition containing an anti-αVβ6 antibody, and a package insert or label indicating that the composition can be used to treat an αVβ6 related disease or disorder characterized by the overexpression of αVβ6.

In some embodiments, the anti-αVβ6 antibody is administered to a patient, followed by administration of a clearing agent to remove excess circulating antibody from the blood.

Yet another embodiment is the use of an anti-αVβ6 antibody in the preparation of a medicament for the treatment of αVβ6-related diseases or disorders such as neoplastic diseases, inflammatory disorders, fibrosis, lung disease or diseases associated with dysregulated TGF-β. In one embodiment, the neoplastic diseases include carcinoma, such as breast, ovarian, stomach, endometrial, salivary gland, lung, kidney, colon, colorectum, esophageal, thyroid, pancreatic, prostate and bladder cancer. In another embodiment, the αVβ6 related diseases or disorders include, but are not limited to, neoplastic diseases, such as, melanoma, small cell lung cancer, non-small cell lung cancer, glioma, hepatocellular (liver) carcinoma, sarcoma, head and neck cancers, mesothelioma, biliary (cholangiocarcinoma), small bowel adenocarcinoma, pediatric malignancies and glioblastoma.

Yet another embodiment of the invention is the use of an anti-αVβ6 antibody in the preparation of a medicament for the treatment of inflammatory, or hyperprolifearative diseases including but not limited to arthritis, atherosclerosis, allergic conjunctivitis.

BRIEF DESCRIPTION OF THE DRAWINGS

FIG. 2B shows affinity data for mAb 264 RAD.

DETAILED DESCRIPTION

Figure 1:
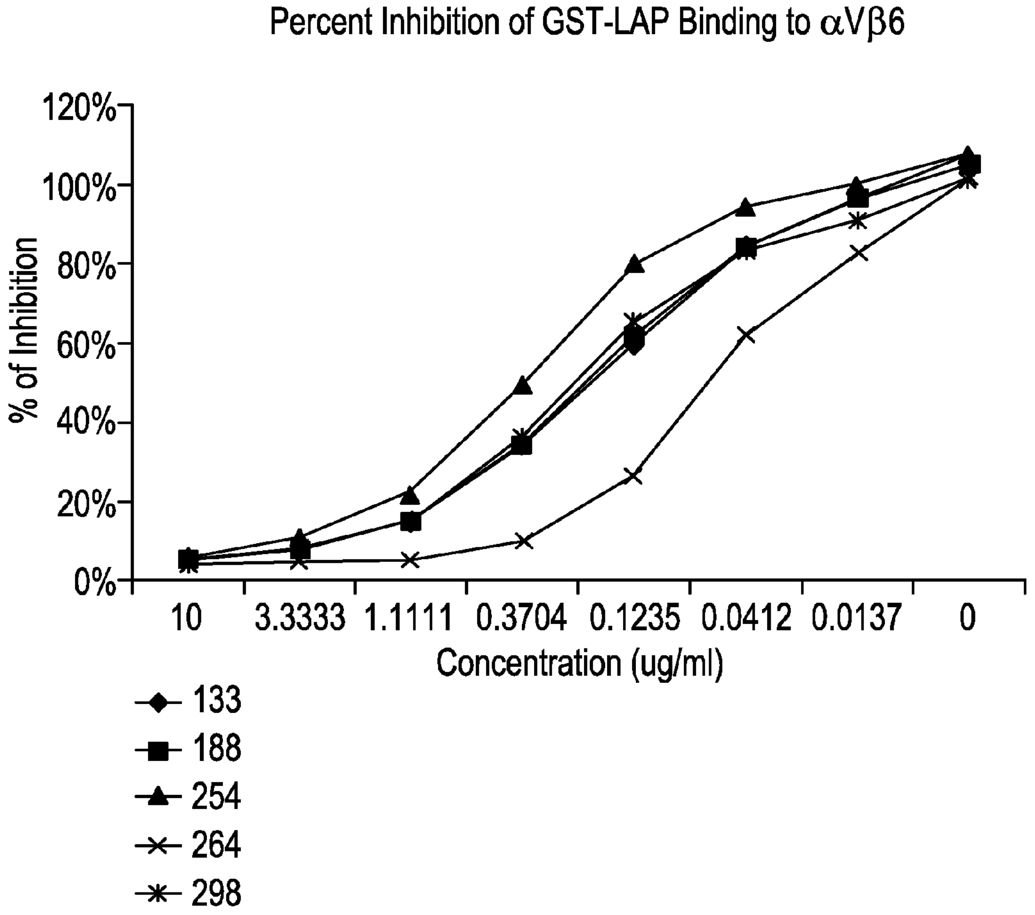
FIG. 1 is a line graph showing the ability of the purified monoclonal antibodies to bind to αVβ6 and block its binding to a GST-LAP peptide.

Embodiments of the invention relate to targeted binding agents that bind to αVβ6 integrin (αVβ6). In some embodiments, the binding agents bind to αVβ6 and inhibit the binding of ligands to αVβ6. In one embodiment, the targeted binding agents are monoclonal antibodies, or binding fragments thereof. In another embodiment, the antibodies bind only to the β6 chain yet are able to inhibit binding of ligands to αVβ6.

Other embodiments of the invention include fully human anti-αVβ6 antibodies, and antibody preparations that are therapeutically useful. In one embodiment, the anti-αVβ6 antibody preparations have desirable therapeutic properties, including strong binding affinity for αVβ6, and the ability to inhibit TGFβLAP mediated cell adhesion in vitro.

Embodiments of the invention also include fully human isolated binding fragments of anti-αVβ6 antibodies. In one embodiment the binding fragments are derived from fully human anti-αVβ6 antibodies. Exemplary fragments include Fv, Fab' or other well-known antibody fragments, as described in more detail below. Embodiments of the invention also include cells that express fully human antibodies against αVβ6. Examples of cells include hybridomas, or recombinantly created cells, such as Chinese hamster ovary (CHO) cells, variants of CHO cells (for example DG44) and NS0 cells that produce antibodies against αVβ6. Additional information about variants of CHO cells can be found in Andersen and Reilly (2004) *Current Opinion in Biotechnology* 15, 456-462 which is incorporated herein in its entirety by reference.

In addition, embodiments of the invention include methods of using these antibodies for treating an αVβ6-related disease or disorder. An αVβ6-related disease or disorder can be any condition arising due to the aberrant activation or expression of αVβ6. Examples of such diseases include where αVβ6 aberrantly interacts with its ligands thereby altering cell-adhesion or cell signaling properties. This alteration in cell adhesion or cell signaling properties can result in neoplastic diseases. Other αVβ6-related diseases or disorders include inflammatory disorders, lung disease, diseases associated with fibrosis and any disease associated with dysregulated TGF-β.

In one example, the αVβ6-related disease is a neoplastic disease such as melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

In another example, the αVβ6-related disease is an inflammatory disorder such as inflammatory bowel disease; systemic lupus erythematosus; rheumatoid arthritis; juvenile chronic arthritis; spondyloarthropathies; systemic sclerosis, for example, scleroderma; idiopathic inflammatory myopathies for example, dermatomyositis, polymyositis; Sjogren's syndrome; systemic vaculitis; sarcoidosis; thyroiditis, for example, Grave's disease, Hashimoto's thyroiditis, juvenile lymphocytic thyroiditis, atrophic thyroiditis; immune-mediated renal disease, for example, glomerulonephritis, tubulointerstitial nephritis; demyelinating diseases of the central and peripheral nervous systems such as multiple sclerosis, idiopathic polyneuropathy; hepatobiliary diseases such as infectious hepatitis such as hepatitis A, B, C, D, E and other nonhepatotropic viruses; autoimmune chronic active hepatitis; primary biliary cirrhosis; granulomatous hepatitis; and sclerosing cholangitis; inflammatory and fibrotic lung diseases (e.g., cystic fibrosis); gluten-sensitive enteropathy; autoimmune or immune-mediated skin diseases including bullous skin diseases, erythema multiforme and contact dermatitis, psoriasis; allergic diseases of the lung such as eosinophilic pneumonia, idiopathic pulmonary fibrosis, allergic conjunctivitis and hypersensitivity pneumonitis, transplantation associated diseases including graft rejection and graft-versus host disease.

In yet another example, the αVβ6-related disease is fibrosis such as kidney or lung fibrosis.

In yet another example, the αVβ6-related disease is associated with dysregulated TGF-β include cancer and connective tissue (fibrotic) disorders.

Other embodiments of the invention include diagnostic assays for specifically determining the quantity of αVβ6 in a biological sample. The assay kit can include anti-αVβ6 antibodies along with the necessary labels for detecting such antibodies. These diagnostic assays are useful to screen for αV related diseases or β6 disorders including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

Another aspect of the invention is an antagonist of the biological activity of αVβ6 wherein the antagonist binds to αVβ6. In one embodiment, the antagonist is a targeted binding agent, such as an antibody. The antagonist may bind to:

i) β6 alone;

ii) αVβ6; or iii) the αVβ6/ligand complex, or a combination of these. In one embodiment the antibody is able to antagonize the biological activity of αVβ6 in vitro and in vivo. The antibody may be selected from fully human monoclonal antibody e.g., sc 264 RAD, sc 264 RAD/ADY, sc 188 SDM, sc 133, sc 133 TMT, sc 133 WDS, sc 133 TMT/WDS, sc 188, sc 254, sc 264 or sc 298 or variants thereof.

In one embodiment the antagonist of the biological activity of αVβ6 may bind to αVβ6 and thereby prevent TGFβLAP mediated cell adhesion.

One embodiment is an antibody which binds to the same epitope or epitopes as fully human monoclonal antibody c 264 RAD, sc 264 RAD/ADY, sc 188 SDM, sc 133, sc 133 TMT, sc 133 WDS, sc 133 TMT/WDS, sc 188, sc 254, sc 264 or sc 298.

In one embodiment, the targeted binding agent binds αVβ6 with a $K_d$ of less than 100 nanomolar (nM). The targeted binding agent may bind with a $K_d$ less than about 35 nanomolar (nM). The targeted binding agent may bind with a $K_d$ less than about 25 nanomolar (nM). The targeted binding agent may bind with a $K_d$ less than about 10 nanomolar (nM). In another embodiment, the targeted binding agent binds with a $K_d$ of less than about 60 picomolar (pM).

One embodiment is an antibody-secreting plasma cell that produces the light chain and/or the heavy chain of antibody as described hereinabove. In one embodiment the plasma cell produces the light chain and/or the heavy chain of a fully human monoclonal antibody. In another embodiment the plasma cell produces the light chain and/or the heavy chain of the fully human monoclonal antibody c 264 RAD, sc 264 RAD/ADY, sc 188 SDM, sc 133, sc 133 TMT, sc 133 WDS, sc 133 TMT/WDS, sc 188, sc 254, sc 264 or sc 298. Alternatively the plasma cell may produce an antibody which binds to the same epitope or epitopes as fully human monoclonal antibody sc c 264 RAD, sc 264 RAD/ADY, sc 188 SDM, sc 133, sc 133 TMT, sc 133 WDS, sc 133 TMT/WDS, sc 188, sc 254, sc 264 or sc 298.

Another embodiment is a nucleic acid molecule encoding the light chain or the heavy chain of an antibody as described hereinabove. In one embodiment the nucleic acid molecule encodes the light chain or the heavy chain of a fully human monoclonal antibody. Still another embodiment is a nucleic acid molecule encoding the light chain or the heavy chain of a fully human monoclonal antibody selected from antibodies c 264 RAD, sc 264 RAD/ADY, sc 188 SDM, sc 133, sc 133 TMT, sc 133 WDS, sc 133 TMT/WDS, sc 188, sc 254, sc 264 or sc 298.

Another embodiment of the invention is a vector comprising a nucleic acid molecule or molecules as described hereinabove, wherein the vector encodes a light chain and/or a heavy chain of an antibody as defined hereinabove.

Yet another embodiment of the invention is a host cell comprising a vector as described hereinabove. Alternatively the host cell may comprise more than one vector.

In addition, one embodiment of the invention is a method of producing an antibody by culturing host cells under conditions wherein a nucleic acid molecule is expressed to produce the antibody, followed by recovery of the antibody.

In one embodiment the invention includes a method of making an antibody by transfecting at least one host cell with at least one nucleic acid molecule encoding the antibody as described hereinabove, expressing the nucleic acid molecule in the host cell and isolating the antibody.

According to another aspect, the invention includes a method of antagonising the biological activity of αVβ6 comprising administering an antagonist as described herein. The method may include selecting an animal in need of treatment for an αVβ6 related disease or disorder, and administering to the animal a therapeutically effective dose of an antagonist of the biological activity of αVβ6.

Another aspect of the invention includes a method of antagonising the biological activity of αVβ6 comprising administering an antibody as described hereinabove. The method may include selecting an animal in need of treatment for an αVβ6 related disease or disorder, and administering to said animal a therapeutically effective dose of an antibody which antagonises the biological activity of αVβ6.

According to another aspect there is provided a method of treating an αVβ6 related disease or disorder in a mammal comprising administering a therapeutically effective amount of an antagonist of the biological activity of αVβ6. The method may include selecting an animal in need of treatment for an αVβ6 related disease or disorder, and administering to said animal a therapeutically effective dose of an antagonist of the biological activity of αVβ6.

According to another aspect there is provided a method of treating an αVβ6 disease or disorder in a mammal comprising administering a therapeutically effective amount of an antibody which antagonizes the biological activity of αVβ6. The method may include selecting an animal in need of treatment for an αVβ6 related disease or disorder, and administering to said animal a therapeutically effective dose of an antibody which antagonises the biological activity of αVβ6. The antibody can be administered alone, or can be administered in combination with additional antibodies or chemotherapeutic drug or radiation therapy.

According to another aspect there is provided a method of treating cancer in a mammal comprising administering a therapeutically effective amount of an antagonist of the biological activity of αVβ6. The method may include selecting an animal in need of treatment for cancer, and administering to said animal a therapeutically effective dose of an antagonist which antagonises the biological activity of αVβ6. The antagonist can be administered alone, or can be administered in combination with additional antibodies or chemotherapeutic drug or radiation therapy.

According to another aspect there is provided a method of treating cancer in a mammal comprising administering a therapeutically effective amount of an antibody which antagonizes the biological activity of αVβ6. The method may include selecting an animal in need of treatment for cancer, and administering to said animal a therapeutically effective dose of an antibody which antagonises the biological activity of αVβ6. The antibody can be administered alone, or can be administered in combination with additional antibodies or chemotherapeutic drug or radiation therapy.

According to another aspect of the invention there is provided the use of an antagonist of the biological activity of αVβ6 for the manufacture of a medicament for the treatment of an αVβ6 related disease or disorder.

According to another aspect of the invention there is provided the use of an antibody which antagonizes the biological activity of αVβ6 for the manufacture of a medicament for the treatment of an αVβ6 related disease or disorder.

In a preferred embodiment the present invention is particularly suitable for use in antagonizing αVβ6, in patients with a tumor which is dependent alone, or in part, on αVβ6 integrin.

Another embodiment of the invention includes an assay kit for detecting αVβ6 in mammalian tissues, cells, or body fluids to screen for an αVβ6 related disease or disorder. The kit includes an antibody that binds to αVβ6 and a means for indicating the reaction of the antibody with αVβ6, if present. The antibody may be a monoclonal antibody. In one embodiment, the antibody that binds αVβ6 is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding anti-αVβ6 antibodies are provided in additional detail below.

Sequence Listing

Embodiments of the invention include the specific anti-αVβ6 antibodies listed below in Table 1. This table reports the identification number of each anti-αVβ6 antibody, along with the SEQ ID number of the variable domain of the corresponding heavy chain and light chain genes. Each antibody has been given an identification number that includes the letters "sc" followed by a number.

TABLE 1

| mAb ID No.: | Sequence NO: | SEQ ID |
|---|---|---|
| sc 49 | Nucleotide sequence encoding the variable region of the heavy chain | 1 |
| | Amino acid sequence encoding the variable region of the heavy chain | 2 |

TABLE 1-continued

| mAb ID No.: | Sequence NO: | SEQ ID |
|---|---|---|
| | Nucleotide sequence encoding the variable region of the light chain | 3 |
| | Amino acid sequence encoding the variable region of the light chain | 4 |
| sc 58 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| sc 97 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| sc 133 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| sc 161 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| sc 188 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |
| sc 254 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| sc 264 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| sc 277 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| sc 298 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |
| sc 320 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| sc 374 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| sc 188 SDM | Nucleotide sequence encoding the variable region of the heavy chain | 70 |
| | Amino acid sequence encoding the variable region of the heavy chain | 71 |
| | Nucleotide sequence encoding the variable region of the light chain | 72 |
| | Amino acid sequence encoding the variable region of the light chain | 73 |
| sc 264 RAD | Nucleotide sequence encoding the variable region of the heavy chain | 74 |
| | Amino acid sequence encoding the variable region of the heavy chain | 75 |
| | Nucleotide sequence encoding the variable region of the light chain | 76 |
| | Amino acid sequence encoding the variable region of the light chain | 77 |
| sc 133 TMT | Nucleotide sequence encoding the variable region of the heavy chain | 78 |
| | Amino acid sequence encoding the variable region of the heavy chain | 79 |
| | Nucleotide sequence encoding the variable region of the light chain | 80 |
| | Amino acid sequence encoding the variable region of the light chain | 81 |
| sc 133 WDS | Nucleotide sequence encoding the variable region of the heavy chain | 82 |
| | Amino acid sequence encoding the variable region of the heavy chain | 83 |
| | Nucleotide sequence encoding the variable region of the light chain | 84 |
| | Amino acid sequence encoding the variable region of the light chain | 85 |
| sc 133 TMT/WDS | Nucleotide sequence encoding the variable region of the heavy chain | 86 |
| | Amino acid sequence encoding the variable region of the heavy chain | 87 |
| | Nucleotide sequence encoding the variable region of the light chain | 88 |
| | Amino acid sequence encoding the variable region of the light chain | 89 |
| sc 264 ADY | Nucleotide sequence encoding the variable region of the heavy chain | 90 |
| | Amino acid sequence encoding the variable region of the heavy chain | 91 |
| | Nucleotide sequence encoding the variable region of the light chain | 92 |
| | Amino acid sequence encoding the variable region of the light chain | 93 |
| sc 264 RAD/ADY | Nucleotide sequence encoding the variable region of the heavy chain | 94 |
| | Amino acid sequence encoding the variable region of the heavy chain | 95 |
| | Nucleotide sequence encoding the variable region of the light chain | 96 |
| | Amino acid sequence encoding the variable region of the light chain | 97 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular *Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

An antagonist may be a polypeptide, nucleic acid, carbohydrate, lipid, small molecular weight compound, an oligonucleotide, an oligopeptide, RNA interference (RNAi), antisense, a recombinant protein, an antibody, or conjugates or fusion proteins thereof. For a review of RNAi see Milhavet O, Gary D S, Mattson M P. (Pharmacol Rev. 2003 December; 55(4):629-48. Review.) and antisense see Opalinska J B, Gewirtz A M. (Sci STKE. 2003 Oct. 28; 2003 (206):pe47.)

Disease-related aberrant activation or expression of "αVβ6" may be any abnormal, undesirable or pathological cell adhesion, for example tumor-related cell adhesion. Cell adhesion-related diseases include, but are not limited to, non-solid tumors such as leukemia, multiple myeloma or lymphoma, and also solid tumors such as melanoma, small cell lung cancer, non-small cell lung cancer, glioma, hepatocellular (liver) carcinoma, glioblastoma, carcinoma of the thyroid, bile duct, bone, gastric, brain/CNS, head and neck, hepatic system, stomach, prostate, breast, renal, testicle, ovary, skin, cervix, lung, muscle, neuron, oesophageal, bladder, lung, uterus, vulva, endometrium, kidney, colorectum, pancreas, pleural/peritoneal membranes, salivary gland, and epidermous.

A compound refers to any small molecular weight compound with a molecular weight of less than about 2000 Daltons.

The term "αVβ6" refers to the heterodimer integrin molecule consisting of an αV chain and a β6 chain.

The term "neutralizing" when referring to a targeted binding agent, such as an antibody, relates to the ability of said targeted binding agent to eliminate, or significantly reduce, the activity of a target antigen. Accordingly, a "neutralizing" anti-αVβ6 antibody is capable of eliminating or significantly reducing the activity of αVβ6. A neutralizing αVβ6 antibody may, for example, act by blocking the binding of TGFβLAP to the integrin αVβ6. By blocking this binding, αVβ6 mediated cell adhesion is significantly, or completely, eliminated. Ideally, a neutralizing antibody against αVβ6 inhibits cell adhesion.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al., *Nucl. Acids Res.* 14:9081 (1986); Stec et al., *J. Am. Chem. Soc.* 106:6077 (1984); Stein et al., *Nucl. Acids Res.* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); Stec et al., U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

The term "CDR region" or "CDR" is intended to indicate the hypervariable regions of the heavy and light chains of the immunoglobulin as defined by Kabat et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Kabat et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3 (HCDR refers to a variable heavy chain CDR), and a set of LCDRs refers to LCDR1, LCDR2 and LCDR3 (LCDR refers to a variable light chain CDR). Unless otherwise stated, a "set of CDRs" includes HCDRs and LCDRs.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least about 75%, more preferably at least 80%, 90%, 95%, and most preferably about 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site.

Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., (1991) Science 253:164. Thus, the foregoing examples demonstrate that those of skill in the art can recognize sequence motifs and structural conformations that may be used to define structural and functional domains in accordance with the antibodies described herein.

A further aspect of the invention is a targeting binding agent or an antibody molecule comprising a VH domain that has at least about 60, 70, 80, 85, 90, 95, 98 or about 99% amino acid sequence identity with a VH domain of any of antibodies shown in Table 1, the appended sequence listing, an antibody described herein, or with an HCDR (e.g., HCDR1, HCDR2, or HCDR3) shown in Table 8 or Table 29. The targeting binding agent or antibody molecule may optionally also comprise a VL domain that has at least about 60, 70, 80, 85, 90, 95, 98 or about 99% amino acid sequence identity with a VL domain any of antibodies shown in Table 1, the appended sequence listing, an antibody described herein, or with an LCDR (e.g., LCDR1, LCDR2, or LCDR3) shown in Table 9 or Table 30. Algorithms that can be used to calculate % identity of two amino acid sequences comprise e.g. BLAST (Altschul et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol Biol. 147: 195-197), e.g. employing default parameters. In some embodiments, the targeting binding agent or antibody that shares amino acid sequence identity as describes above, exhibits substantially the same activity as the antibodies referenced. For instance, substantially the same activity comprises at least one activity that differed from the activity of the references antibodies by no more that about 50%, 40%, 30%, 20%, 10%, 5%, 2%, 1% or less.

An antigen binding site is generally formed by the variable heavy (VH) and variable light (VL) immunoglobulin domains, with the antigen-binding interface formed by six surface polypeptide loops, termed complimentarity determining regions (CDRs). There are three CDRs in each VH (HCDR1, HCDR2, HCDR3) and in each VL (LCDR1, LCDR2, LCDR3), together with framework regions (FRs).

Typically, a VH domain is paired with a VL domain to provide an antibody antigen-binding site, although a VH or VL domain alone may be used to bind antigen. The VH domain (e.g. from Table 1) may be paired with the VL domain (e.g. from Table 1), so that an antibody antigen-binding site is formed comprising both the VH and VL domains. Analogous embodiments are provided for the other VH and VL domains disclosed herein. In other embodiments, VH chains in Table 8 or Table 29 are paired with a heterologous VL domain. Light-chain promiscuity is well established in the art. Again, analogous embodiments are provided by the invention for the other VH and VL domains disclosed herein. Thus, the VH of the parent or of any of antibodies chain on Table 9 or Table 30 may be paired with the VL of the parent or of any of antibodies on Table 1 or other antibody.

An antigen binding site may comprise a set of H and/or L CDRs of the parent antibody or any of antibodies in Table 1 with as many as twenty, sixteen, ten, nine or fewer, e.g. one, two, three, four or five, amino acid additions, substitutions, deletions, and/or insertions within the disclosed set of H and/or L CDRs. Alternatively, an antigen binding site may comprise a set of H and/or L CDRs of the parent antibody or any of antibodies Table 1 with as many as twenty, sixteen, ten, nine or fewer, e.g. one, two, three, four or five, amino acid substitutions within the disclosed set of H and/or L CDRs. Such modifications may potentially be made at any residue within the set of CDRs.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

A further aspect of the invention is an antibody molecule comprising a VH domain that has at least about 60, 70, 80, 85, 90, 95, 98 or about 99% amino acid sequence identity with a VH domain of any of antibodies listed in Table 1, the appended sequence listing or described herein, or with an HCDR (e.g., HCDR1, HCDR2, or HCDR3) shown in Table 8 or Table 29. The antibody molecule may optionally also comprise a VL domain that has at least 60, 70, 80, 85, 90, 95, 98 or 99% amino acid sequence identity with a VL domain of any of the antibodies shown in Table 1, the appended sequence listing or described herein, or with an LCDR (e.g., LCDR1, LCDR2, or LCDR3) shown in Table 9 or Table 30. Algorithms that can be used to calculate % identity of two amino acid sequences comprise e.g. BLAST (Altschul et al., (1990) J. Mol. Biol. 215: 405-410), FASTA (Pearson and Lipman (1988) PNAS USA 85: 2444-2448), or the Smith-Waterman algorithm (Smith and Waterman (1981) J. Mol. Biol. 147: 195-197), e.g. employing default parameters.

Variants of the VH and VL domains and CDRs of the present invention, including those for which amino acid sequences are set out herein, and which can be employed in targeting agents and antibodies for αVβ6 can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate complex; ability to bind to a specified epitope; linear epitope, e.g. peptide sequence identified using peptide-binding scan as described herein, e.g. using peptides screened in linear and/or constrained conformation; conformational epitope, formed by non-continuous residues; ability to modulate a new biological activity of αVβ6, or downstream molecule. Such methods are also provided herein.

Variants of antibody molecules disclosed herein may be produced and used in the present invention. Following the lead of computational chemistry in applying multivariate data analysis techniques to the structure/property-activity relationships (Wold, et al., Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al., Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Arup K. & Viswanadhan, Vellarkad N. Combinatorial Library Design and Evaluation Principles, Software, Tools, and Applications in Drug Discovery). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule using any freely available or commercial package, such as WAM. A protein visualisation and analysis software package, such as Insight II (Accelrys, Inc.) or Deep View may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and/or binding agents generally are available in the art. Variant sequences may be made, with substitutions that may or may not be predicted to have a minimal or beneficial effect on activity, and tested for ability to bind and/or neutralize and/or for any other desired property.

Variable domain amino acid sequence variants of any of the VH and VL domains whose sequences are specifically disclosed herein may be employed in accordance with the present invention, as discussed.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least about 5, 6, 8 or 10 amino acids long, preferably at least about 14 amino acids long, more preferably at least about 20 amino acids long, usually at least about 50 amino acids long, and even more preferably at least about 70 amino acids long. The term "analog" as used herein refers to polypeptides which are comprised of a segment of at least about 25 amino acids that has substantial identity to a portion of a deduced amino acid sequence and which has at least one of the following properties: (1) specific binding to αVβ6, under suitable binding conditions, (2) ability to block appropriate ligand/αVβ6 binding, or (3) ability to inhibit αVβ6 activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.* 15:29 (1986); Veber and Freidinger *TINS* p. 392 (1985); and Evans et al., *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, a "targeted binding agent" is an agent, e.g. antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain of an antibody, wherein said domain is fused or contained within a heterologous protein.

"Binding fragments" of an antibody are produced by recombinant DNA techniques, or by enzymatic or chemical cleavage of intact antibodies. Binding fragments include Fab, Fab', $F(ab')_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulphide stabilized variable region (dsFv).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al., (1990) Nature, 348, 552-

554) the Fd fragment consisting of the VH and CH1 domains; (Holt et al., (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al., (1990) Nature, 348, 552-554, Holt et al., (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., (1988) Science, 242, 423-426, Huston et al., (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger, P. (1993) et al., Proc. Natl. Acad. Sci. USA 90 6444-6448,). Fv, scFv or diabody molecules may be stabilized by the incorporation of disulphide bridges linking the VH and VL domains (Reiter, Y. et al., Nature Biotech, 14, 1239-1245, 1996). Minibodies comprising a scFv joined to a CH3 domain may also be made (Hu, S. et al., (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≤1 μM, preferably ≤100 nM and most preferably ≤10 nM.

The term "agent" is used herein to denote a chemical compound, a mixture of chemical compounds, a biological macromolecule, or an extract made from biological materials.

"Active" or "activity" in regard to a αVβ6 heterodimeric polypeptide refers to a portion of an αVβ6 heterodimeric polypeptide that has a biological or an immunological activity of a native αVβ6 polypeptide. "Biological" when used herein refers to a biological function that results from the activity of the native αVβ6 polypeptide. A preferred αVβ6 biological activity includes, for example, αVβ6 induced cell adhesion.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a $F(ab')_2$ fragment in which the two arms of the antibody molecule remain linked and comprise two-antigen binding sites. The $F(ab')_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

The term "mAb" refers to monoclonal antibody.

"Liposome" when used herein refers to a small vesicle that may be useful for delivery of drugs that may include the αVβ6 polypeptide of the invention or antibodies to such an αVβ6 polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^{3}H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational); chemoluminescent labels or chemiluminescers, such as isoluminol, luminol and the dioxetanes; sensitizers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al., *Nature Genetics* 15:146-156 (1997) and Green and Jakobovits *J. Exp. Med.* 188:483-495 (1998). The XenoMouse® strains are available from Amgen, Inc. (Fremont, Calif.).

The production of the XenoMouse® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430, 938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al., and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al., *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. αVβ6), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to αVβ6. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the αVβ6 immunogen. The supernatants might also be screened for immunoreactivity against fragments of αVβ6 to further map the different antibodies for binding to domains of functional interest on αVβ6. The antibodies may also be screened against other related human integrins and against the rat, the mouse, and non-human primate, such as Cynomolgus monkey, orthologues of αVβ6, the last to determine species cross-reactivity. B cells from wells containing antibodies of interest may be immortalized by various methods including fusion to make hybridomas either from individual or from pooled wells, or by infection with EBV or transfection by known immortalizing genes and then plating in suitable medium. Alternatively, single plasma cells secreting antibodies with the desired specificities are then isolated using a αVβ6-specific hemolytic plaque assay (see for example Babcook et al., *Proc. Natl. Acad. Sci. USA* 93:7843-48 (1996)). Cells targeted for lysis are preferably sheep red blood cells (SRBCs) coated with the αVβ6 antigen.

In the presence of a B-cell culture containing plasma cells secreting the immunoglobulin of interest and complement, the formation of a plaque indicates specific αVβ6-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

In general, antibodies produced by the fused hybridomas were human IgG2 heavy chains with fully human kappa or lambda light chains. Antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-12}$ M or below, when measured by solid phase and solution phase techniques. Antibodies possessing a Kd of at least $10^{-11}$ M are preferred to inhibit the activity of αVβ6.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive αVβ6 binding properties.

Based on the ability of mAbs to significantly neutralize αVβ6 activity (as demonstrated in the Examples below), these antibodies will have therapeutic effects in treating symptoms and conditions resulting from αVβ6 expression. In specific embodiments, the antibodies and methods herein relate to the treatment of symptoms resulting from αVβ6 induced cell adhesion or signaling induced as a result of avb6 interaction with it s ligands According to another aspect of the invention there is provided a pharmaceutical composition comprising an antagonist of the biological activity of αVβ6, and a pharmaceutically acceptable carrier. In one embodiment the antagonist comprises an antibody. According to another aspect of the invention there is provided a pharmaceutical composition comprising an antagonist of the biological activity of αVβ6, and a pharmaceutically acceptable carrier. In one embodiment the antagonist comprises an antibody.

Anti-αVβ6 antibodies are useful in the detection of αVβ6 in patient samples and accordingly are useful as diagnostics for disease states as described herein. In addition, based on their ability to significantly inhibit αVβ6 activity (as demonstrated in the Examples below), anti-αVβ6 antibodies have therapeutic effects in treating symptoms and conditions resulting from αVβ6 expression. In specific embodiments, the antibodies and methods herein relate to the treatment of symptoms resulting from αVβ6 induced cell adhesion. Further embodiments involve using the antibodies and methods described herein to treat an αVβ6 related disease or disorder including neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, and pancreatic cancer.

Therapeutic Administration and Formulations

Embodiments of the invention include sterile pharmaceutical formulations of anti-αVβ6 antibodies that are useful as treatments for diseases. Such formulations would inhibit the binding of ligands to the αVβ6 integrin, thereby effectively treating pathological conditions where, for example, tissue αVβ6 is abnormally elevated. Anti-αVβ6 antibodies preferably possess adequate affinity to potently inhibit αVβ6 activity, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumor site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* ($20^{th}$ ed, Lippincott Williams & Wilkens Publishers (2003)). For example, dissolution or suspension of the active compound in a pharmaceutically acceptable carrier such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

The antibodies of the invention also encompass antibodies that have half-lives (e.g., serum half-lives) in a mammal, preferably a human, of greater than that of an unmodified antibody. In one embodiment, said antibody anybody half life is greater than days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J. Pharm Sci.* 89(8):967-78 (2000), Powell et al., "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to αVβ6, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, generation of peptide therapeutics, αVβ6 binding domains in novel scaffolds, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

Bispecific antibodies can be generated that comprise (i) two antibodies one with a specificity to αVβ6 and another to a second molecule that are conjugated together, (ii) a single antibody that has one chain specific to αVβ6 and a second chain specific to a second molecule, or (iii) a single chain antibody that has specificity to αVβ6 and the other molecule. Such bispecific antibodies can be generated using techniques that are well known; for example, in connection with (i) and (ii) see e.g., Fanger et al., *Immunol Methods* 4:72-81 (1994) and Wright and Harris, supra. and in connection with (iii) see e.g., Traunecker et al., *Int. J. Cancer* (*Suppl.*) 7:51-52 (1992). In each case, the second specificity can be made to the heavy chain activation receptors, including, without limitation, CD16 or CD64 (see e.g., Deo et al., *Immunol. Today* 18:127 (1997)) or CD89 (see e.g., Valerius et al., *Blood* 90:4485-4492 (1997)).

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al., in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902.

An antigen binding site may be provided by means of arrangement of CDRs on non-antibody protein scaffolds, such as fibronectin or cytochrome B etc. (Haan & Maggos (2004) BioCentury, 12(5): A1-A6; Koide et al., (1998) Journal of Molecular Biology, 284: 1141-1151; Nygren et al., (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al., (Nygren et al., (1997) Current Opinion in Structural Biology, 7: 463-469). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding agent may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12(42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding agent according to the present invention may comprise other amino acids, e.g. forming a peptide or polypeptide, such as a folded domain, or to impart to the molecule another functional characteristic in addition to ability to bind antigen. Binding agents of the invention may carry a detectable label, or may be conjugated to a toxin or a targeting moiety or enzyme (e.g. via a peptidyl bond or linker). For example, a binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Combinations

The anti-tumor treatment defined herein may be applied as a sole therapy or may involve, in addition to the compounds of the invention, conventional surgery or radiotherapy or chemotherapy. Such chemotherapy may include one or more of the following categories of anti tumor agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-EGFR inhibitor Bevacizumab (Avastin™), the anti-erbB1 antibody cetuximab [Erbitux, C225] and any growth factor or growth factor receptor antibodies disclosed by Stem et al., Critical reviews in oncology/haematology, 2005, Vol. 54, pp11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunization

Immunizations were conducted using soluble αVβ6 and cell-bound αVβ6 (CHO transfectants expressing human αVβ6 at the cell surface), respectively. For the generation of CHO transfectants, human full length αVβ6 cDNA was inserted into the pcDNA 3 expression vector. CHO cells were transiently transfected via electroporation. Expression of human αVβ6 on the cell surface at the level suitable for immunogen purpose was confirmed by Fluorescene-Activated Cell Sorter (FACS) analysis. Ten fig/mouse of soluble protein for Campaign 1, and $3\times10^6$ cells/mouse of transfected CHO cells for Campaign 2, were used for initial immunization in XenoMouse™ according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. Following the initial immunization, thirteen subsequent boost immunizations of five µg/mouse were administered for groups one and two (soluble antigen), and nine subsequent boost immunizations of $1.5\times10^6$ cells/mouse were administered for groups three and four (cell-bound antigen). The immunization programs are summarized in Table 2.

TABLE 2

Summary of Immunization Programs

| Campaign | Group | Immunogen | Strain | No of mice | Immunization routes |
|---|---|---|---|---|---|
| 1 | 1 | Soluble αVβ6 | XMG2/k | 10 | IP, Tail, BIP, twice/wk, x 6wks |
| 1 | 2 | Soluble αVβ6 | XMG1/kl | 10 | IP, Tail, BIP, twice/wk, x 6wks |
| 2 | 3 | Cell-bound αVβ6 (CHO transfectants) | XMG2/k | 10 | IP, Tail, BIP, twice/wk, x 6wks |
| 2 | 4 | Cell-bound αVβ6 (CHO transfectants) | XMG1/kl | 10 | IP, Tail, BIP, twice/wk, x 6wks |

Selection of Animals for Harvest by Titer

Titers of the antibody against human αVβ6 were tested by ELISA assay for mice immunized with soluble antigen. Titers of the antibody for mice immunized with native (cell-bound) antigen were tested by FACS. The ELISA and FACS analyses showed that there were some mice which appeared to be specific for αVβ6. Therefore, at the end of the immunization program, twenty mice were selected for harvest, and lymphocytes were isolated from the spleens and lymph nodes of the immunized mice, as described in Example 2.

Example 2

Recovery of Lymphocytes and B-Cell Isolations

Immunized mice were sacrificed by cervical dislocation, and the draining lymph nodes harvested and pooled from each cohort. The lymphoid cells were dissociated by grinding in DMEM to release the cells from the tissues and the cells were suspended in DMEM. B cells were enriched by negative selection in IgM and positive selection on IgG. The cells were cultured to allow B cell expansion and differentiation into antibody-secreting plasma cells.

Antibody-secreting plasma cells were grown as routine in the selective medium. Exhaustive supernatants collected from the cells that potentially produce anti-human αVβ6 antibodies were subjected to subsequent screening assays as detailed in the examples below.

Example 3

Binding to Cell-Bound αVβ6

The binding of secreted antibodies to αVβ6 was assessed. Binding to cell-bound αVβ6 was assessed using an FMAT macroconfocal scanner, and binding to soluble αVβ6 was analyzed by ELISA, as described below.

Supernatants collected from harvested cells were tested to assess the binding of secreted antibodies to HEK 293 cells stably overexpressing αVβ6. A parental 293F cell line was used as a negative control. Cells in Freestyle media (Invitrogen) were seeded into 384-well FMAT plates in a volume of 50 µL/well at a density of 2500 cells/well for the stable transfectants, and at a density of 22,500 cells/well for the parental cells, and cells were incubated overnight at 37° C. Then, 10 µL/well of supernatant was added, and plates were incubated for approximately one hour at 4° C., after which 10 µL/well of anti-human IgG-Cy5 secondary antibody was added at a concentration of 2.8 µg/ml (400 ng/ml final concentration). Plates were then incubated for one hour at 4° C., and fluorescence was read using an FMAT macroconfocal scanner (Applied Biosystems). FMAT results for 11 antibodies are summarized in Table 3.

Additionally, antibody binding to soluble αVβ6 was analyzed by ELISA. Costar medium binding 96-well plates (Costar catalog #3368) were coated by incubating overnight at 4° C. with αVβ6 at a concentration of 5 µg/ml in TBS/1 mM $MgCl_2$ buffer for a total volume of 50 µL/well. Plates were then washed with TBS/1 mM $MgCl_2$ buffer, and blocked with 250 µL of 1×PBS/1% milk for thirty minutes at room temperature. Ten µL of supernatant was then added to 40 µL TBS/1 mM $MgCl_2$/1% milk and incubated for one hour at room temperature. Plates were washed and then incubated with goat-anti-human IgG Fc-peroxidase at 0.400 ng/ml in TBS/1 mM $MgCl_2$/1% milk, and incubated for one hour at room temperature. Plates were washed and then developed with 1-Step TMB substrate. The ELISA results for one of the antibodies are shown in Table 3.

TABLE 3

Binding of Supernatants to Cell-Bound and Soluble αVβ6

| mAb | FMAT Data | | | ELISA data |
|---|---|---|---|---|
| | Count | FL1 | FL1XCount | OD |
| sc 049 | 185 | 4377.73 | 809880 | ND |
| sc 058 | ND | ND | ND | 1.79 |
| sc 188 | 127 | 628.04 | 79761 | ND |
| sc 097 | 98 | 1237.18 | 121243 | ND |
| sc 277 | 28 | 382.31 | 10704 | ND |
| sc 133 | 82 | 709.82 | 58205 | ND |
| sc 161 | 23 | 725.21 | 16679 | ND |
| sc 254 | 174 | 9179.65 | 1597259 | ND |

TABLE 3-continued

| Binding of Supernatants to Cell-Bound and Soluble αVβ6 | | | | |
|---|---|---|---|---|
| | FMAT Data | | | ELISA data |
| mAb | Count | FL1 | FL1XCount | OD |
| sc 264 | 63 | 734.29 | 46260 | ND |
| sc 298 | 102 | 2137.94 | 218069 | ND |
| sc 374 | 174 | 4549.65 | 791639 | ND |
| sc 320 | 141 | 3014.63 | 425062 | ND |
| Negative Control (Blank): | 0 | 0 | 0 | 0.21 |
| Positive Control (2077z-1 ug/mL): | 67 | 659.49 | 44185 | 6.00 |

Example 4

Inhibition of Cell Adhesion

In order to determine the relative potency of the different antibody-containing supernatants, the antibodies were assessed for their ability to inhibit TGFβLAP-mediated adhesion of αVβ6-positive HT29 cells. Plates were coated overnight with 10 g/ml TGFβLAP, and pre-blocked with 3% BSA/PBS for 1 hour prior to the assay. Cells were then pelleted and washed twice in HBBS, after which the cells were then resuspended in HBSS at appropriate concentrations. The cells were incubated in the presence of appropriate antibodies at 4° C. for 30 minutes in a V-bottom plate. The antigen coating solution was removed and the plates were blocked with 100 μL of 3% BSA for one hour at room temperature. Plates were washed twice with PBS or HBSS, and the cell-antibody mixtures were transferred to the coated plate and the plate was incubated at 37° C. for 30 minutes. The cells on the coated plates were then washed four times in warm HBSS, and the cells were thereafter frozen at −80° C. for one hour. The cells were allowed to thaw at room temperature for one hour, and then 100 μL of CyQuant dye/lysis buffer (Molecular Probes) was added to each well according to the manufacturer's instructions. Fluorescence was read at an excitation wavelength of 485 nm and an emission wavelength of 530 nm. The results for twelve antibodies are summarized in Table 4. Those antibodies shown ranged in potency from 62% inhibition to over 100% inhibition, relative to coated and uncoated control wells on the plate which were used to represent the maximum and minimum adhesion values that could be obtained in the assay.

TABLE 4

| Adhesion Assay | | | |
|---|---|---|---|
| Antibody ID | Assay 1% Inhibition | Assay 2% Inhibition | Average Inhibition |
| sc 049 | 80% | 98% | 89% |
| sc 058 | 77% | 46% | 62% |
| sc 097 | 96% | 106% | 101% |
| sc 133 | 99% | 106% | 103% |
| sc 161 | 98% | 106% | 102% |
| sc 188 | 99% | 103% | 101% |
| sc 254 | 98% | 106% | 102% |
| sc 264 | 98% | 100% | 99% |
| sc 277 | 98% | 101% | 100% |
| sc 298 | 98% | 102% | 100% |
| sc 320 | 97% | 97% | 97% |
| sc 374 | 118% | 89% | 104% |

Example 5

Cross-Reactivity to Macaque αVβ6 and Human αV

Cross-reactivity of the antibody-containing supernatants to macaque αVβ6 was tested on the supernatants using FACS analysis on HEK-293 cells transiently transfected with cynomolgus αV and cynomolgus β6.

Cross-reactivity to human αV was also tested. For this assay, cross-reactivity was tested on the supernatants using FACS analysis on parental A375M cells, which express αVβ3 and αVβ5, but not αVβ6. This screen was designed to show that the antibodies were specifically recognizing either the β6 chain or the β6 chain in combination with αV. The human αV assay was run at the same time as the macaque αVβ6 cross-reactivity screen.

The assays were performed as follows. A375M cells that were approximately 75% confluent were labeled with CFSE intracellular dye by dissociating and then pelleting cells (equivalent to 250,000 to 300,000 cells per well) in a falcon tube, then resuspending in 0.125 μM CFSE in FACS buffer to a final volume of 100 μL for every 250,000 cells, and then by incubating at 37° C. for five minutes. The cells were then pelleted, the supernatant discarded, and resuspended in FACS buffer and incubated for 30 minutes at 37° C. Cells were then washed twice with FACS buffer and resuspended in a final volume of 100 μL FACS buffer per well.

HEK-293 cells were transiently transfected with cynomolgus αV and cynomolgus β6. After 48 hours, the cells were collected and resuspended in FACS buffer to reach a final concentration of approximately 50,000 cells in 100 μL.

Approximately 100,000 cells total, comprising a 50:50 mix of CFSE-labeled A375M cells and transfected 293 cells, were used in each reaction as follows. 100 μL of CFSE-labeled A375M cells and 100 μL of 293 cells were dispensed into a V-bottom plate. The cells in the plate were pelleted at 1500 rpm for 3 minutes, and then resuspended in 100 μL FACS buffer. The pelleting step was repeated, and the FACS buffer supernatant was removed. The harvested antibody-containing supernatants, or control primary antibodies were added in a volume of 50 μL and the cells were resuspended. Primary antibody controls were murine αVβ6 (Cat#MAB2077z, Chemicon) and an anti-αV recombinant. The plate was incubated on ice for 45 minutes, after which 100 μL FACS buffer was added to dilute the primary antibody. The cells were then pelleted by centrifuging at 1500 rpm for 3 minutes, and the pellet was resuspended in 100 μL FACS buffer. The pelleting step was repeated, and the FACS buffer supernatant was removed. Cells were then resuspended in the appropriate secondary antibody (5 μg/ml) with 7AAD dye (10 μg/ml), and stained on ice for 7 minutes. Then 150 μL of FACS buffer was added and the cells were pelLeted at 1500 rpm for 3 minutes, after which the cells were washed in 100 μL FACS buffer, pelleted, and then resuspended in 250 μL buffer and added to FACS tubes. Samples were analyzed on a high throughput FACS machine and analyzed using Cell Quest Pro software.

The results for twelve antibodies are summarized in Table 5, and demonstrate that the antibodies shown were able to specifically bind to macaque αVβ6 but were not able to non-specifically bind human αV on the parental A375M cells.

TABLE 5

Cross-Reactivity to Macaque αVβ6 and Human αV

| Antibody ID | Mac αVβ6 % Cells Shifted | Mac AVB6 GeoMean | A375M % Cells Shifted | A375M GeoMean |
|---|---|---|---|---|
| sc 049 | 23% | 30.19 | 20% | 1.74 |
| sc 058 | 25% | 22.77 | 18% | 1.78 |
| sc 097 | 35% | 37.04 | 24% | 1.84 |
| sc 133 | 32% | 35.22 | 24% | 1.79 |
| sc 161 | 14% | 32.98 | 11% | 16.68 |
| sc 188 | 18% | 23.9 | 13% | 1.65 |
| sc 254 | 59% | 78.49 | 55% | 2.31 |
| sc 264 | 55% | 66.38 | 46% | 2.35 |
| sc 277 | 35% | 33.35 | 23% | 1.86 |
| sc 298 | 53% | 63.08 | 45% | 2.14 |
| sc 320 | 19% | 33.45 | 15% | 23.18 |
| sc 374 | 51% | 61.79 | 39% | 2.14 |
| Human IgG Isotype Control | 1% (day 1) 0% (day 2) | 9.54 (day 1) 7.39 (day 2) | 5% (day 1) 1% (day 2) | 1.66 (day 1) 7.23 (day 2) |
| Mouse IgG2 with Murine Secondary Antibody | 1% (day 1) 0% (day 2) | 8.85 (day 1) 11.21 (day 2) | 4% (day 1) 3% (day 2) | 1.67 (day 1) 11.16 (day 2) |
| Positive Control 2077z (1ug/ml) | 42% (day 1) 11% (day 2) | 55.52 (day 1) 28.11 (day 2) | 30% (day 1) 5% (day 2) | 2.03 (day 1) 15.36 (day 2) |

Example 6

αVβ6-Specific Hemolytic Plaque Assay

Antibody-secreting plasma cells were selected from each harvest for the production of recombinant antibodies. Here, a fluorescent plaque assay was used to identify single plasma cells expressing antibodies against αVβ6. Then, the single cells were subjected to reverse transcription and polymerase chain reaction to rescue and amplify the variable heavy and variable light chains that encoded the initial antibody specificity, as described in Example 7. The preparation of a number of specialized reagents and materials needed to conduct the αVβ6-specific hemolytic plaque assay are described below.

Biotinylation of Sheep Red Blood Cells (SRBC).

SRBC were stored in RPMI media as a 25% stock. A 250 μl SRBC packed-cell pellet was obtained by aliquoting 1.0 mL of the stock into a 15-mL falcon tube, spinning down the cells and removing the supernatant. The cell pellet was then re-suspended in 4.75 mL PBS at pH 8.6 in a 50 mL tube. In a separate 50 mL tube, 2.5 mg of Sulfo-NHS biotin was added to 45 mL of PBS at pH 8.6. Once the biotin had completely dissolved, 5 mL of SRBCs was added and the tube was rotated at room temperature for 1 hour. The SRBCs were centrifuged at 3000 g for 5 minutes. The supernatant was drawn off and 25 mL PBS at pH 7.4 was added as a wash. The wash cycle was repeated 3 times, then 4.75 mL immune cell media (RPMI 1640 with 10% FCS) was added to the 250 μl biotinylated-SRBC (B-SRBC) pellet to gently re-suspend the B-SRBC (5% B-SRBC stock). The stock was stored at 40° C. until needed.

Streptavidin (SA) Coating of B-SRBC.

One mL of the 5% B-SRBC stock was transferred into to a fresh eppendorf tube. The B-SRBC cells were pelleted with a pulse spin at 8000 rpm (6800 rcf) in a microfuge. The supernatant was then drawn off, the pellet was re-suspended in 1.0 mL PBS at pH 7.4, and the centrifugation was repeated. The wash cycle was repeated 2 times, then the B-SRBC pellet was resuspended in 1.0 mL of PBS at pH 7.4 to give a final concentration of 5% (v/v). 10 μl of a 10 mg/mL Streptavidin (CalBiochem, San Diego, Calif.) stock solution was added. The tube was mixed and rotated at RT for 20 minutes. The washing steps were repeated and the SA-SRBC were re-suspended in 1 mL PBS pH 7.4 (5% (v/v)).

Human αVβ6 Coating of SA-SRBC.

Soluble antigen (lacking the transmembrane domain) was used for coating the SRBC. Both chains were used because αVβ6 is only presented on the cell surface as a dimer. The SA-SRBC were coated with the biotinylated-αVβ6 at 50 μg/mL, mixed and rotated at room temperature for 20 minutes. The SRBC were washed twice with 1.0 mL of PBS at pH 7.4 as above. The Ag-coated SRBC were re-suspended in RPMI (+10% FCS) to a final concentration of 5% (v/v).

Determination of the Quality of αV/36-SRBC by Immunofluorescence (IF).

10 μl of 5% SA-SRBC and 10 μl of 5% Ag-coated SRBC were each added to separate fresh 1.5 mL eppendorf tube containing 40 μl of PBS. Human anti-αVβ6 antibodies were added to each sample of SRBCs at 50 μg/mL. The tubes were rotated at room temperature for 25 min, and the cells were then washed three times with 100 μl of PBS. The cells were re-suspended in 50 μl of PBS and incubated with 2 μg/mL Gt-anti Human IgG Fc antibody conjugated to the photostable fluorescent dye Alexa488 (Molecular Probes, Eugene, Oreg.). The tubes were rotated at room temperature for 25 min, followed by washing with 100 μl PBS and re-suspension in 10 μl PBS. 10 μl of the stained cells were spotted onto a clean glass microscope slide, covered with a glass coverslip, observed under fluorescent light, and scored on an arbitrary scale of 0-4 to assess the quality of the isolated cells.

Preparation of Plasma Cells.

The contents of a single B cell culture well previously identified as neutralizing for αVβ6 activity (therefore containing a B cell clone secreting the immunoglobulin of interest), was harvested. The B cell culture present in the well was recovered by addition of RPMI+10% FCS at 37° C. The cells were re-suspended by pipetting and then transferred to a fresh 1.5 mL eppendorf tube (final volume approximately 500-700 μl). The cells were centrifuged in a microfuge at 1500 rpm (240 rcf) for 2 minutes at room temperature, then the tube was rotated 180 degrees and centrifuged again for 2 minutes at 1500 rpm. The freeze media was drawn off and the immune cells were resuspended in 100 μl RPMI (10% FCS), then centrifuged. This washing with RPMI (10% FCS) was repeated and the cells re-suspended in 60 μl RPMI (FCS) and stored on ice until ready to use.

Performance of the Hemolytic Plaque Assay.

To the 60 μl sample of immune cells was added 60 μl each of αVβ6-coated SRBC (5% v/v stock), 4× guinea pig complement (Sigma, Oakville, ON) stock prepared in RPMI (FCS), and 4× enhancing sera stock (1:900 in RPMI (FCS)). The mixture (3-5 μl) was spotted onto plastic lids from 100 mm Falcon tissue culture plates and the spots were covered with undiluted paraffin oil. The slides were incubated at 37° C. for a minimum of 45 minutes.

Analysis of Plaque Assay Results.

The coating of the sheep red blood cells with the catalytic domain of human αVβ6 was successful. These Ag-coated red blood cells were then used to identify antigen-specific plasma cells from the wells shown below in Table 6. These cells were then isolated by micromanipulation. After micromanipulation to rescue the antigen-specific plasma cells, the genes encoding the variable region genes were rescued by RT-PCR on a single plasma cell, as described further in Example 7.

TABLE 6

| Plaque Assay Results | | | | |
|---|---|---|---|---|
| Parent Plate ID | | | Plaque Assay | |
| Plate | Row | Column | Assay | Single Cells |
| 68 | B | 10 | Fluorescent | 45-57 |
| 296 | D | 10 | Fluorescent | 58-59 |
| 318 | F | 1 | Hemolytic | 60-62 |
| 612 | G | 1 | Fluorescent | 187-189 |
| 752 | D | 12 | Fluorescent | 95-100 |
| 762 | D | 8 | Fluorescent | 277-286 |
| 766 | B | 5 | Fluorescent | 132-143, 147-150 |
| 827 | E | 12 | Fluorescent | 159-170 |
| 659 | F | 11 | Fluorescent | 252-263 |
| 761 | H | 3 | Fluorescent | 264-276 |
| 765 | A | 8 | Fluorescent | 287-298 |
| 652 | D | 2 | Fluorescent | 374-379, 392-397 |
| 806 | A | 6 | Fluorescent | 312-321 |

Example 7

Recombinant Protein Isolation

After isolation of the desired single plasma cells from Example 4, mRNA was extracted and reverse transcriptase PCR was conducted to generate cDNA encoding the variable heavy and light chains of the antibody secreted by each cell. The human variable heavy chain cDNA was digested with restriction enzymes that were added during the PCR and the products of this reaction were cloned into an IgG2 expression vector with compatible overhangs for cloning. This vector was generated by cloning the constant domain of human IgG2 into the multiple cloning site of pcDNA3.1+/Hygro (Invitrogen, Burlington, Ontario, Canada). The human variable light chain cDNA was digested with restriction enzymes that were added during the PCR reaction and the products of this reaction were cloned into an IgKappa or IgLamda expression vector with compatible overhangs for cloning. This vector was generated by cloning the constant domain of human IgK or IgL into the multiple cloning site of pcDNA3.1+/Neo (Invitrogen).

The heavy chain and the light chain expression vectors were then co-transfected using lipofectamine into a 60 mm dish of 70% confluent human embryonal kidney (HEK) 293 cells. The transfected cells secreted a recombinant antibody with the identical specificity as the original plasma cell for 24 to 72 hours. The supernatant (3 mL) was harvested from the HEK 293 cells and the secretion of an intact antibody was demonstrated with a sandwich ELISA to specifically detect human IgG. Specificity was confirmed through binding of the recombinant antibody to αVβ6 using ELISA. The rescued clones secreting antibody that could bind to the target antigen are summarized in Table 7.

TABLE 7

| Secretion and Binding Data for the Recombinant Antibodies | | | |
|---|---|---|---|
| Parent Plate ID Plate | Row | Column | Antibody ID |
| 68 | B | 10 | 49 |
| 296 | D | 10 | 58 |
| 612 | G | 1 | 188 |

TABLE 7-continued

| Secretion and Binding Data for the Recombinant Antibodies | | | |
|---|---|---|---|
| Parent Plate ID Plate | Row | Column | Antibody ID |
| 752 | D | 12 | 97 |
| 762 | D | 8 | 277 |
| 766 | B | 5 | 133 |
| 827 | E | 12 | 161 |
| 659 | F | 11 | 254 |
| 761 | H | 3 | 264 |
| 765 | A | 8 | 298 |
| 652 | D | 2 | 374 |
| 806 | A | 6 | 320 |

Example 8

Purification of Recombinant Antibodies

For larger scale production of the anti-αVβ6 antibodies, heavy and light chain expression vectors (2.5 g of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). The antibodies were purified from the supernatant using Protein-A Sepharose (Amersham Biosciences, Piscataway, N.J.) affinity chromatography (1 mL). The antibodies were eluted from the Protein-A column with 500 μL of 0.1 M Glycine pH 2.5. The eluate was dialyzed in PBS pH 7.4 and filter sterilized. The antibodies were analyzed by non-reducing SDS-PAGE to assess purity and yield. Protein concentration was determined by determining the optical density at 280 nm.

Example 9

Structural Analysis of αVβ6 Antibodies

The variable heavy chains and the variable light chains of the antibodies were sequenced to determine their DNA sequences. The complete sequence information for the anti-αVβ6 antibodies is provided in the sequence listing with nucleotide and amino acid sequences for each gamma and kappa/lambda chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 8 is a table comparing the antibody heavy chain regions to their cognate germ line heavy chain region. Table 9 is a table comparing the antibody kappa or lambda light chain regions to their cognate germ line light chain region.

The variable (V) regions of immunoglobulin chains are encoded by multiple germ line DNA segments, which are joined into functional variable regions ($V_HDJ_H$ or $V_KJ_K$) during B-cell ontogeny. The molecular and genetic diversity of the antibody response to αVβ6 was studied in detail. These assays revealed several points specific to anti-αVβ6 antibodies.

According the sequencing data, the primary structure of the heavy chains of sc 298 and sc 374 are similar, but not identical. sc 254 is structurally different from the other two. It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 9 shows that the light chain sequence of sc 298 (SEQ ID NO.: 40) differs from the corresponding germline sequence (SEQ ID NO.:68) by a Val to Ala mutation (mutation 1) in the FR1 region, via a Leu to Ala mutation (mutation 2) in the CDR1 region and an Asn to Ser in the FR3 region. Thus, the amino acid or nucleotide sequence encoding the light chain of sc 298 can be modified to change mutation 1 to yield the germline sequence at the site of mutation 1. Further, the amino acid or nucleotide sequence encoding the light chain of mAb sc 298 can be modified to change mutation 2 to yield the germline sequence at the site of mutation 2. Still further, the amino acid or nucleotide sequence encoding the light chain of mAb sc 298 can be modified to change mutation 3 to yield the germline sequence at the site of mutation 3. Still further again, the amino acid or nucleotide sequence encoding the light chain of sc 298 can be modified to change mutation 1, mutation 2 and mutation 3 to yield the germline sequence at the sites of mutations 1, 2 and 3. Still further again, the amino acid or nucleotide sequence encoding the light chain of sc 298 can be modified to change any combination of mutation 1, mutation 2 and mutation 3. In another example, heavy chain of sc 264 (SEQ ID NO: 30) differs from it's germline (SEQ ID NO: 55) at position 61. Thus the amino acid or nucleotide sequence encoding the heavy chain of sc 264 can be modified from a N to Y to yield the germline sequence. Tables 10-13 below illustrate the position of such variations from the germline for sc 133, sc 188 and sc 264. Each row represents a unique combination of germline and non-germline residues at the position indicated by bold type. Particular examples of an antibody sequence that can be mutated back to the germline sequence include: sc 133 where the L at amino acid 70 of the heavy chain is mutated back to the germline amino acid of M (referred to herein as sc 133 TMT); sc 133 where the N at amino acid 93 of the light chain is mutated back to the germline amino acid of D (referred to herein as sc 133 WDS); and sc 264 where the A at amino acid 84 of the light chain is mutated back to the germline amino acid of D (referred to herein as sc 264 ADY).

In one embodiment, the invention features modifying one or more of the amino acids in the CDR regions, i.e., CDR1, CDR2 and/or CDR3. In one example, the CDR3 of the heavy chain of an antibody described herein is modified. Typically, the amino acid is substituted with an amino acid having a similar side chain (a conservative amino acid substitution) or can be substituted with any appropriate amino acid such as an alanine or a leucine. In one embodiment, the sc 264 CDR3, VATGRGDYHFYAMDV (amino acid residues 100-114 of SEQ ID NO: 30), can be modified at one or more amino acids. Applicants have already demonstrated that the CDR3 region can be modified without adversely affecting activity, i.e., see sc 264 RAD where the second G in the CDR3 region is substituted for an A. Other modifications within the CDR3 region are also envisaged. In another embodiment, the sc 133 CDR3 region, RLDV, can be modified at one or more amino acids including substituting the L for an A and/or the V for an A. Means of substituting amino acids are well known in the art and include site-directed mutagenesis.

In another embodiment, the invention includes replacing any structural liabilities in the sequence that might affect the heterogeneity or specificity of binding of the antibodies of the invention. In one example, the antibody sc 264 has an RGD sequence in the CDR3 region that might cause cross-reactive binding. Therefore the glycine residue in the RGD can be replaced with an alanine (sc 264 RAD).

TABLE 8

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| | 49 | | Germline | | QVQLVQSGAEVKK<br>PGASVKVSCKAS | GYTFTG<br>YYMH | WVRQAPG<br>QGLEWMG | WINPNSGGT<br>NYAQKFQG | RVTMTRDTSISTAYME<br>LSRLRSDDTAVYYCAR | RL-- | WGQGTT<br>VTVSS |
| sc 133 | 14 | VH1-2 | 5-12 | JH6B | QVQLVQSGAEVKK<br>PGASVKVSCKAS | GYTFTG<br>YYMH | WVRQAPG<br>QGLEWMG | WINPKSGDT<br>NYAQKFQG | RVTLTRDTSTSTAYME<br>LSRLRSDDTAVYYCAR | RLDV | WGQGTT<br>VTVSS |
| | 50 | | Germline | | EVQLVESGGGLVK<br>PGGSLRLSCAAS | GFTFSS<br>YSMN | WVRQAPG<br>KGLEWVS | SISSSSSYI<br>YYADSVKG | RFTISRDNAKNSLYLQ<br>MNSLRAEDTAVYYCAR | --VQLE<br>RYYYY<br>YGMDV | WGQGTT<br>VTVSS |
| sc 320 | 42 | VH3-21 | D1-1 | JH6B | EVQLVESGGGLVK<br>PGGSLRLSCAAS | GYTFTN<br>YIMH | WVRQAPG<br>KGLEWVS | SISISSSYI<br>YYADSVKG | RFTISRDNAKNSLYLQ<br>MNSLRAEDTAVYYCAR | DPVPLE<br>RRDYY<br>YGMDV | WGQGTT<br>VTVSS |
| | 51 | | Germline | | EVQLLESGGGLVQ<br>PGGSLRLSCAAS | GFTFSS<br>YAMS | WVRQAPG<br>KGLEWVS | AISGSGGST<br>YYADSVKG | RFTISRDNSKNTLYLQ<br>MNSLRAEDTAVYYCAK | -VDTA<br>MVYYG<br>MDV | WGQGTT<br>VTVSS |
| sc 58 | 6 | VH3-23 | D5-5 | JH6B | EVQLLESGGGLVQ<br>PGGSLRLSCAAS | GFTFSS<br>YVMS | WVRQAPG<br>KGLEWVS | AISGSGGST<br>YYADSVKG | RFTISRDNSKNTLYLQ<br>MNSLRAEDTAVYYCAK | GVDTAMV<br>TYGMDV | WGQGTT<br>VTVSS |
| | 52 | | Germline | | QVQLVESGGGVVQ<br>PGRSLRLSCAAS | GFTFSS<br>YGMH | WVRQAPG<br>KGLEWVA | VIWYDGSNK<br>YYADSVKG | RFTISRDNSKNTLYLQ<br>MNSLRAEDTAVYYCAR | -IAA<br>R--YYY<br>YGMDV | WGQGTT<br>VTVSS |
| sc 298 | 38 | VH3-33 | D6-6 | JH6B | QVQLVESGGGVVQ<br>PGRSLRLSCAAS | GFTFSS<br>YGMH | WVRQAPG<br>KGLEWVA | VIWYGGSNK<br>YYADSVKG | RFTISRDNSKNTLYLQ<br>MNSLRAEDTAVYYCAR | DLAAR<br>RGDYYY<br>YGMDV | WGQGTT<br>VTVSS |

TABLE 8 -continued

| Heavy chain analysis | | | | | | | | | | | |
|---|---|---|---|---|---|---|---|---|---|---|---|
| Chain Name | SEQ ID NO: | V | D | J | FR1 | CDR1 | FR2 | CDR2 | FR3 | CDR3 | FR4 |
| sc 374 | 46 | VH3-33 | D6-6 | JH6B | QVQLVESGGGVVQPGRSLRLSCAAS | GFTFSSYGMH | WVRQAPGKGLEWVA | VIWYDGSNKYYADSVKG | RFTISRDNSKNTLYLQMNSLRAEDTAVYYCAR | TEGIAARLYYYYGMDV | WGQGTTVTVSS |
| | 53 | | Germline | | QVQLQESGPGLVKPSQTLSLTCTVS | GGSISSGGYYWS | WIRQHPGKGLEWIG | YIYYSGSTYYNPSLKS | RVTISVDTSKNQFSLKLSSVTAADTAVYYCAR | --GIAAAG--YYYYYGMDV | WGQGTTVTVSS |
| sc 254 | 26 | VH4-31 | D6-13 | JH6B | QVQLQESGPGLVKPSQTLSLTCTVS | GGSISSGGYYWS | WIRQHPGKGLEWIG | YIYYSGSTYYNPSLKS | RVTISVDTSKNQFSLKLSSVTAADTAMYYCAR | YRGPAAGRGDFYYFGMDV | WGQGTTVTVSS |
| | 54 | | Germline | | QVQLQESGPGLVKPSQTLSLTCTVS | GGSISSGGYYWS | WIRQHPGKGLEWIG | YIYYSGSTYYNPSLKS | RVTISVDTSKNQFSLKLSSVTAADTAVYYCAR | ---ITIFGVFDY | WGQGTLVTVSS |
| sc 49 | 2 | VH4-31 | D3-3 | JH4B | QVQLQESGPGLVKPSQTLSLTCTVA | GGSIRSGDYYWS | WIRQHPGKGLEWIG | NIYYSGSTYYNPSLKS | RITISVATSRNQFSLKLTSVTAADTAVYYCAR | GGAITIFGVFDY | WGQGTLVTVSS |
| | 55 | | Germline | | QVQLQESGPGLVKPSQTLSLTCTVS | GGSISSGGYYWS | WIRQHPGKGLEWIG | YIYYSGSTYYNPSLKS | RVTISVDTSKNQFSLKLSSVTAADTAVYYCAR | VAT---YYYYYGMDV | WGQGTTVTVSS |
| Sc 264 | 30 | VH4-31 | D4-17 | JH6B | QVQLQESGPGLVKPSQTLSLTCTVS | GGSISSGGYYWS | WIRQHPGKGLEWIG | YIYYSGRTYNNPSLKS | RVTISVDTSKNQFSLKLSSVTAADTAVYYCAR | VATGRGDYHFYAMDV | WGQGTTVTVSS |
| | 56 | | Germline | | QVQLQESGPGLVKPSQTLSLTCTVS | GGSISSGGYYWS | WIRQHPGKGLEWIG | YIYYSGSTYYNPSLKS | RVTISVDTSKNQFSLKLSSVTAADTAVYYCAR | ---LRYYYYYGMDV | WGQGTTVTVSS |
| Sc 188 | 22 | VH4-31 | D4-23 | JH6B | QVQLQESGPGLVKPSQTLSLTCTVS | GGSISSGVYYWT | WIRQHPGNGLEWIG | YIYYSGSTSYNPSLKS | RVTISVDTSKKQFSLNLTSVTAADTAVYYCAR | EGPLRGDYYYGLDV | WGQGTTVTVSS |
| | 57 | | Germline | | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | ---SSGYYYAFDI | WGQGTMVTVSSA |
| Sc 97 | 10 | VH5-51 | D3-22 | JH3B | EVQLVQSGAEVKKPGESLKISCKGS | GYSFTSYWIG | WVRQMPGKGLEWMG | IIYPGDSDTRYSPSFQG | QVILSADKSISTAYLQWSSLKASDTAMYYCAR | HDESSGYYYVFDI | WGQGTMVTVSSA |
| | 58 | | Germline | | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | -----GMDV | WGQGTTVTVSS |
| Sc 277 | 34 | VH5-51 | D3-10 | JH6B | EVQLVQSGAEVKKPGESLKISCKGS | GYSFPSYWIG | WVRQMPGKGLEWMG | IIYPGDSDTRYSPSFQG | QVTISADKSISTAYLQWSSLKASDTAMYYCAR | HPMEDGMDV | WGQGTTVTVSS |
| | 59 | | Germline | | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | -GIAAAG-YYYGMDV | WGKGTTVTVSSA |
| Sc 161 | 18 | VH5-51 | D6-13 | JH6C | EVQLVQSGAEVKKPGESLKISCKGS | GYSFTSYWIG | WVRQMPGKGLEWMG | IIYPGDSDTRYSPSFQG | QVTISADKSISTAYLQWSSLKASDTAMYYCAR | HGIAAAGFYYYYMDV | WGQGTTVTVSSA |

TABLE 9

| Light chain analysis | | | | | | | | | | |
|---|---|---|---|---|---|---|---|---|---|---|
| Chain Name | SEQ ID NO: | V Kappa | J | FR1 | CDR1 | FR2 | CDR2 | FR3 | CDR3 | J |
| | 60 | Germline | | DIVMTQTPLSLSVTPGQPASISC | KSSQSLLHSDGKTYLY | WYLQKPGQPPQLLIY | EVSNRFS | GVPDRFSGSGSGTDFTLKISRVEAEDVGVYYC | MQSIQLPWT | FGQGTKVEIK |
| Sc 254 | 28 | A2 | JK1 | DIVMTQTPLSLSVTPGQPASIFC | KSSQSLLNSDGKTYLC | WYLQKPGQPPQLLIY | EVSNRFS | GVPDRFSGSGSGTDFTLKISRVEAEDVGVYYC | MQGIQLPWAF | FGQGTKVEIK |
| | 61 | Germline | | EIVLIQSPGILSLSPGERATLSC | RASQSVSSSYLA | WYQQKPGQAPRLLIY | GASSRAT | GIPDRFSGSGSGTDFTLTISRLEPEDFAVYYC | QQYGSSPWT | FGQGTKVEIK |
| sc 188 | 24 | A27 | JK1 | EIVLTQSPGTLSLSPGERATLSC | RAGQTISSRYLA | WYQQKPGQAPRPLIY | GASSRAT | GIPDRFSGSGSGTDFTLTISRLEPEDFAVYYC | QQYGSSPRT | FGQGTKVEIK |

TABLE 9 -continued

Light chain analysis

| Chain Name | SEQ ID NO: | V Kappa | J | FR1 | CDR1 | FR2 | CDR2 | FR3 | CDR3 | J |
|---|---|---|---|---|---|---|---|---|---|---|
| sc 374 | 48 | A27 | JK1 | EIVLTQSPGTLS LSPGERATLSC | RASQSVSS SYLA | WYQQKPGQ APRLLIY | GASS RAT | DIPDRFSGSGSGTDFT LTISRLEPEDFAVYYC | QQYGSS PWT | FGQGTK VEIK |
| | 62 | Germline | | EIVLTQSPGILS LSPGERATLSC | RASQSVSS SYLA | WYQQKPGQ APRLLIY | GASS RAT | GIPDRFSGSGSGTDFT LTISRLEPEDFAVYYC | QQYGSS PYT | FGQGTK LEIK |
| Sc 49 | 4 | A27 | JK2 | EIVLTQSPGTLS LSPGERATLSC | RASQSVSS SYLA | WYQQKPGQ APRLLIY | GASS RAT | GIPDRFSGSGSGTDFT LTISRLEPEDFAVYYC | QQYGSS PCS | FGQGTK LEIK |
| | 63 | Germline | | EIVLTQSPGILS LSPGERATLSC | RASQSVSS SYLA | WYQQKPGQ APRLLIY | GASS RAT | GIPDRFSGSGSGTDFT LTISRLEPEDFAVYYC | QQYGSS PET | FGPGTK VDIKR |
| Sc 161 | 20 | A27 | JK3 | EIVLTQSPGTLS LSPGERASLSC | RASQNVNR NYLV | WYQQKPGQ APRLLIY | GTSN RAT | GIPDRFSGSGSGTDFT LTISRLEPEDFAVYYC | QQCGSL PFT | FGPGTK VDIKR |
| | 64 | Germline | | QSVLTQPPSVSA APGQKVTISC | SGSSSNIG NNYVS | WYQQLPGT APKLLIY | DNNK RPS | GIPDRFSGSKSGTSAT LGITGLQTGDEADYYC | GTWDSS LSA-YV | FGTGTK VTV |
| sc 133 | 16 | V1-19 | JL1 | QSVLTQPPSVSA APGQKVTISC | SGSSSNIG NNYVS | WYQQLPGT APKLLIY | DNNK RPS | GIPDRFSGSKSGTSAT LGITGLQTGDEADYYC | GTWNSS LSAGYV | FGTGTK VTV |
| | 65 | Germline | | QSVLTQPPSVSA APGQKVTISC | SGSSSNIG NNYVS | WYQQLPGT APKLLIY | DNNK RPS | GIPDRFSGSKSGTSAT LGITGLQTGDEADYYC | GTWDSS LSAVV | FGGGTK LTVL |
| sc 320 | 44 | V1-19 | JL2 | QSVLTQPPSMSA APGQKVTISC | SGSSSNIG NNYVS | WYQQLPGT APKLLIY | DNNK RPS | GIPDRFSGSKSGTSAT LGITGLQTGDEADYYC | GTWDSS LSAGV | FGGGTK LTVL |
| | 66 | Germline | | SYELTQPPSVSV SPGQTARITC | SGDALPKK YAY | WYQQKSGQ APVLVIY | EDSK RPS | GIPERFSGSSSGTMAT LTISGAQVEDEADYYC | YSTDSS GNHVV | FGGGTK LTVL |
| sc 277 | 36 | V2-7 | JL2 | SYELTQPPSVSV SPGQTARITC | SGDALPKK YAF | WYQQKSGQ APVLVIY | DDNK RPS | GIPERFSGSSSGTMAT LTISGAQVEDEADYYC | YSTDSS GRP | FGGGTK LTVL |
| sc 97 | 12 | V2-7 | JL2 | SYELTQPPSVSV SPGQTARITC | SGDALPKK YAY | WYQQKSGQ APVLVIY | EDIK RPS | GIPERFSGSSSGTMAT LTISGAQVEDEADYYC | YSTDSS GNEWVF | FGGGTK LTVL |
| | 67 | Germline | | SYELTQPPSVSV SPGQTARITC | SGDALPKK YAY | WYQQKSGQ APVLVIY | EDSK RPS | GIPERFSGSSSGTMAT LTISGAQVEDEADYYC | YSTDSS GNHVV | FGGGTK LTVL |
| sc 58 | 8 | V2-7 | JL3 | SYELTQPPSVSV SPGQTARITC | SGDALPKK YAY | WYQQKSGQ APVLVIY | DDSK RPS | GIPERFSGSSSGTMAT LTISGAQVEDEADYYC | YSTDSS GRIP | FGGGTK LTVL |
| | 68 | Germline | | SSELTQDPAVSV ALGQTVRITC | QGDSLRSY YAS | WYQQKPGQ APVLVIY | GKNN RPS | GIPDRFSGSSSGNTAS LTITGAQAEDEADYYC | NSRDSS GNHVV | FGGGTK LTVL |
| sc 298 | 40 | V2-13 | JL2 | SSELTQDPVVSV ALGQTVRITC | QGDSLRSY YLS | WYQQKPGQ APVLVIY | GKNN RPS | GIPDRFSGSNSGNTAS LTITGAQAEDEADYYC | NSRDSS GNHL | FGGGTK LTVL |
| | 69 | Germline | | SYELTQPSSVSV SPGQTARITC | SGDVLAKK YAR | WFQQKPGQ APVLVIY | KDSE RPS | GIPERFSGSSSGTTVT LTISGAQVEDEADYYC | YSAADN NVV | FGGGTK LTVL |
| sc 264 | 32 | V2-19 | JL2 | SYELTQPSSVSV SPGQTARITC | SGDVLAKK SAR | WFHQKPGQ APVLVIY | KDSE RPS | GIPERFSGSSSGTTVT LTISGAQVEDEAAYYC | YSAADN NLV | FGGGTK LTVL |

TABLE 10

Exemplary Mutations of sc 133 Heavy Chain (SEQ ID NO: 14) to Germline (SEQ ID NO: 49) at the indicated Residue Number

| 54 | 57 | 70 | 76 |
|---|---|---|---|
| N | G | M | T |
| N | G | L | I |
| N | G | L | T |
| N | D | M | I |
| N | D | L | I |
| N | D | M | T |
| N | D | L | T |
| K | G | M | I |
| K | G | M | T |

TABLE 10-continued

Exemplary Mutations of sc 133 Heavy Chain (SEQ ID NO: 14) to Germline (SEQ ID NO: 49) at the indicated Residue Number

| 54 | 57 | 70 | 76 |
|---|---|---|---|
| K | G | L | I |
| K | G | L | T |
| K | D | M | I |
| K | D | L | I |
| K | D | M | T |

TABLE 11

Exemplary Mutations of sc 188 Light Chain (SEQ ID NO: 24) to Germline (SEQ ID NO: 61) at the indicated Residue Number

| 26 | 28 | 29 | 32 | 47 |
|---|---|---|---|---|
| G | S | V | S | L |
| G | S | V | S | P |
| G | S | V | R | P |
| G | S | V | R | L |
| G | S | V | R | L |
| G | S | V | S | P |
| G | S | I | R | P |
| G | S | I | R | L |
| G | T | V | R | L |
| G | T | V | S | P |
| G | T | V | S | L |
| G | T | I | R | P |
| G | T | I | R | L |
| G | T | I | S | L |
| S | S | V | S | P |
| S | S | V | R | P |
| S | S | V | R | L |
| S | S | V | R | L |
| S | S | V | S | P |
| S | S | I | R | P |
| S | S | I | R | L |
| S | T | V | R | L |
| S | T | V | S | P |
| S | T | V | S | L |
| S | T | I | R | P |
| S | T | I | R | L |
| S | T | I | S | L |

TABLE 12

Exemplary Mutations of sc 188 Heavy Chain (SEQ ID NO: 22) to Germline (SEQ ID NO: 56) at the indicated Residue Number

| 33 | 37 | 45 | 60 | 78 | 83 | 85 |
|---|---|---|---|---|---|---|
| G | S | K | Y | N | K | S |
| G | S | K | Y | N | K | T |
| G | S | K | Y | N | N | S |
| G | S | K | Y | N | N | T |
| G | S | K | Y | K | N | S |
| G | S | K | Y | K | N | T |
| G | S | K | Y | K | K | S |
| G | S | K | Y | K | K | T |
| G | S | K | S | N | K | S |
| G | S | K | S | N | K | T |
| G | S | K | S | N | N | S |
| G | S | K | S | N | N | T |
| G | S | K | S | K | N | S |
| G | S | K | S | K | N | T |
| G | S | K | S | K | K | S |
| G | S | K | S | K | K | T |
| G | S | N | Y | N | K | S |
| G | S | N | Y | N | K | T |
| G | S | N | Y | N | N | S |
| G | S | N | Y | N | N | T |
| G | S | N | Y | K | N | S |
| G | S | N | Y | K | N | T |
| G | S | N | Y | K | K | S |
| G | S | N | Y | K | K | T |
| G | S | N | S | N | K | S |
| G | S | N | S | N | K | T |
| G | S | N | S | N | N | S |
| G | S | N | S | N | N | T |
| G | S | N | S | K | N | S |
| G | S | N | S | K | N | T |
| G | S | N | S | K | K | S |
| G | S | N | S | K | K | T |
| V | S | K | Y | N | K | S |
| V | S | K | Y | N | K | T |
| V | S | K | Y | N | N | S |
| V | S | K | Y | N | N | T |
| V | S | K | Y | K | N | S |

TABLE 12-continued

Exemplary Mutations of sc 188 Heavy Chain (SEQ ID NO: 22) to Germline (SEQ ID NO: 56) at the indicated Residue Number

| 33 | 37 | 45 | 60 | 78 | 83 | 85 |
|---|---|---|---|---|---|---|
| V | S | K | Y | K | N | T |
| V | S | K | Y | K | K | S |
| V | S | K | Y | K | K | T |
| V | S | K | S | N | K | S |
| V | S | K | S | N | K | T |
| V | S | K | S | N | N | S |
| V | S | K | S | N | N | T |
| V | S | K | S | K | N | S |
| V | S | K | S | K | N | T |
| V | S | K | S | K | K | S |
| V | S | K | S | K | K | T |
| V | S | N | Y | N | K | S |
| V | S | N | Y | N | K | T |
| V | S | N | Y | N | N | S |
| V | S | N | Y | N | N | T |
| V | S | N | Y | K | N | S |
| V | S | N | Y | K | N | T |
| V | S | N | Y | K | K | S |
| V | S | N | Y | K | K | T |
| V | S | N | S | N | K | S |
| V | S | N | S | N | K | T |
| V | S | N | S | N | N | S |
| V | S | N | S | N | N | T |
| V | S | N | S | K | N | S |
| V | S | N | S | K | N | T |
| V | S | N | S | K | K | S |
| V | S | N | S | K | K | T |
| G | I | K | Y | N | K | S |
| G | I | K | Y | N | K | T |
| G | I | K | Y | N | N | S |
| G | I | K | Y | N | N | T |
| G | I | K | Y | K | N | S |
| G | I | K | Y | K | N | T |
| G | I | K | Y | K | K | S |
| G | I | K | Y | K | K | T |
| G | I | K | S | N | K | S |
| G | I | K | S | N | K | T |
| G | I | K | S | N | N | S |
| G | I | K | S | N | N | T |
| G | I | K | S | K | N | S |
| G | I | K | S | K | N | T |
| G | I | K | S | K | K | S |
| G | I | K | S | K | K | T |
| G | I | N | Y | N | K | S |
| G | I | N | Y | N | K | T |
| G | I | N | Y | N | N | S |
| G | I | N | Y | N | N | T |
| G | I | N | Y | K | N | S |
| G | I | N | Y | K | N | T |
| G | I | N | Y | K | K | S |
| G | I | N | Y | K | K | T |
| G | I | N | S | N | K | S |
| G | I | N | S | N | K | T |
| G | I | N | S | N | N | S |
| G | I | N | S | N | N | T |
| G | I | N | S | K | N | S |
| G | I | N | S | K | N | T |
| G | I | N | S | K | K | S |
| G | I | N | S | K | K | T |
| V | I | K | Y | N | K | S |
| V | I | K | Y | N | K | T |
| V | I | K | Y | N | N | S |
| V | I | K | Y | N | N | T |
| V | I | K | Y | K | N | S |
| V | I | K | Y | K | N | T |
| V | I | K | Y | K | K | S |
| V | I | K | Y | K | K | T |
| V | I | K | S | N | K | S |
| V | I | K | S | N | K | T |
| V | I | K | S | N | N | S |
| V | I | K | S | N | N | T |
| V | I | K | S | K | N | S |
| V | I | K | S | K | N | T |
| V | I | K | S | K | K | S |
| V | I | K | S | K | K | T |

TABLE 12-continued

Exemplary Mutations of sc 188 Heavy Chain (SEQ ID NO: 22) to Germline (SEQ ID NO: 56) at the indicated Residue Number

| 33 | 37 | 45 | 60 | 78 | 83 | 85 |
|---|---|---|---|---|---|---|
| V | I | N | Y | N | K | S |
| V | I | N | Y | N | K | T |
| V | I | N | Y | N | N | S |
| V | I | N | Y | N | N | T |
| V | I | N | Y | K | N | S |
| V | I | N | Y | K | N | T |
| V | I | N | Y | K | K | S |
| V | I | N | Y | K | K | T |
| V | I | N | S | N | K | S |
| V | I | N | S | N | K | T |
| V | I | N | S | N | N | S |
| V | I | N | S | N | N | T |
| V | I | N | S | K | N | S |
| V | I | N | S | K | N | T |
| V | I | N | S | K | K | S |
| V | I | N | S | K | K | T |

TABLE 13

Exemplary Mutations of sc 264 Light Chain (SEQ ID NO: 32) to Germline (SEQ ID NO: 69) at the indicated Residue Number

| 31 | 36 | 84 |
|---|---|---|
| Y | H | A |
| Y | H | D |
| Y | Q | A |
| S | H | D |
| S | Q | D |
| S | Q | A |

Example 10

Potency Determination of αVβ6 Antibodies

To discriminate antibodies based on their ability to prevent the adhesion of HT29 cells to TGFβLAP, the following adhesion assay was performed.

Nunc MaxiSorp (Nunc) plates were coated overnight with 50 μL of 10 μg/ml TGF Beta1 LAP (TGFβLAP), and pre-blocked with 3% BSA/PBS for 1 hour prior to the assay. HT29 cells grown to the optimal density were then pelleted and washed twice in HBBS (with 1% BSA and without $Mn^{2+}$), after which the cells were then resuspended in HBSS at 30,000 cell per well. The coating liquid was removed from the plates, which were then blocked with 100 μL 3% BSA at room temperature for 1 hour and thereafter washed twice with PBS.

Antibody titrations were prepared in 1:3 serial dilutions in a final volume of 30 μL and at two times the final concentration. Care was taken to ensure that the PBS concentration in the control wells matched the PBS concentration in the most dilute antibody well. 30 μL of cells were added to each well, and the cells were incubated in the presence of the antibodies at 4° C. for 40 minutes in a V-bottom plate. The cell-antibody mixtures were transferred to the coated plate and the plate was incubated at 37° C. for 40 minutes. The cells on the coated plates were then washed four times in warm HBSS, and the cells were thereafter frozen at −80° C. for 15 minutes. The cells were allowed to thaw at room temperature, and then 100 μL of CyQuant dye/lysis buffer (Molecular Probes) was added to each well according to the manufacturer's instructions. Fluorescence was read at an excitation wavelength of 485 nm and an emission wavelength of 530 nm. An estimated $IC_{50}$ value for each mAb was calculated based on the maximal and minimal amount of cell adhesion possible in the assay, as determined by positive and negative control wells. The results for twelve antibodies are summarized in Table 14.

TABLE 14

Adhesion Assay Results (Estimated $IC_{50}$ Values)

| | n = 1 (ng/mL) | n = 2(ng/mL) | n = 3 (ng/mL) |
|---|---|---|---|
| sc 049 | >5000 | >5000 | >5000 |
| sc 058 | 4065 | 2028 | 3259 |
| sc 097 | 1006 | 281 | 536 |
| sc 133 | 25 | 16 | 30 |
| sc 161 | 2408 | 137 | ND |
| sc 188 | 41 | 26 | ND |
| sc 254 | 63 | 37 | 37 |
| sc 264 | 26 | 14 | 18 |
| sc 277 | 1455 | 540 | 720 |
| sc 298 | 29 | 25 | 33 |
| sc 320 | 648 | 381 | 415 |
| sc 374 | 277 | 300 | 549 |
| Positive Control 2077Z | 226 | 185 | 286 |

Example 11

Competition Assay

To establish that the antibodies were specifically capable of blocking αVβ6 integrin binding to soluble TGFβLAP, a competition assay was run with the purified antibodies to measure their ability to bind to αVβ6 and block its binding to a GST-LAP peptide.

Medium binding 96-well plates (Costar, catalog #3368) were coated with 50 μL/well of 10 μg/ml GST-LAP in PBS and 0.05% sodium azide, and incubated overnight at 4° C. The plates were then washed three times using 300 μL/well of assay diluent (1% milk in TBS (50 mM Tris, 50 mM NaCl, 1 mM $MgCl_2$ and 1 mM $CaCl_2$, pH 6.9), after which the plates were blocked using 300 μL/well 5% milk in TBS and incubated for 30 minutes at room temperature. The mAbs (in 1:3 serial dilutions ranging from 10 μg/ml to 0.01 μg/ml) were incubated overnight with αVβ6 (250 ng/ml in assay diluent containing 0.05% sodium azide). The following day, 50 μL/well of the pre-incubated primary antibody was transferred to the GST-LAP peptide-coated plate and incubated for one hour at room temperature. The wells were then washed three times using 300 μL/well of assay diluent. Then, to detect the amount of αVβ6 bound to the plates, mAb 2075 (Chemicon) was added at a concentration of 1 μg/ml in assay diluent (50 μL/well) and incubated for one hour at room temperature. The wells were then washed three times using 300 μL/well of assay diluent, and incubated with goat anti-mouse IgG Fc-peroxidase at 400 ng/ml in assay diluent (50 μL/well) for one hour at room temperature. The wells were then washed three times using 300 μL/well of assay diluent, and developed using 1-step TMB (Neogen) at a total volume of 50 μL/well. After 15 minutes, the developing reaction was quenched with 50 μL/well of 1N Hydrochloric acid. The plates were read at 450 nm, and the results for five of the antibodies are summarized in FIG. 1, which shows that the antibodies were able to inhibit αVβ6 binding to GST-LAP.

Example 12

Cross-Reactivity to αvβ3 or αVβ5 Integrins

To establish that the antibodies were functional only against αVβ6 integrin and not αVβ3 or αVβ5 integrins, the following assay was performed to test the ability of the antibodies to inhibit the adhesion of A375M cells to an osteopontin peptide.

Assay plates were coated with osteopontin peptide. Two fragments of osteopontin were used: OPN 17-168 and OPN 17-314. Assay plates were pre-blocked with 3% BSA/PBS for one hour prior to the assay. The A375M cells were removed from a culture flask, pelleted and washed twice with HBSS containing 1% BSA and 1 mM $Ca^{2+}$ and 1 mM $Mg^{2+}$. The cells were then resuspended in HBSS at a concentration of 30,000 cells per well. The coating liquid containing the osteopontin fragments was removed, and the plates were blocked with 100 μL of 3% BSA for one hour at room temperature. The coated plates were washed twice with HBSS containing 1% BSA. Antibody titrations were prepared in 1:4 serial dilutions in a final volume of 30 μL and at twice the final concentration. The resuspended cells were added to the wells containing the titrated antibody in a V-bottom plate, and the cells and antibodies were co-incubated at 4° C. for 40 minutes. The cell-antibody mixture was then transferred to the coated plate, which was thereafter incubated at 37° C. for 40 minutes. The cells on the coated plates were next washed four times in warm HBSS, and the cells in the plates were then frozen at −80° C. for 15 minutes. The cells were allowed to thaw at room temperature, and then 100 μL of CyQuant dye/lysis buffer (Molecular Probes) was added to each well according to the manufacturer's instructions. Fluorescence was read at an excitation wavelength of 485 nm and an emission wavelength of 530 nm.

The results for five of the antibodies are summarized in Table 15. A commercially available αV integrin specific antibody was used as a positive control in this assay and exhibited about 90% inhibition of adhesion. A commercially available αVβ6 antibody served as a negative control in this assay for adhesion to αVβ3 or αVβ5 integrins. All antibodies were tested at a concentration of 5 μg/ml and none of the test antibodies could block adhesion to αVβ3 or αVβ5 integrins.

TABLE 15

Cross-Reactivity to αVβ3 or αVβ5 Integrins

| Antibody ID | Percent Inhibition |
|---|---|
| sc 133 | 3 |
| sc 188 | −2 |
| sc 254 | −5 |
| sc 264 | 3 |
| sc 298 | 9 |
| αV Control | 89 |
| αVβ6 Control | 11 |
| Human IgG Control | 3 |
| Mouse IgG Control | 5 |

Example 13

Cross-Reactivity to α4β1 Integrin

To establish that the antibodies were functional only against the αVβ6 integrin and not the α4β1 integrin, an assay was performed to test the ability of the antibodies to inhibit the adhesion of J6.77 cells to the CS-1 peptide of fibronectin. The assay was performed as described in Example 12 above, with the exception that J6.77 cells were used for binding and the CS-1 peptide of fibronectin was used to coat the assay plates.

The results for 11 of the antibodies are summarized in Table 16. A commercially available β1 integrin specific antibody was used as a positive control in this assay and exhibited 97% inhibition of adhesion. A commercially available αVβ6 specific antibody served as a negative control in this assay for adhesion to α4β1. All antibodies were used at 5 μg/ml and none of the test antibodies could block adhesion to α4β1.

TABLE 16

Cross-Reactivity to α4β1 Integrin

| Antibody at 5 ug/ml | Percent Inhibition |
|---|---|
| sc 58 | −14 |
| sc 97 | −7 |
| sc 133 | −15 |
| sc 161 | 12 |
| sc 188 | −10 |
| sc 254 | 0 |
| sc 264 | −8 |
| sc 277 | −17 |
| sc 298 | −7 |
| sc 320 | −8 |
| sc 374 | −8 |
| Human IgG1 | −6 |
| Human IgG2 | −9 |
| Anti-beta1 integrin antibody | 97 |
| Anti-αVβ6 integrin antibody | −15 |
| No CS-1 or antibody on plates | 12 |
| CS-1 fragment coated plates without antibody | 10 |

Example 14

Cross-Reactivity to α5β1 Integrin

To establish that the antibodies were functional only against the αVβ6 integrin and not the α5β1 integrin, an adhesion assay was performed to test the ability of the antibodies to inhibit the adhesion of K562 cells to fibronectin.

Assay plates were coated with the FN9-10 peptide of fibronectin at a concentration of 12.5.1 g/mL. Assay plates were pre-blocked with 3% BSA/PBS for one hour prior to the assay. The K562 cells were removed from a culture flask, pelleted and washed twice with HBSS containing 1% BSA and 1 mM $Mn^{2+}$. The cells were then resuspended in HBSS at a concentration of 30,000 cells per well. The coating liquid containing the osteopontin fragments was removed, and the plates were blocked with 100 μL of 3% BSA for one hour at room temperature. The coated plates were washed twice with HBSS containing 1% BSA. Antibody titrations were prepared in 1:4 serial dilutions in a final volume of 30 μL and at twice the final concentration. The resuspended cells were added to the wells containing the titrated antibody in a V-bottom plate, and the cells and antibodies were co-incubated at 4° C. for 60 minutes. The cell-antibody mixture was then transferred to the coated plate, which was thereafter incubated at 37° C. for 40 minutes. The cells on the coated plates were next washed four times in warm HBSS, and the cells in the plates were then frozen at −80° C. for 15 minutes. The cells were allowed to thaw at room temperature, and then 100 μL of CyQuant dye/lysis buffer (Molecular Probes) was added to each well according to the manufacturer's instructions. Fluorescence was read at an excitation wavelength of 485 nm and an emission wavelength of 530 nm.

The results for five of the antibodies are summarized in Table 17. Test antibodies were compared to a commercially available α5β1 antibody as a positive control and an αVβ6 specific antibody as a negative control. None of the test antibodies were able to block adhesion in the assay at the 5 μg/ml concentration used in this assay.

TABLE 17

Cross-Reactivity to α5β1 Integrin

| Antibody ID | Percent Inhibition |
|---|---|
| sc 133 | −12 |
| sc 188 | 5 |
| sc 254 | −9 |
| sc 264 | −4 |
| sc 298 | 2 |
| αVβ6 Control | 7 |
| α5β1 Control | 78 |
| Human IgG Control | 11 |

Example 15

Cross-Reactivity to Murine and Cynomolgus αVβ6 Integrin

In order to determine whether the antibodies exhibited cross-reactivity to mouse αVβ6 or Cynomolgus αVβ6, the following assay was performed.

Cross-reactivity of the mAbs to macaque and mouse αVβ6 was tested on the purified mAbs using FACS analysis on HEK-293 cells transiently transfected with cynomolgus or mouse αV, β6, or αVβ6. Approximately 48 hours after transfection, the cells were collected and resuspended in FACS buffer to reach a final concentration of approximately 50,000 cells in 100 μL.

Approximately 100,000 cells total, were used in each reaction as follows. 200 μL of 293 cells were dispensed into a V-bottom plate. The cells in the plate were pelleted at 1500 rpm for 3 minutes, and then resuspended in 100 μL FACS buffer. The pelleting step was repeated, and the FACS buffer supernatant was removed. The purified mAbs, or control primary antibodies were added in a volume of 50 μL and the cells were resuspended. Primary antibody controls were murine αVβ6 (Cat#MAB2077z, Chemicon) and anti-αV and anti-β6 recombinants. The plate was incubated on ice for 45 minutes, after which 100 μL FACS buffer was added to dilute the primary antibody. The cells were then pelleted by centrifuging at 1500 rpm for 3 minutes, and the pellet was resuspended in 100 μL FACS buffer. The pelleting step was repeated, and the FACS buffer supernatant was removed. Cells were then resuspended in the appropriate secondary antibody (5 μg/ml) with 7AAD dye (10 μg/ml), and stained on ice for 7 minutes. Then 150 μL of FACS buffer was added and the cells were pelleted at 1500 rpm for 3 minutes, after which the cells were washed in 100 μL FACS buffer, pelleted, and then resuspended in 250 μL buffer and added to FACS tubes. Samples were analyzed on a high throughput FACS machine and analyzed using Cell Quest Pro software.

The results are summarized in Table 18, and demonstrate that mAb sc 133 and mAb sc 188 were clearly cross-reactive with mouse and Cynomolgus αVβ6 and β6. mAb sc 254 appeared to cross-react with β6, αV, and αVβ6. mAbs sc 264 and 298 had high levels of binding to parental cells making species cross-reactivity difficult to discern.

TABLE 18

Cross-Reactivity with Mouse and Cynomolgus αVβ6

| Antibodies | Parental | Mouse alphaV | Mouse beta6 | Mouse alphaVbeta6 | Cynomolgus alphaV | Cynomolgus beta6 | Cynomolgus alphaVbeta6 |
|---|---|---|---|---|---|---|---|
| Cells alone | 0 | 0 | 0 | 0 | 1 | 0 | 0 |
| Gt anti Mouse | 0 | 0 | 0 | 0 | 0 | 0 | 0 |
| anti alphaVbeta6 | 0 | 1 | 11 | 45 | 0 | 5 | 20 |
| anti alphaV | 68 | 68 | 63 | 59 | 68 | 69 | 67 |
| anti beta6 | 0 | 0 | 0 | 0 | 0 | 0 | 0 |
| Gt anti Human | 0 | 0 | 0 | 0 | 0 | 0 | 0 |
| Human IgG1 | 0 | 1 | 0 | 1 | 1 | 1 | 0 |
| sc.133 | 2 | 4 | 19 | 49 | 5 | 10 | 28 |
| sc.188 | 1 | 3 | 29 | 51 | 2 | 17 | 27 |
| sc.254 | 8 | 13 | 21 | 50 | 16 | 19 | 26 |
| sc.264 | 74 | 71 | 68 | 63 | 70 | 75 | 54 |
| sc.298 | 49 | 45 | 52 | 53 | 48 | 52 | 38 |

Data represent percent of cells shifted

Example 16

Internalization Assay

The internalization of the antibodies was tested using a K562 cell line that stably expressed human αVβ6. Internalization of the purified antibodies was compared to a commercially available αVβ6 antibody that was not internalized in this assay.

The results are summarized in Table 19.

TABLE 19

| Summary of the Internalization Assay | | |
|---|---|---|
| Antibody | Concentration (ug/mL) | Percent Internalization |
| sc133 | 10 | 28% |
| sc133 | 1 | 30% |
| sc 188 | 10 | 38% |
| sc 188 | 1 | 34% |
| sc 254 | 10 | 49% |
| sc 254 | 1 | 39% |
| sc 264 | 10 | 76% |
| sc 264 | 1 | 77% |
| sc 298 | 10 | 28% |
| sc 298 | 1 | 26% |

Example 17

High Resolution Biacore Analysis

High resolution Biacore analysis using a soluble αVβ6 protein to bind antibodies immobilized on CM5 chips was performed for 5 of the αVβ6 antibodies to estimate their affinity for soluble antigen.

The Biacore analysis was performed as follows. A high-density goat α human IgG antibody surface over two CM5 Biacore chips was prepared using routine amine coupling. Each mAb was diluted in degassed HBS-P running buffer containing 100 μg/ml BSA, 1 mM $MgCl_2$, and 1 mM $CaCl_2$ to a concentration of approximately 1 μg/mL. More precisely, mAb sc 133 was diluted to 0.98 μg/mL, mAb sc 188 was diluted to 0.96 g/mL, mAb sc 264 was diluted to 0.94 μg/mL, mAb sc 254.2 was diluted to 0.87 μg/mL, and mAb sc 298 was diluted to 1.6 μg/mL. Then, a capture level protocol was developed for each mAb by capturing each mAb over a separate flow cell at a 10 μL/min flow rate at the concentrations listed above. mAbs sc 133, sc 298, and sc 254.2 were captured for 30 seconds while mAbs sc 188 and sc 264 were captured for 1 minute. A 4-minute wash step at 50 μL/min followed to stabilize the mAb baseline.

Soluble αVβ6 was injected for 4 minutes at a concentration range of 116-3.6 nM for mAbs sc 133, sc 188, sc 264, and sc 298, and 233-3.6 nM for mAb sc 254.2, with a 2× serial dilution for each concentration range. A 10-minute dissociation followed each antigen injection. The antigen samples were prepared in the HBS-P running described above. All samples were randomly injected in triplicate with several mAb capture/buffer inject cycles interspersed for double referencing. The high-density goat α mouse antibody surfaces were regenerated with one 18-second pulse of 146 mM phosphoric acid (pH 1.5) after each cycle at a flow rate of 100 μL/min. A flow rate of 50 μL/min was used for all antigen injection cycles.

The data were then fit to a 1:1 interaction model with the inclusion of a term for mass transport using CLAMP. The resulting binding constants are listed in Table 20. The mAbs are listed from highest to lowest affinity.

TABLE 20

| Affinity Determination Results for Cloned and Purified mAbs Derived from High Resolution Biacore ™. | | | | |
|---|---|---|---|---|
| Antibody | $R_{max}$ | $k_a$ ($M^{-1}s^{-1}$) | $k_d$ ($s^{-1}$) | $K_D$ (nM) |
| sc 264 | 96 | $5.85 \times 10^4$ | $3.63 \times 10^{-4}$ | 6.2 |
| sc 298 | 77 | $5.65 \times 10^4$ | $1.18 \times 10^{-3}$ | 21.0 |
| sc 188 | 76 | $4.52 \times 10^4$ | $9.56 \times 10^{-4}$ | 21.2 |
| sc 133 | 96 | $5.73 \times 10^4$ | $1.89 \times 10^{-3}$ | 33.0 |
| sc 254.2 | 53, 45 | $5.73 \times 10^4$ | $5.64 \times 10^{-4}$ | 34.9 |

Example 18

Binding Affinity Analysis Using FACS

As an alternative to Biacore, FACS analysis was also used to estimate the binding affinity of one of the antibodies to K562 cells that stably express the human αVβ6 antigen. The amount of antigen was titrated to generate a binding curve and estimate the binding affinity to the antigen.

K562 cells expressing αVβ6 were resuspended in filtered HBS buffer containing 1 mM of $MgCl_2$ and 1 mM of $CaCl_2$ at a concentration of approximately 6 million cells/mL. The cells were kept on ice. Purified mAb sc 188 was serially diluted by a factor of 1:2 in HBS across 11 wells in a 96-well plate. The $12^{th}$ well in each row contained buffer only. Titrations were done in triplicate. Additional HBS and cells were added to each well so that the final volume was 300 μL/well and each well contained approximately 120,000 cells. The final molecular concentration range for mAb sc 188 was 4.9-0.019 nM. The plates were placed into a plate shaker for 5 hours at 4° C., after which the plates were spun and washed three times with HBS, following which, 200 μL of 131 nM Cy5 goat α-human polyclonal antibody (Jackson Laboratories, #109-175-008) were added to each well. The plates were then shaken for 40 minutes at 4° C., and thereafter were spun and washed once again three times with HBS. The Geometric Mean Fluorescence (GMF) of 20,000 "events" for each mAb concentration was recorded using a FACSCalibur instrument, and the corresponding triplicate titration points were averaged to give one GMF point for each mAb concentration. A plot of the averaged GMF as a function of molecular mAb concentration with Scientist software was fit nonlinearly using the equation:

$$F = P'\frac{(K_D + L_T + n\cdot M) - \sqrt{(K_D + L_T + n\cdot M)^2 - 4n\cdot M\cdot L_T}}{2} + B$$

In the above equation, F=geometric mean fluorescence, $L_T$=total molecular mAb concentration, P'=proportionality constant that relates arbitrary fluorescence units to bound mAb, M=cellular concentration in molarity, n=number of receptors per cell, B=background signal, and $K_D$=equilibrium dissociation constant. For mAb sc 188 an estimate for $K_D$ is obtained as P', n, B, and $K_D$ are allowed to float freely in the nonlinear analysis.

Figure 2A:
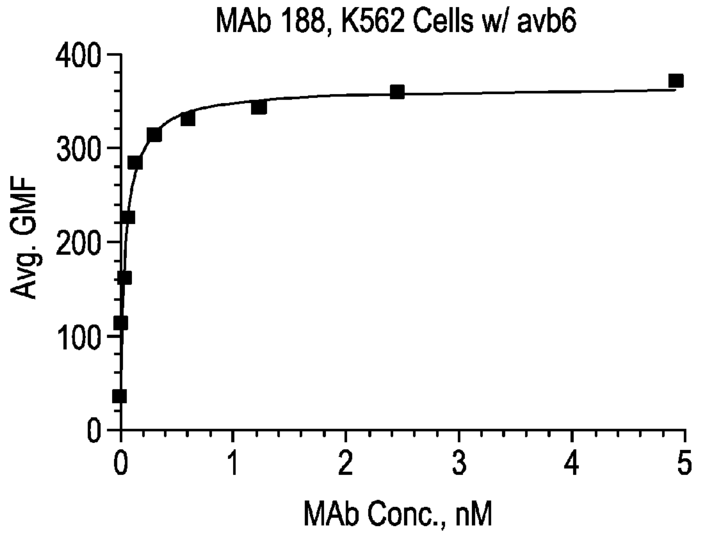
FIGS. 2A and 2B are line graphs showing a plot of the averaged Geometric Mean Fluorescence (GMF) as a function of molecular mAb concentration, which was used to estimate the binding affinity of one of the antibodies to K562 cells that stably express the human αVβ6 antigen. Shown in FIG. 2A is affinity data for mAb 188.
Figure 2B:
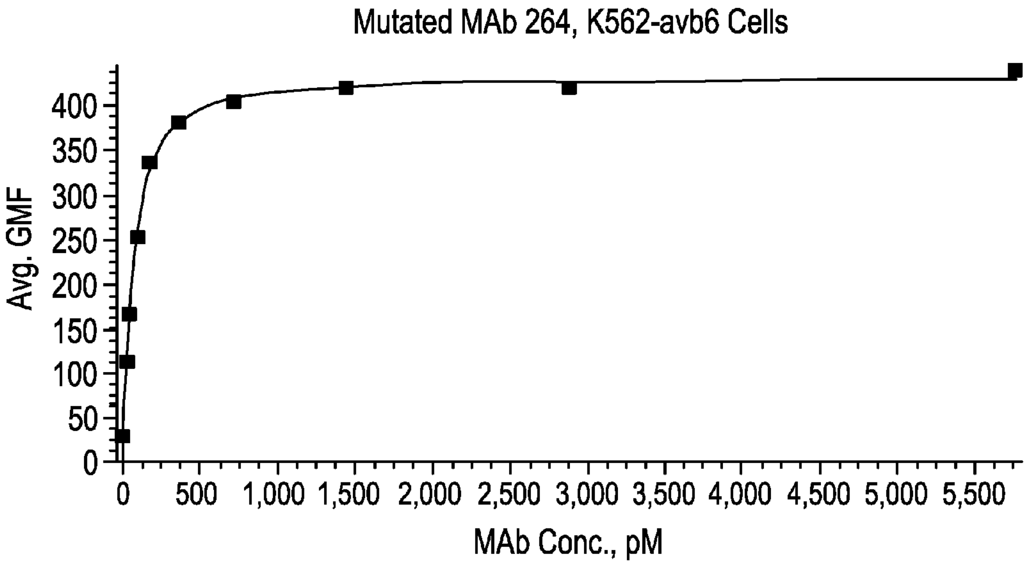
Figure 3A:
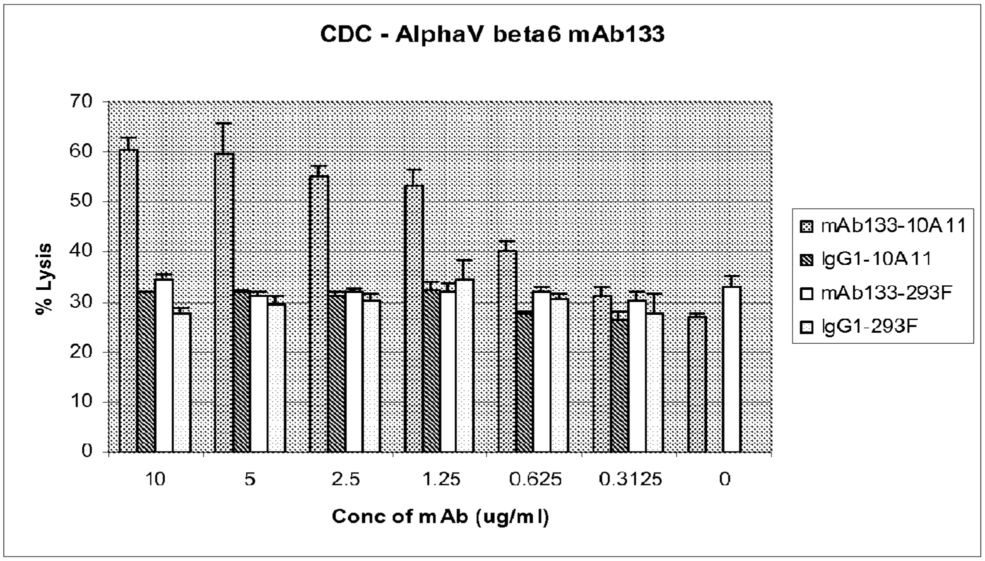
FIGS. 3A-3E are bar graphs showing the ability of the purified monoclonal antibodies to mediate complement-dependent cytotoxicity in 293 cells stably expressing αVβ6 integrin.
Figure 3B:
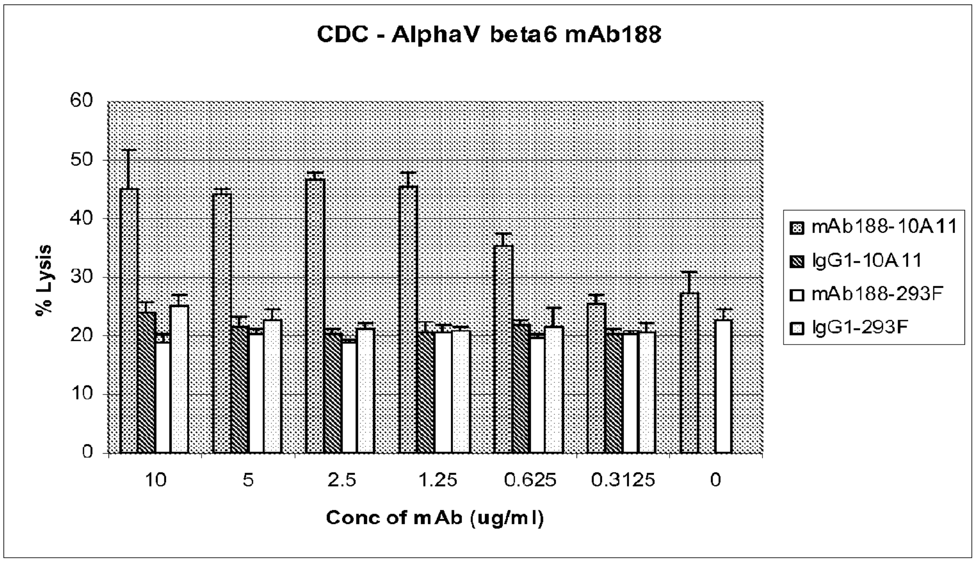
Figure 3C:
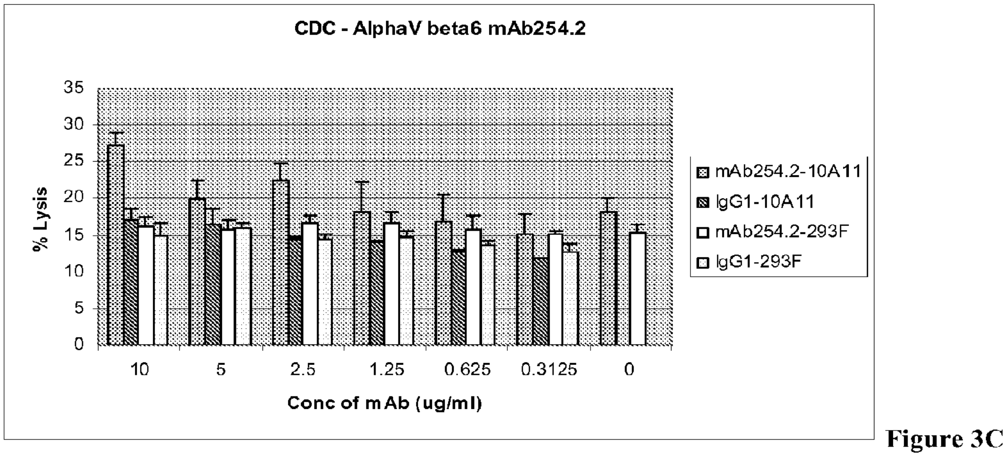
Figure 3D:
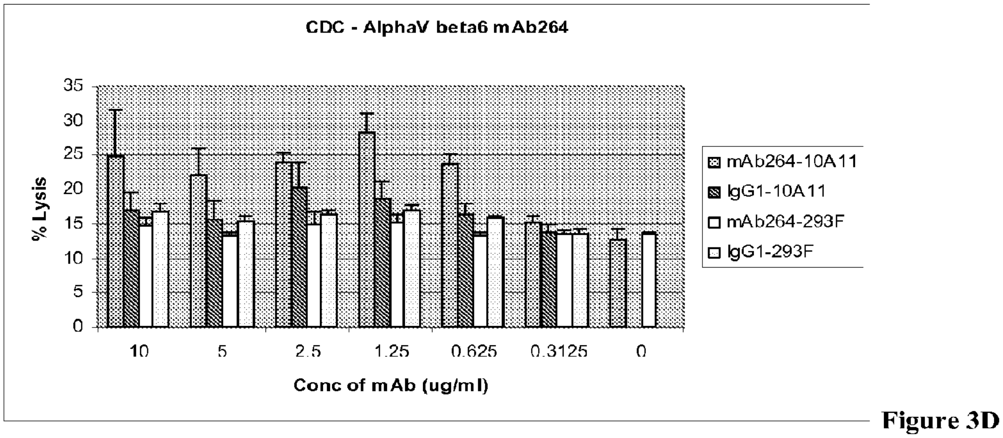
Figure 3E:
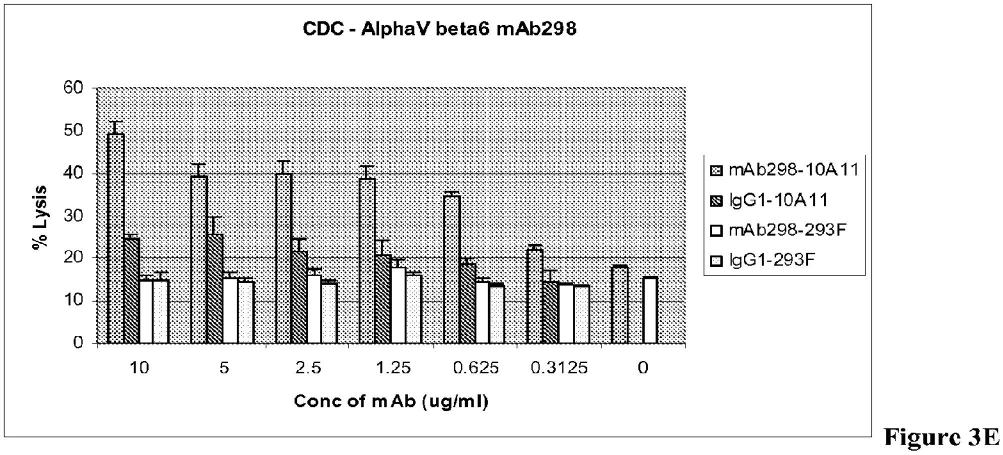

The resulting plot with its nonlinear fits (red line) is shown in FIG. 2. Table 21 lists the resulting $K_D$ for mAb sc 188 along with the 95% confidence interval of the fit. These results for mAb sc 188 indicate binding to one type of receptor.

Binding affinity for sc 188 as determined by FACS was significantly tighter than as determined by Biacore (Example 17). There are at least 2 possible explanations for the difference in $K_D$ values for sc 188. The first reason is that the two assays used different forms of the antigen for the measurement—Biacore used soluble antigen and the FACs analysis used a cell-bound form of the antigen. The second reason is that the antibodies that were tested were raised against the cell-bound form of the antigen and may not bind with as high an affinity to the soluble antigen as they do to the cell-bound antigen.

TABLE 21

Binding Affinity Analysis Using FACS

| Antibody | $K_D$ (pM) | 95% CI (pM) |
|---|---|---|
| sc 188 | 51.9 | ±22.7 |

Example 19

CDC Assay

The purified antibodies described in the examples above are of the IgG1 isotype and can have effector function. In order to determine the ability of these antibodies to mediate complement-dependent cytotoxicity (CDC), the following assay was performed using 293 cells stably expressing αVβ6 (293-10A11) and parental 293 cells (293F).

For calcein staining of cells, aliquots of approximately 25×10e6 each of HT29, 293-10A11, and 293F cells were individually resuspended in 3 ml serum-free RPMI media. 45 μL of 1 mM calcein was then added to each 3 ml sample of cells, and the samples were incubated at 37° C. for 45 minutes. The cells were centrifuged at 1200×RPM for 3 minutes, the supernatant was discarded and the cells were resuspended in each respective cell line's culture media. The centrifugation step was repeated and the cells were resuspended to give a final concentration of about 100,000 cells in 50 μL media.

Serial 1:2 dilutions of each antibody were prepared in a v-bottom 96-well plate, with concentrations ranging from 20 μg/ml to 0.625 μg/ml in a volume of 50 μL. Then, 100,000 of the cells prepared as described above were added in a volume of 50 μL to the antibody-containing plates, and the resulting mixture was incubated on ice for two hours. Following the incubation, the cells were pelleted, and the supernatant was discarded. The cells were resuspended in 100 μL of their respective media containing 10% human sera (ABI donor #27), and incubated at 37° C. for 30 minutes. The cells were then centrifuged, and 80 μL of the supernatant was transferred to a FMAT plate. The plate was read on a Tecan reader using an excitation wavelength of 485 nm and an emission wavelength of 530 nm.

The results are summarized in FIGS. 3A-3E, and demonstrate that each purified antibody tested is capable of mediating CDC in 293 cells stably expressing αVβ6 integrin.

Example 20

Site-Directed Mutagenesis

One of the antibodies (sc 264) prepared from the immunizations (Example 1) showed strong functional blocking activity in vitro in the TGFβLAP binding inhibition assay (see Example 4), but exhibited cross-reactive binding to non-αVβ6 expressing cell lines (see Example 15). This antibody, sc 264, has an RGD sequence in the CDR3 region, which is presumed to be responsible for the cross-reactive binding. Therefore, site-directed mutagenesis was used to replace the glycine residue in the RGD with an alanine (sc 264 RAD).

A second antibody (sc 188) has a glycosylation site within the FR3 region. This site was eliminated through site-directed mutagenesis with a substitution from NLT to KLT (sc 188 SDM). The mutated versions of these two antibodies were then expressed and purified as described in Examples 7 and 8, and the purified antibodies were analyzed as described in the following examples.

Example 21

Binding Assay to Test Cross-Reactive Binding of Mutant Antibodies

A binding assay was performed to test whether the cross-reactive binding observed in Example 15 was reduced because of site-directed mutagenesis of sc 264. Binding of the antibodies was analyzed on 293T and 293F cell lines to test whether removing the RGD site from sc 264 would result in decreased binding compared with the original antibody.

293T and 293F cells were spun down after collection and resuspended in HBSS with 1% BSA and 1 mM $CaCl_2$ and 1 mM $MgCl_2$ (wash buffer), so that at least 150,000 cells were used in each reaction. Cells were divided between reactions in a V-bottom 96-well plate (Sarstedt), and the cells in the plate were pelleted at 1500 rpm for 3 minutes, after which the HBSS supernatant was removed. The primary antibody was added at the concentration indicated in Table 19 in a volume of 50 μL, and the cells were resuspended and thereafter incubated on ice for 60 minutes. After incubation, the cells were pelleted by centrifugation at 1500 rpm for 3 minutes, resuspended in 100 μL wash buffer, and then pelleted again. Cells were then resuspended in the appropriate secondary antibody at 2 μg/ml with 10 μg/ml 7AAD, and stained on ice for 7 minutes, after which 150 μL of wash buffer was added, and cells were pelleted at 1500 rpm for 3 minutes and then resuspended in 100 μL of HBSS with 1% BSA. Samples were read on a FACS machine with a HTS attachment and the data was analyzed using Cell Quest Pro software. The results are summarized in Table 22, and data appears as Geometric Mean Shift values in arbitrary units. These data demonstrate that at all concentrations tested, sc 264 RAD had significantly less binding to parental 293T cells compared to the original mAb sc 264.

TABLE 22

Cross-reactivity of mutated antibodies to parental cells.

| Antibody | Concentration (ug/ml) | 293T Cells | 293T-αVβ6 Cells |
|---|---|---|---|
| None | n/a | 3 | 2 |
| Mouse IgG2a | 20 | 27 | 8 |
| Human IgG1 | 20 | 4 | 4 |
| Anti-aVb6 | 20 | 4 | 5 |
| sc 264 | 20 | 433 | 6673 |
| sc 264 RAD | 20 | 44 | 7241 |
| sc 188 | 20 | 27 | 6167 |
| sc 188 SDM | 20 | 25 | 6758 |
| sc 264 | 5 | 88 | 6418 |
| sc 264 RAD | 5 | 13 | 6840 |
| sc 188 | 5 | 9 | 5822 |
| sc 188 SDM | 5 | 9 | 6822 |
| sc 264 | 1.25 | 24 | 6230 |
| sc 264 RAD | 1.25 | 7 | 4890 |
| sc 188 | 1.25 | 6 | 6395 |
| sc 188 SDM | 1.25 | 5 | 4532 |

Example 22

Potency Analysis of Mutant Antibodies

In order to determine the concentration ($IC_{50}$) of mutant αVβ6 antibodies required to inhibit TGFβLAP-mediated adhesion of HT-29 cells, the following assay was performed.

Nunc MaxiSorp (Nunc) plates were coated overnight with 50 μL of 10 μg/ml TGF Beta1 LAP (TGFβLAP), and pre-blocked with 3% BSA/PBS for 1 hour prior to the assay. HT29 cells grown to the optimal density were then pelleted and washed twice in HBBS (with 1% BSA and with 1 mM $Ca^{2+}$ and 1 mM $Mg^{2+}$), after which the cells were then resuspended in HBSS at 30,000 cell per well. The coating liquid was removed from the plates, which were then blocked with 100 μL 3% BSA at room temperature for 1 hour and thereafter washed twice with PBS.

Antibody titrations were prepared in 1:4 serial dilutions in a final volume of 30 μL and at two times the final concentration. Care was taken to ensure that the PBS concentration in the control wells matched the PBS concentration in the most dilute antibody well. 30 μL of cells were added to each well, and the cells were incubated in the presence of the antibodies at 4° C. for 40 minutes in a V-bottom plate. The cell-antibody mixtures were transferred to the coated plate and the plate was incubated at 37° C. for 40 minutes. The cells on the coated plates were then washed four times in warm HBSS, and the cells were thereafter frozen at −80° C. for 15 minutes. The cells were allowed to thaw at room temperature, and then 100 μL of CyQuant dye/lysis buffer (Molecular Probes) was added to each well according to the manufacturer's instructions. Fluorescence was read at an excitation wavelength of 485 nm and an emission wavelength of 530 nm. The results for twelve antibodies are summarized in Table 23, and demonstrate that the $IC_{50}$ of the mutant antibodies is consistently less than that of each original antibody.

TABLE 23

Concentration ($IC_{50}$) of mutant antibodies required to inhibit TGFβLAP-mediated adhesion of HT29 cells.

| | n = 1 (ng/ml) | n = 2 (ng/ml) | n = 3(ng/ml) |
|---|---|---|---|
| sc.264 | 113 | 96 | 55 |
| sc.264 RAD | 13 | 13 | 39 |
| sc.264 | 57 | 89 | 46 |
| sc.188 | 125 | 157 | 64 |
| sc.188 SDM | 22 | 24 | 67 |

Example 23

Cross-Reactivity of Mutant Antibodies to α4β1 Integrin

To establish that the mutant antibodies were functional only against the αVβ6 integrin and not the α4β1 integrin, an assay was performed to test the ability of the antibodies to inhibit the adhesion of J6.77 cells to the CS-1 peptide of fibronectin. The assay was performed as described as described below.

Assay plates were coated with the CS-1 peptide of fibronectin. Assay plates were pre-blocked with 3% BSA/PBS for one hour prior to the assay. The J6.77 cells were grown to confluency, then removed from a culture flask, pelleted and washed three times with HBSS. The cells were then resuspended in HBSS at a concentration of 30,000 cells per well. The coating liquid containing the fibronectin fragments was removed, and the plates were blocked with 100 μL of 3% BSA for one hour at room temperature. The coated plates were washed three times with HBSS. Antibody titrations were prepared in 1:4 serial dilutions in a final volume of 30 μL and at twice the final concentration. The resuspended cells were added to the wells containing the titrated antibody in a V-bottom plate, and the cells and antibodies were co-incubated at 4° C. for 40 minutes. The cell-antibody mixture was then transferred to the coated plate, which was thereafter incubated at 37° C. for 40 minutes. The cells on the coated plates were next washed four times in warm HBSS, and the cells in the plates were then frozen at −80° C. for 15 minutes. The cells were allowed to thaw at room temperature, and then 100 μL of CyQuant dye/lysis buffer (Molecular Probes) was added to each well according to the manufacturer's instructions. Fluorescence was read at an excitation wavelength of 485 nm and an emission wavelength of 530 nm.

The results for the two mutant antibodies and their non-mutated counterparts are summarized in Table 24. A commercially available β1 integrin specific antibody was used as a positive control in this assay and exhibited 95% inhibition of adhesion. A commercially available αVβ6 specific antibody served as a negative control in this assay for adhesion to α4β1. All antibodies were used at 5 μg/ml and none of the test antibodies could block adhesion to α4β1.

TABLE 24

Cross-Reactivity to α4β1 Integrin

| Antibody at 5ug/ml | Percent Inhibition |
|---|---|
| sc.188 | 2 |
| sc.188 SDM | −6 |
| sc.264 | −30 |
| sc.264 RAD | −2 |
| Human IgG1 | 26 |
| Human IgG2 | 13 |
| Human IgG4 | 15 |
| Anti-beta 1 Integrin | 95 |

Example 24

Cross-Reactivity of Mutant Antibodies to α5β1 Integrin

To establish that the mutant antibodies were functional only against the αVβ6 integrin and not the α5β1 integrin, an assay was performed to test the ability of the antibodies to inhibit the adhesion of K562 cells to fibronectin. The assay was performed as described as described in Example 14. The results are summarized in Table 25, and demonstrate that none of the tested antibodies could block adhesion to α5β1.

TABLE 25

Cross-Reactivity to α5β1 Integrin.

| Antibody ID | % Inhibition |
|---|---|
| sc 188 | −5 |
| sc 188 SDM | −8 |
| sc 264 | 3 |
| sc 264 RAD | 6 |
| αVβ6 Control | −16 |
| α5β1 Control | 78 |
| Human IgG Control | −12 |

Example 25

Cross-Reactivity of Mutant Antibodies to Mouse and Cynomolgus αVβ6 Integrin

In order to determine if the mutant αVβ6-specific antibodies exhibit cross-reactivity to mouse αVβ6 or Cynomolgus αVβ6, the following assay was performed.

K562 parental cells, or K562 cells expressing Cynomolgus or mouse αVβ6 were spun down after collection and resuspended in HBSS with 1% BSA and 1 mM $CaCl_2$ and 1 mM $MgCl_2$ (wash buffer), so that at least 150,000 cells were used in each reaction. Cells were divided between reactions in a V-bottom 96-well plate (Sarstedt), and the cells in the plate were pelleted at 1500 rpm for 3 minutes, after which the HBSS supernatant was removed. The primary antibody was added in a volume of 50 μL, and the cells were resuspended and thereafter incubated on ice for 60 minutes. After incubation, the cells were pelleted by centrifugation at 1500 rpm for 3 minutes, resuspended in 100 μL wash buffer, and then pelleted again. Cells were then resuspended in the appropriate secondary antibody at 2 μg/ml with 10 μg/ml 7AAD, and stained on ice for 7 minutes, after which 150 μL of wash buffer was added, and cells were pelleted at 1500 rpm for 3 minutes and then resuspended in 100 μL of HBSS with 1% BSA. Samples were read on a FACS machine with a HTS attachment and the data was analyzed using Cell Quest Pro software. The results are summarized in Table 26, and data appears as Geometric Mean Shift values in arbitrary units. These data demonstrate that at the concentrations tested, sc 264 RAD and sc 188 SDM exhibit cross-reactivity to mouse and cynomolgus αVβ6.

TABLE 26

Cross-Reactivity with Mouse and Cynomolgus αVβ6

| Antibodies | Parental | Mouse alphaVbeta6 | Cynomolgus alphaVbeta6 |
|---|---|---|---|
| Cells Alone | 3 | 3 | 3 |
| Gt anti Mouse | 5 | 6 | 7 |
| anti alphaVbeta6 | 15 | 122 | 84 |
| anti alphaV | 109 | 144 | 163 |
| anti beta6 | 26 | 43 | 37 |
| Mouse IgG2a | 23 | 36 | 25 |
| Mouse IgG1 | 12 | 20 | 13 |
| Gt anti Human | 7 | 12 | 7 |
| Human IgG1 | 46 | 108 | 54 |
| sc 133 | 57 | 246 | 154 |
| sc 188 | 55 | 227 | 139 |
| sc 188 SDM | 47 | 219 | 142 |
| sc 254 | 98 | 260 | 190 |
| sc 264 | 33 | 160 | 121 |
| sc 264 RAD | 48 | 196 | 139 |
| sc 298 | 33 | 150 | 97 |

Example 26

Internalization Assay

The internalization of the mutant antibodies was tested using a K562 cell line that stably expressed human αVβ6. The assay was performed as described in Example 15. Internalization of the purified antibodies was compared to a commercially available αVβ6 antibody that was not internalized in this assay.

The results are summarized in Table 27, and demonstrate that the sc 264 RAD mutant antibody is internalized significantly less than the non-mutated sc 264.

TABLE 27

Summary of the Internalization Assay

| Antibody | Concentration (ug/ml) | Percent Internalization |
|---|---|---|
| sc 264 | 10 | 75% |
| sc 264 | 1 | 47% |
| sc 264 RAD | 10 | 42% |
| sc 264 RAD | 1 | 31% |
| sc188 | 10 | 18% |
| sc188 | 1 | 27% |
| sc 188 SDM | 10 | 22% |
| sc 188 SDM | 1 | 17% |

Example 27

Binding Affinity Analysis of SC 264 RAD Using FACS

The binding affinity to αVβ6 of the sc 264 RAD antibody was measured as described in Example 18. The results of this assay are summarized in Table 28, and demonstrate that the sc 264 RAD antibody has an affinity <50 μM.

TABLE 28

Binding Affinity Analysis Using FACS

| mAb Sample | $K_D$ (pM) | 95% CI (pM) |
|---|---|---|
| sc 264 RAD | 46.3 | ±15.9 |

Example 28

Comparison of the Activity of SC 264 RAD with SC 264 RAD/ADY

The activity of sc 264 RAD antibody and the germlined (GL) version of 264RAD (containing the mutation A84D in the light chain), 264 RAD/ADY were compared in a Detroit-562 adhesion assay.

Figure 5:
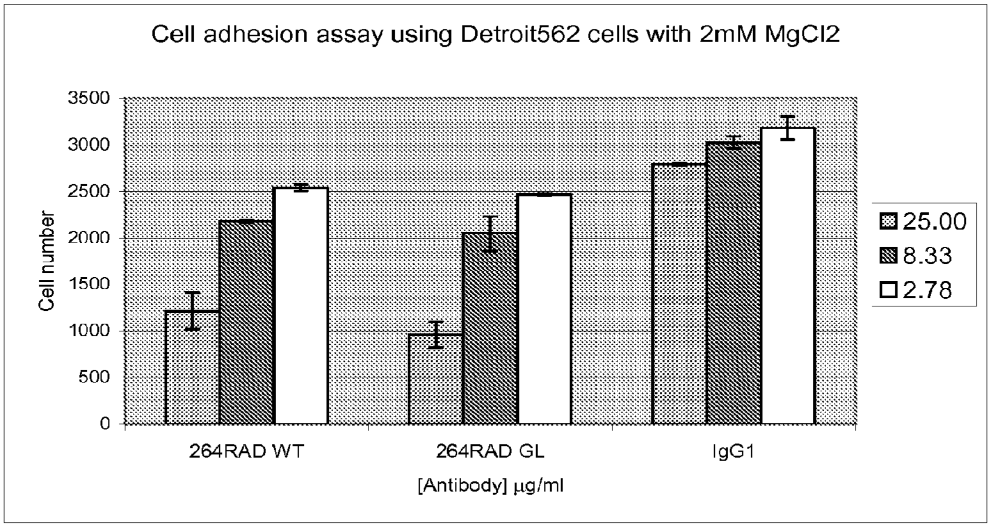
FIG. 5 is a bar chart showing comparison of the activity of 264 RAD with 264 RAD/ADY.

Plates were coated with 0.5 μg/ml GST-TGF-b LAP fusion protein at 4° C. overnight and the following morning, washed, and then blocked with 3% BSA/PBS for 1 hour. Detroit-562 cells (25000 cells per well) were then allowed to adhere to the plates for 45 minutes at 37° C. in HBSS containing 2 mM $MgCl_2$. After 45 minutes the plates were washed three times in PBS and then fixed in ethanol. Cells were visualized by staining with Hoescht and quantitated by counting the number of cells bound per well on a Cellomics Arrayscan II. The data shown in FIG. 5 indicates that both sc 264 RAD and sc 264 RAD/ADY have similar activity and that the ability to block αVβ6 function is maintained in the modified antibody.

Example 29

Growth Study

To establish that the antibodies 264RAD, 133 and 188 SDM block avb6 function in vivo each were tested for the ability to inhibit growth of αV 6 positive tumour xenograft. One such model is the Detroit-562 nasophayngeal cell line, which expresses αVβ6 and also grows as a sub-cutaeneous tumour xenograft.

Detroit 562 cells were cultured in EMEM with Earle's BSS and 2 mM L-Glu+1.0 mM sodium pyruvate, 0.1 mM NEAA+

1.5 g/L sodium bicarbonate+10% FBS. Cells were harvested and resuspended in 50% PBS+50% matrigel. The suspension was then implanted at $5\times10^6$ per mouse in a volume of 0.1 ml within the right flank. Animals were 6-8 week old NCR female nude mice. Dosing was initiated when tumours reached 0.1 cm3 and dosed at 20 mg/kg once weekly for the duration of the study.

Figure 4:
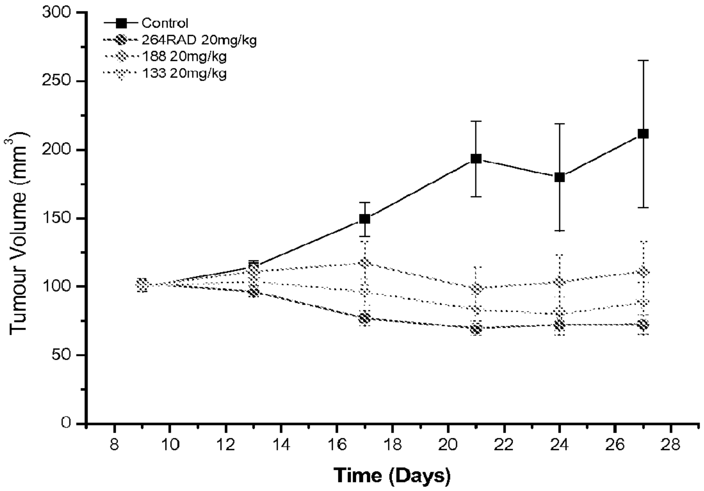
FIG. 4 is a bar graph showing the ability of antibodies 264RAD, 133 and 188 SDM to inhibit tumour growth using the Detroit-562 nasophayngeal cell line.

All three antibodies inhibited tumour growth (see FIG. 4). 264RAD was the most effective, followed by 133, and 188. This data clearly shows that the antibodies 264RAD, 133 and 188 are active in vivo and are able reduce the growth of a tumour dependent on αVβ6 signalling for growth.

INCORPORATION BY REFERENCE

All references cited herein, including patents, patent applications, papers, text books, and the like, and the references cited therein, to the extent that they are not already, are hereby incorporated herein by reference in their entirety for all purposes.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

TABLE 29

Exemplary Antibody Heavy Chain Amino Acid Sequences

| Chain Name | SEQ ID NO: | FR1 | CDR1 | FR2 | CDR2 | FR3 | CDR3 | FR4 |
|---|---|---|---|---|---|---|---|---|
| sc 264 RAD | 75 | **QVQLQESGPGLVK PSQTLSLTCTVS** | **GGSISSG GYYWS** | WIRQHPG KGLEWIG | YIYYSGRTYNNP SLKS | RVTISVDTSKNQFSLKLS SVTAADTAVYYCAR | VATGRADYH FYAMDV | WGQGTTVT VSS |
| sc64 RAD/ADY | 95 | QVQLQESGPGLVK PSQTLSLTCTVS | GGSISSG GYYWS | WIRQHPG KGLEWIG | YIYYSGRTYNNP SLKS | RVTISVDTSKNQFSLKLS SVTAADTAVYYCAR | VATGRADYH FYAMDV | WGQGTTVT VSS |
| sc 188 SDM | 71 | QVQLQESGPGLVK PSQTLSLTCTVS | GGSISSG VYYWT | WIRQHPG NGLEWIG | YIYYSGSTSYNP SLKS | RVTISVDTSKKQFSLKLT SVTAADTAVYYCAR | EGPLRGDYY YGLDV | WGQGTTVT VSS |
| sc 133 TMT | 79 | QVQLVQSGAEVKK PGASVKVSCKAS | GYTFTGY YMH | WVRQAPG QGLEWMG | WINPKSGDTNYA QKFQG | RVTMTRDTSTSTAYMELS RLRSDDTAVYYCAR | RLDV | WGQGTTVT VSS |
| sc 133 WDS | 83 | QVQLVQSGAEVKK PGASVKVSCKAS | GYTFTGY YMH | WVRQAPG QGLEWMG | WINPKSGDTNYA QKFQG | RVTLTRDTSTSTAYMELS RLRSDDTAVYYCAR | RLDV | WGQGTTVT VSS |
| sc 133 TMT/WDS | 87 | QVQLVQSGAEVKK PGASVKVSCKAS | GYTFTGY YMH | WVRQAPG QGLEWMG | WINPKSGDTNYA QKFQG | RVTMTRDTSTSTAYMELS RLRSDDTAVYYCAR | RLDV | WGQGTTVT VSS |

TABLE 30

Exemplary Antibody Light Chain Amino Acid Sequences

| Chain Name | SEQ ID NO: | FR1 | CDR1 | FR2 | CDR2 | FR3 | CDR3 | FR4 |
|---|---|---|---|---|---|---|---|---|
| sc 264 RAD | 77 | SYELTQPSSVSVS PGQTARITC | SGDVLAK KSAR | WFHQKPG QAPVLVIY | KDSERPS | GIPERFSGSSSGTTVTLT ISGAQVEDEAAYYC | YSAADNNLV | FGGGTKLT VL |
| sc 264 RAD/ADY | 97 | SYELTQPSSVSVS PGQTARITC | SGDVLAK KSAR | WFHQKPG QAPVLVIY | KDSERPS | GIPERFSGSSSGTTVTLT ISGAQVEDEA**D**YYC | YSAADNNLV | FGGGTKLT VL |
| sc 188 SDM | 73 | EIVLTQSPGTLSL SPGERATLSC | RAGQTIS SRYLA | WYQQKPG QAPRPLIY | GASSRAT | GIPDRFSGSGSGTDFTLT ISRLEPEDFAVYYC | QQYGSSPRT | FGQGTKVE IK |
| sc 133 TMT | 81 | QSVLTQPPSVSAA PGQKVTISC | SGSSSNI GNNYVS | WYQQLPG TAPKLLIY | DNNKRPS | GIPDRFSGSKSGTSATLG ITGLQTGDEADYYC | GTWNSSLSA GYV | FGTGTKVT VL |
| sc 133 WDS | 85 | QSVLTQPPSVSAA PGQKVTISC | SGSSSNI GNNYVS | WYQQLPG TAPKLLIY | DNNKRPS | GIPDRFSGSKSGTSATLG ITGLQTGDEADYYC | GTWDSSLSA GYV | FGTGTKVT VL |
| sc 133 TMT/WDS | 89 | QSVLTQPPSVSAA PGQKVTISC | SGSSSNI GNNYVS | WYQQLPG TAPKLLIY | DNNKRPS | GIPDRFSGSKSGTSATLG ITGLQTGDEADYYC | GTWDSSLSA GYV | FGTGTKVT VL |

What is claimed is:

1. A method of treating cancer associated with increased activation or expression of αVβ6 in an animal in need thereof, wherein the method comprises administering to the animal a therapeutically effective dose of an antibody that binds αVβ6, wherein the antibody comprises a light chain variable region selected from the group consisting of:

(a) a light chain sequence comprising the sequence of SEQ ID NO:77;

(b) a light chain sequence comprising the sequence of SEQ ID NO:24;

(c) a light chain sequence comprising the sequence of SEQ ID NO:40; and (d) a light chain sequence comprising the sequence of SEQ ID NO:28.

2. The method according to claim 1, wherein the antibody comprises the light chain sequence comprising SEQ ID NO:77.

3. The method according to claim 1, wherein the antibody comprises the light chain sequence comprising SEQ ID NO:24.

4. A method of treating cancer associated with increased activation or expression of αVβ6 in an animal in need thereof, wherein the method comprises administering to the animal a therapeutically effective dose of an antibody that binds αVβ6, wherein the antibody comprises a heavy chain variable region selected from the group consisting of:

(a) a heavy chain sequence comprising the sequence of SEQ ID NO:75;

(b) a heavy chain sequence comprising the sequence of SEQ ID NO:22;

(c) a heavy chain sequence comprising the sequence of SEQ ID NO:38; and (d) a heavy chain sequence comprising the sequence of SEQ ID NO:26.

5. The method according to claim 4, wherein the antibody comprises the light chain sequence comprising SEQ ID NO:75.

6. The method according to claim 4, wherein the antibody comprises the light chain sequence comprising SEQ ID NO:22.

7. A method of treating cancer associated with increased activation or expression of αVβ6 in an animal in need thereof, wherein the method comprises administering to the animal a therapeutically effective dose of an antibody that binds αVβ6, wherein the antibody comprises a heavy chain variable region and a light chain variable region selected from the group consisting of:

(a) a light chain sequence comprising the sequence of SEQ ID NO:77 and a heavy chain sequence comprising the sequence of SEQ ID NO:75;

(b) a light chain sequence comprising the sequence of SEQ ID NO:24 and a heavy chain sequence comprising the sequence of SEQ ID NO:22;

(c) a light chain sequence comprising the sequence of SEQ ID NO:40 and a heavy chain sequence comprising the sequence of SEQ ID NO:38; and (d) a light chain sequence comprising the sequence of SEQ ID NO:28 and a heavy chain sequence comprising the sequence of SEQ ID NO:26.

8. The method according to claim 7, wherein the antibody comprises:

(a) a heavy chain variable region CDR1, CDR2, and CDR3 of SEQ ID NO:75; and (b) a light chain variable region CDR1, CDR2 and CDR3 of SEQ ID NO:77.

* * * * *